(12) United States Patent
Bertina et al.

(10) Patent No.: US 8,067,209 B2
(45) Date of Patent: Nov. 29, 2011

(54) METHOD OF SCREENING FOR THE PRESENCE OF A GENETIC DEFECT ASSOCIATED WITH DEEP VENOUS THROMBOSIS

(75) Inventors: Rogier Maria Bertina, Leiden (NL); Frits R. Rosendaal, Wassenaar (NL); Shirley Uitte de Willige, Leeds (GB); Maria Catharina Henrica de Visser-van Soest, Leiderdorp (NL); Hans Luuk Vos, Bodegraven (NL)

(73) Assignee: Biomerieux B.V., RM Boxtel (NL)

( * ) Notice: Subject to any disclaimer, the term of this patent is extended or adjusted under 35 U.S.C. 154(b) by 399 days.

(21) Appl. No.: 11/887,495

(22) PCT Filed: Mar. 31, 2006

(86) PCT No.: PCT/EP2006/003195
§ 371 (c)(1),
(2), (4) Date: Jul. 1, 2009

(87) PCT Pub. No.: WO2006/103113
PCT Pub. Date: Oct. 5, 2006

(65) Prior Publication Data
US 2009/0269738 A1 Oct. 29, 2009

(30) Foreign Application Priority Data

Apr. 1, 2005 (EP) .................................. 05075764

(51) Int. Cl.
*C12P 19/34* (2006.01)
*C12Q 1/68* (2006.01)
(52) U.S. Cl. ....................................... 435/91.2; 435/6.12
(58) Field of Classification Search .................. None
See application file for complete search history.

(56) References Cited

FOREIGN PATENT DOCUMENTS
WO WO 2005/071114 A1 8/2005

OTHER PUBLICATIONS

International Search Report and Written Opinion for PCT/EP2006/003195; Oct. 20, 2006.
International Preliminary Report on Patentability; Oct. 3, 2007.
Bozic et al. "Fibrinogen Polymorphisms *Taq*1, *Hae* III and *Bc*/I Are Not Associated with a Higher Risk of Deep Vein Thrombosis" *Pathophysiology of Haemostasis and Thrombosis* 33:164-169 (2003).
Database REFSNP ncbi, retrieved from NCBI Database accession No. RS2066854 (2004).
Database REFSNP ncbi, retrieved from NCBI Database accession No. rs2066864 (2001).
Database REFSNP ncbi, retrieved from NCBI Database accession No. rs2066865 (2003).
Database REFSNP ncbi, retrieved from NCBI Database accession No. rs2066861 (2004).
de Willige et al. "Genetic variation in the fibrinogen gamma gene increases the risk for deep venous thrombosis by reducing plasma fibrinogen $\gamma^1$ levels" *Blood 106*(13):4176-4183 (2005).
Drouet et al. "Plasma $\gamma^1$ / $\gamma^1$ fibrogen ratio, a marker of arterial thrombotic activity: a new potential cardiovascular risk factor?" *Blood Coagulation and Fibronolysis 10*(suppl 1):S35-S39 (1999).
Fellowes et al. "Identification and Characterization of Five New Fibrinogen Gene Polymorphisms" *Annals New York Academy of Sciences* 936:636-541 (2001).
Manila et al. "Contribution of haplotypes across the fibrinogen gene cluster to variation in risk of myocardial infarction" *Thromb. Haemost.* 93:5470-577 (2005).

*Primary Examiner* — Teresa E Strzelecka
*Assistant Examiner* — Suchira Pande
(74) *Attorney, Agent, or Firm* — Myers Bigel Sibley & Sajovec, P.A.

(57) ABSTRACT

The present invention relates to a method for screening an individual for the presence in his/her genome of a genetic marker that is indicative of an increased risk of deep venous thrombosis, wherein the genetic marker is haplotype 2 of the fibrinogen γ gene (FGG-H2) as given in FIG. 5A. The genetic marker comprises a set of one, two, three or four mutations in the nucleic acid material encoding fibrinogen γ, the mutations being selected from the group consisting of 129A/T (rs2066854), 7874G/A (rs20668β1), 9615'C/T (rs2066864) and 10034C/T (rs2066865).

27 Claims, 17 Drawing Sheets

Figure 1:
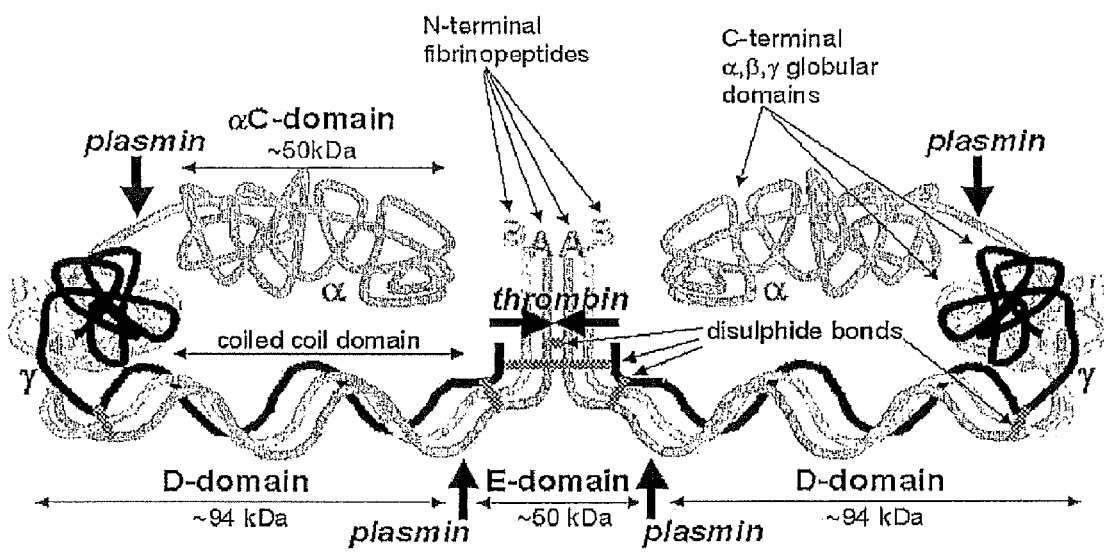

| | F | 129 | 5836 | 7874 | 9340 |
|---|---|---|---|---|---|
| H1 | 0.39 | A | G | G | T |
| H2 | 0.27 | T | G | A | T |
| H3 | 0.31 | A | G | G | C |
| H4 | 0.03 | A | A | G | T |
| H5 | 0.00 | T | G | G | T |

| | F | 251 | 3655 | 3807 | 3845 | 6534 |
|---|---|---|---|---|---|---|
| H1 | 0.28 | G | G | T | G | A |
| H2 | 0.29 | A | G | T | G | G |
| H3 | 0.12 | A | G | T | G | A |
| H4 | 0.13 | G | G | C | G | A |
| H5 | 0.00 | G | G | T | A | A |
| H6 | 0.00 | G | G | C | G | G |
| H7 | 0.18 | G | A | T | G | A |

| | F | 11046 | 10149 | 9952 | 3471 | 1038 | 1643 |
|---|---|---|---|---|---|---|---|
| H1 | 0.33 | T | C | C | T | C | G |
| H2 | 0.20 | T | C | A | T | T | G |
| H3 | 0.11 | T | T | A | T | C | G |
| H4 | 0.16 | C | C | A | T | C | G |
| H5 | 0.02 | C | C | A | C | C | G |
| H6 | 0.16 | T | C | A | T | C | A |
| H7 | 0.02 | T | C | A | T | C | G |

FIG. 5A

*SEQUENCE OF THE HAPLOTYPE2-ALLELE (SEQ ID NO:76)*

```
   1 cttcttcaca gaggcaactg attcaagtca ttacatagtt attgagtgtt aactacaact
  61 atgttaagta cagctatata tgttagatgc cgtagccaca gaaatcagtt tacaatctaa
 121 tgcagtggTt acagcatgta tacatataat ataaggttgc tacaaatgct atctgaggta
 181 gagctgtttg aaagaatact aatacttaaa tgtttaattc aactgacttg attgacaact
 241 gattagctga gtggaaaaga tggatgagaa agattgtgag acttaattgg ctggtggtat
 301 ggtgatatga ttgacaataa ctgctaagtc agagagggat atattaagga ggagaagaaa
 361 agcaacaaat ctggttttga tgtgttcact ttgttataat tattgattat ttactgaata
 421 tgaatattta tctttgtttt tgagtcaata aatataccct tgtaaagaca gaattaaagt
 481 attagtattt ctttcaaact ggaggcattt ctcccactaa catatttcat caaaacttat
 541 aataagcttg gttccagagg aagaaatgag ggataaccaa aaatagagac attaataata
 601 gtgtaacgcc cagtgataaa tctcaatagg cagtgatgac agacatgttt tcccaaacac
 661 aaggatgctg taagggccaa acagaaatga tggcccctcc ccagcacctc attttgcccc
 721 ttccttcagc tatgcctcta ctctccttag atacaaggga ggtggatttt tctcttctct
 781 gagatagctt gatggaacca caggaacaat gaagtgggct cctggctctt ttctctgtgg
 841 cagatggggt gccatgccca ccttcagaca aagggaagat tgagctcaaa agctccctga
 901 gAagtgagag cctatgaaca tggttgacac agagggacag gaatgtattt ccagggtcat
 961 tcattcctgg gaatagtgaa ctgggacatg gggaagtca gtctcctcct gccacagcca
1021 cagattaaaa ataataatgt taactgatcc ctaggctaaa ataatagtgt taactgatcc
1081 ctaagctaag aaagttcttt tggtaattca ggtgatggca gcaggaccca tcttaaggat
1141 agactaggtt tgcttagttc gaggtcatat ctgtttgctc tcagccatgt actggaagaa
1201 gttgcatcac acagcctcca ggactgccct cctcctcaca gcaatggata atgcttcact
1261 agcctttgca gataattttg gatcagagaa aaaaccttga gctgggccaa aaaggaggag
1321 cttcaacctg tgtgcaaaat ctgggaacct gacagtatag gttggggcc aggatgagga
1381 aaaaggaacg ggaaagacct gcccacctt ctggtaagga ggcccgtga tcagctccag
1441 ccatttgcag tcctggctat cccaggagct tacataaagg acaattgga gcctgagagg
1501 tgacagtgct gacactacaa ggctcggagc tccgggcact cagacatcat gagttggtcc
1561 ttgcacccc ggaatttaat tctctacttc tatgctcttt tatttctctc ttcaacatgt
1621 gtagcagtaa gtgtgctctt cacaaaacgt tgtttaaaat ggaaagctgg aaaataaaac
1681 agataataaa ctagtgaaat ttctgtattt tttctctttt agtatgttgc taccagagac
1741 aactgctgca tcttagatga agattcgta agtagttttt atgtttctcc ctttgtgtgt
1801 gaactggaga ggggcagagg aatagaaata attccctcat aaatatcatc tggcacttgt
1861 aactttttaa aaacatagtc taggttttac ctatttttct taatagattt taagagtagc
1921 atctgtctac attttaatc actgttatat tttcagggta gttattgtcc aactacctgt
1981 ggcattgcag atttcctgtc tacttatcaa accaaagtag acaaggatct acagtctttg
2041 gaagacatct tacatcaagt tgaaaacaaa acatcagaag tcaaacagct gataaaagca
```

FIG. 5A (Cont'd.)

```
2101 atccaactca cttataatcc tgatgaatca tcaaaaccaa gtgagaaaat aaagactact
2161 gaccaaaaaa taataataat aatctgtgaa gttcttttgc tgttgtttta gttgttctat
2221 ttgcttaagg attttatgt ctctgatcct atattacaga tatgatagac gctgctactt
2281 tgaagtccag gaaaatgtta gaagaaatta tgaaatatga agcatcgatt ttaacacatg
2341 actcaagtat tcggtaagga tttttgtttt aatttgctct gcaagactga tttagttttt
2401 atttaatatt ctatacttga gtgaaagtaa tttttaatgt gttttcccca tttataatat
2461 cccagtgaca ttatgcctga ttatgttgag catagtagag atagaagttt ttagtgcaat
2521 ataaattata ctgggttata attgcttatt aataatcaca ttgaagaaag atgttctaga
2581 tgtcttcaaa tgctagtttg accatattta tcaaaaattt tttcccatc ccccatttat
2641 cttacaacat aaaatcaatc tcataggaat ttgggtgttg aaaataaaat cctctttata
2701 aaaatgctga caaattggtg gttaaaaaaa ttagcaagca gaggcatagt aaggattttg
2761 gctcctaaag taaattatat tgaatgtgga gcaggaagaa acatgtcttg agagactaag
2821 tgtggcaaat attgcaaagc tcatattgat cattgcagaa tgaacctgca tagtctcttc
2881 ccttcatttg gaagtgaatg tctctgttaa agcttctcag ggactcataa actttctgaa
2941 cataaggtct cagatacagt tttaatattt ttccccaatt ttttttctg aattttctc
3001 aaagcagctt gagaaattga gataaatagt agctagggag aagtggccca ggaagatttt
3061 ctcctctttt tgctatcaga gggcccttgt tattattgtt attattatta cttgcattat
3121 tattgtccat cattgaagtt gaaggaggtt attgtacaga aattgcctaa gacaaggtag
3181 agggaaaacg tggacaaata gtttgtctac ccttttttac ttcaaagaaa gaacggttta
3241 tgcattgtag acagttttct atcattttg gatatttgca agccaccctg taagtaacta
3301 caaaaggagg ttttactt ccccccagtcc attcccaaag ctatgtaacc agaagcatta
3361 aagaagaaag gggaagtatc tgttgtttta tttacatac aataacgttc cagatcatgt
3421 ccctgtgtaa gttatatttt agattgaagc ttatatgtat agcctcagta gatccacaag
3481 tgaaaggtat actccttcag cacatgtgaa ttactgaact gagcttttcc tgcttctaaa
3541 gcatcagggg gtgttcctat taaccagtct cgccactctt gcaggttgct atctgctgtc
3601 ccttatgcat aaagtaaaaa gcaaaatgtc aatgacattt gcttattgac aaggactttg
3661 ttatttgtgt tgggagttga gacaatatgc cccattctaa gtaaaaagat tcaggtccac
3721 attgtattcc tgttttaatt gatttttga tttgtttttc ttttcaaaa agtttataat
3781 tttaattcat gttaatttag taatataatt ttacatttc ctcaagaatg gaataattta
3841 tcagaaagca cttcttaaga aaatacttag cagtttccaa agaaaatata aaattactct
3901 tctgaaagga atacttattt ttgtcttctt attttgtta tcttatgttt ctgtttgtag
3961 atatttgcag gaaatatata attcaaataa tcaaagatt gttaacctga agagaaggt
4021 agcccagctt gaagcacagt gccaggaacc ttgcaaagac acggtgcaaa tccatgatat
4081 cactgggaaa ggtaactgat gaaggttata ttgggattag gttcatcaaa gtaagtaatg
4141 taaggagaa agtatgtact ggaaagtata ggaatagttt agaagtggc tacccattaa
4201 gtctaagaat ttcagttgtc tagacctttc ttgaatagct aaaaaaaaca gtttaaaagg
4261 aatgctgatg tgaaaagtaa gaaaattatt cttggaaaat gaatagttta ctacatgtta
4321 aaagctattt ttcaaggctg gcacagtctt acctgcattt caaccacag taaaagtcga
4381 ttctccttct ctagattgtc aagacattgc caataaggga gctaaacaga gcgggcttta
```

FIG. 5A (Cont'd.)

```
4441 ctttattaaa cctctgaaag ctaaccagca attcttagtc tactgtgaaa tcgatgggtc
4501 tggaaatgga tggactgtgt ttcagaaggt aattttttcc ccaccatgtg tatttaataa
4561 attcctacat tgtttctgcc atatggcaga tacttttcta agcaccttgt gaaccgtagc
4621 tcatttaatc cttgcaatag ccctaagagg aaggtacttc tgttactcct atttacagaa
4681 aaggaaactg aggcacacaa ggttaaataa cttgcccaag accacataac taataagcaa
4741 cagagtcagc atttgaacct aggcagtata gtttcagagt ttgtgacttg actctatatt
4801 gtactggcac tgactttgta gattcatggt ggcacataat catagtacca cagtgacaaa
4861 taaaagaag gaaactcttt tgtcaggtag gtcaagacct gaggtttccc atcacaagat
4921 gaggaagccc aacaccaccc cccaccaccc caccaccatc accacccttt cacacaccag
4981 aggatacact tgggctgctc caagacaagg aacctgtgtt gcatctgcca cttgctgata
5041 cccactagga atcttggctc ctttactttc tgtttacctc ccaccactgt tataactgtt
5101 tctacagggg gcgctcagag ggaatgaatg gtggaagcat tagttgccag acaccgattg
5161 agcaatgggt tccatcataa gtgtaagaat cagtaatatc cagctagagt tctgaagtcg
5221 tctaggtgtc tttttaatat taccactcat ttagaattta tgatgtgcca gaaaccctct
5281 taagtatttc tcttatattc tctctcatga tccttgcagc aaccctaaga agtaaccatc
5341 attttttccta tttgatacat gaggaaactg aggtagcttg gccaagatca cttagttggg
5401 agttgataga accagtgctc tgtattttg acaaaatgtt gacagcattc tctttacatg
5461 cattgatagt ctattttctc cttttgctct tgcaaatgtg taattagaga cttgatgcca
5521 gtgtagattt caagaaaaac tggattcaat ataagaagg atttggacat ctgtctccta
5581 ctggcacaac agaattttgg ctgggaaatg agaagattca tttgataagc acacagtctg
5641 ccatcccata tgcattaaga gtggaactgg aagactggaa tggcagaacc aggtactgtt
5701 ttgaaatgac ttccaacttt ttattgtaaa gattgcctgg aatgtgcact ttccaactat
5761 caatagacaa tggcaaatgc agcctgacaa atgcaaacag cacatccagc caccattttc
5821 tccaggagtc tgtttggttc ttgggcaatc caaaaggta aattctattc aggatgaatc
5881 taagtgtatt ggtacaatct aattaccctg gaaccattca gagtaatagc taattactga
5941 acttttaatc agtcccagga attgagcata aaattataat tttatctagt ctaaattact
6001 atttcatgaa gcaggtatta ttattaatcc catttatag attaacttgc tcaaagtcac
6061 attgctgata agtggtagag gtagaattca gactcaagta gtttaacttt agagcctgtc
6121 ctcttaacaa ctatcctggt tgaaaagcaa atacagcctc ttcagacttc tcagtgcctt
6181 gatggccatt tattctgtca aatcatgagc tacccctaaaa gtaaaccagc tagctctttt
6241 gatgatctag aggcttcttt ttgcttgaga tatttgaagg ttttaagcat tgttacctaa
6301 ttaaatgca gaaaaatatc caaccctctt gttatgttta aggaatagtg aaatatattg
6361 tcttcaaaca catggacttt tttttattgc ttggttggtt tttaatccag aaagtgctat
6421 agtcagtaga ccttcttcta ggaaaggacc ttccatttcc cagccactgg agattagaaa
6481 ataagctaaa tatttctgg aaatttctgt tcattcatta aggcccatcc tttcccccac
6541 tctatagaag tgttgtccac ttgcacaatt ttttccagga aagaatctct ctaactcctt
6601 cagctcacat gctttggacc acacagggaa gactttgatt gtgtaatgcc ctcagaagct
6661 ctccttcttg ccactaccac actgatttga ggaagaaaat cccttagca cctaaccctt
6721 caggtgctat gagtggctaa tggaactgta cctccttcaa gttttgtgca ataattaagg
```

FIG. 5A (Cont'd.)

```
6781 gtcactcact gtcagatact ttctgtgatc tatgataatg tgtgtgcaac acataacatt
6841 tcaataaaag tagaaaatat gaaattagag tcatctacac atctggattt gatcttagaa
6901 tgaaacaagc aaaaaagcat ccaagtgagt gcaattatta gttttcagag atgcttcaaa
6961 ggcttctagg cccatcccgg gaagtgttaa tgagctgtgg actggttcac atatctattg
7021 cctcttgcca gatttgcaaa aaacttcact caatgagcaa atttcagcct taagaaacaa
7081 agtcaaaaat tccaaggaag catcctacga agagggaac ttctgagatc cctgaggagg
7141 gtcagcatgt gatggttgta tttccttctt ctcagtactg cagactatgc catgttcaag
7201 gtgggacctg aagctgacaa gtaccgccta acatatgcct acttcgctgg tgggatgct
7261 ggagatgcct tgatggctt tgattttggc gatgatccta gtgacaagtt tttcacatcc
7321 cataatggca tgcagttcag tacctgggac aatgacaatg ataagtttga aggcaactgt
7381 gctgaacagg atggatctgg ttggtggatg aacaagtgtc acgctggcca tctcaatgga
7441 gtttattacc aaggtatgtt ttcctttctt agattccaag ttaatgtata gtgtatacta
7501 ttttcataaa aataataaa tagatatgaa gaaatgaaga ataatttata aagatagtag
7561 ggattttatc atgttcttta tttcaactaa gttctttgaa actggaagtg gataatacca
7621 agttcatgcc taaaattagc ccttctaaag aaatccacct gctgcaaaat atccagtagt
7681 ttggcattat atgtgaaact atcaccatca tagctggcac tgtgggttgt gggatctcct
7741 ttagacatac aacataaatg atctggatgg attaacatta ctacatggat gcttgttgac
7801 acattaacct ggcttccat gagctttgtg tcagatacac gcagtgaaca ggtgtttgga
7861 ggaacagaat aaaAagaagg caagcactgg taagggcagg ggtttgtgaa agcttgagag
7921 aagagaccag tctgaggaca gtagacactt attttaggat gggggttgga tgaggaggct
7981 atagtttgct ataagcttgg aatggtttgg aacactggtt tcactcacct acccagcagt
8041 tatgtgtggg gaagccttac cgatgctaaa ggatccatgt tacaataatg gcattatttg
8101 gaaatcccag tggtattcca tgaataaaac cactatgaag ataatcccac tcaacagact
8161 ctccgttgga gaaggacagc aacaccaccc tgggaaagcc aaacagtcag accagacctg
8221 tttagcatca gtaggacttc cctaccatat ctgctgggta gatgagtgaa accagtgttc
8281 caaaccactc cgggcttgta gcaaccata gtctcctcat ctaccaagat gagcaacctt
8341 acctcctgat gtcctagcca atcaccaact aggaaacttt gcacagttta tttaaagtaa
8401 cagtttgatt ttcacaatat ttttaaattg gagaaacata acttatcttt gcactcacaa
8461 accacataat gagaagaaac tctaagggaa aatgcttgat ctgtgtgacc cggggcgcca
8521 tgccagagct gtagttcatg ccagtgttgt gctctgacaa gcctttaca gaattacatg
8581 agatctgctt ccctaggaca aggagaaggc aaatcaacag aggctgcact ttaaaatgga
8641 gacataaaat aacatgccag aaccatttcc taaagctcct caatcaacca acaaaattgt
8701 gctttcaaat aacctgagtt gacctcatca ggaattttgt ggctccttct cttctaacct
8761 gcctgaagaa agatggtcca cagcagctga gtcgggatg gataagctta gggacagagg
8821 ccaattaggg aactttgggt ttctagccct actagtagtg aataaattta aagtgtggat
8881 gtgactatga gtcacagcac agatgttgtt taataatatg tttatttat aaattgatat
8941 tttaggaatc tttggagata ttttcagtta gcagataata ctataaattt tatgtaactg
9001 gcaatgcact tcgtaataga cagctcttca tagacttgca gaggtaaaaa gattccagaa
9061 taatgatatg tacatctacg acttgtttta ggtggcactt actcaaaagc atctactcct
```

FIG. 5A (Cont'd.)

```
 9121 aatggttatg ataatggcat tatttgggcc acttggaaaa cccggtggta ttccatgaag
 9181 aaaaccacta tgaagataat cccattcaac agactcacaa ttggagaagg acagcaacac
 9241 cacctggggg gagccaaaca ggtcagacca gagcaccctg cggaaacaga atatgactca
 9301 ctttaccctg aggatgattt gtagaaaatt aactgctaat ttctattgac ccacaaagtt
 9361 tcagaaattc tctgaaagtt tcttcctttt ttctcttact atatttattg atttcaagtc
 9421 ttctattaag gacatttagc cttcaatgga aattaaaact catttaggac tgtatttcca
 9481 aattactgat atcagagtta tttaaaaatt gtttatttga ggagataaca tttcaacttt
 9541 gttcctaaat atataataat aaaatgattg actttatttg cattttatg accacttgtc
 9601 atttattttg tcttTgtaaa ttattttcat tatatcaaat attttagtat gtacttaata
 9661 aaataggaga cattttaga gtttcaaatt cccaggtatt ttccttgttt attaccccta
 9721 aatcattcct atttaattct tcttttaaa tggagaaaat tatgtctttt taatatggtt
 9781 tttgttttgt tatatattca caggctggag acgtttaaaa gaccgtttca aaagagattt
 9841 acttttttaa aggactttat ctgaacagag agatataata ttttttcctat tggacaatgg
 9901 acttgcaaag cttcacttca ttttaagagc aaaagacccc atgttgaaaa ctccataaca
 9961 gttttatgct gatgataatt tatctacatg catttcaata aaccttttgt ttcctaagac
10021 tagatacatg gtaTctttat tgaccattaa aaaccaccac tttttgccaa tttaccaatt
10081 acaattgggc aaccatcagt agtaattgag tcctcatttt atgctaaatg ttatgcctaa
10141 ctctttggga gttacaaagg aaatagca
```

FIG. 5B

*SEQUENCE OF THE REFERENCE FGG GENE ACCORDING TO GENBANK ACCESSION NUMBER AF350254 (SEQ ID NO:77)*

```
   1 cttcttcaca gaggcaactg attcaagtca ttacatagtt attgagtgtt aactacaact
  61 atgttaagta cagctatata tgttagatgc cgtagccaca gaaatcagtt tacaatctaa
 121 tgcagtggat acagcatgta tacatataat ataaggttgc tacaaatgct atctgaggta
 181 gagctgtttg aaagaatact aatacttaaa tgtttaattc aactgacttg attgacaact
 241 gattagctga gtggaaaaga tggatgagaa agattgtgag acttaattgg ctggtggtat
 301 ggtgatatga ttgacaataa ctgctaagtc agagagggat atattaagga ggagaagaaa
 361 agcaacaaat ctggttttga tgtgttcact ttgttataat tattgattat ttactgaata
 421 tgaatattta tctttgtttt tgagtcaata aatatacctt tgtaaagaca gaattaaagt
 481 attagtattt ctttcaaact ggaggcattt ctcccactaa catatttcat caaaacttat
 541 aataagcttg gttccagagg aagaaatgag ggataaccaa aaatagagac attaataata
 601 gtgtaacgcc cagtgataaa tctcaatagg cagtgatgac agacatgttt cccaaacac
 661 aaggatgctg taagggccaa acagaaatga tggcccctcc ccagcacctc attttgcccc
 721 ttccttcagc tatgcctcta ctctccttag atacaaggga ggtggatttt tctcttctct
 781 gagatagctt gatggaacca caggaacaat gaagtgggct cctggctctt ttctctgtgg
 841 cagatggggt gccatgccca ccttcagaca aagggaagat tgagctcaaa agctccctga
 901 ggagtgagag cctatgaaca tggttgacac agagggacag gaatgtattt ccagggtcat
 961 tcattcctgg gaatagtgaa ctgggacatg ggggaagtca gtctcctcct gccacagcca
1021 cagattaaaa ataataatgt taactgatcc ctaggctaaa ataatagtgt taactgatcc
1081 ctaagctaag aaagttcttt tggtaattca ggtgatggca gcaggaccca tcttaaggat
1141 agactaggtt tgcttagttc gaggtcatat ctgtttgctc tcagccatgt actggaagaa
1201 gttgcatcac acagcctcca ggactgccct cctcctcaca gcaatggata atgcttcact
1261 agcctttgca gataattttg gatcagagaa aaaaccttga gctgggccaa aaaggaggag
1321 cttcaacctg tgtgcaaaat ctgggaacct gacagtatag gttggggcc aggatgagga
1381 aaaaggaacg ggaaagacct gcccacccit ctggtaagga ggccccgtga tcagctccag
1441 ccatttgcag tcctggctat cccaggagct tacataaagg gacaattgga gcctgagagg
1501 tgacagtgct gacactacaa ggctcggagc tccgggcact cagacatcat gagttggtcc
1561 ttgcaccccc ggaatttaat tctctacttc tatgctcttt tatttctctc ttcaacatgt
1621 gtagcagtaa gtgtgctctt cacaaaacgt tgtttaaaat ggaagctgg aaaataaaac
1681 agataataaa ctagtgaaat ttctgtattt tttctctttt agtatgttgc taccagagac
1741 aactgctgca tcttagatga agattcgta agtagttttt atgtttctcc ctttgtgtgt
1801 gaactggaga ggggcagagg aatagaaata attccctcat aaatatcatc tggcacttgt
1861 aactttttaa aaacatagtc taggttttac ctattttct taatagattt taagagtagc
1921 atctgtctac attttaatc actgttatat tttcagggta gttattgtcc aactacctgt
```

FIG. 5B (Cont'd.)

```
1981  ggcattgcag atttcctgtc tacttatcaa accaaagtag acaaggatct acagtctttg
2041  gaagacatct tacatcaagt tgaaaacaaa acatcagaag tcaaacagct gataaaagca
2101  atccaactca cttataatcc tgatgaatca tcaaaaccaa gtgagaaaat aaagactact
2161  gaccaaaaaa taataataat aatctgtgaa gttcttttgc tgttgtttta gttgttctat
2221  ttgcttaagg attttatgt ctctgatcct atattacaga tatgatagac gctgctactt
2281  tgaagtccag gaaatgtta gaagaaatta tgaaatatga agcatcgatt ttaacacatg
2341  actcaagtat tcggtaagga ttttttgtttt aatttgctct gcaagactga tttagttttt
2401  atttaatatt ctatacttga gtgaaagtaa tttttaatgt gttttcccca tttataatat
2461  cccagtgaca ttatgcctga ttatgttgag catagtagag atagaagttt ttagtgcaat
2521  ataattata ctgggttata attgcttatt aataatcaca ttgaagaaag atgttctaga
2581  tgtcttcaaa tgctagtttg accatattta tcaaaaattt tttccccatc ccccatttat
2641  cttacaacat aaaatcaatc tcataggaat ttgggtgttg aaaataaaat cctctttata
2701  aaaatgctga caaattggtg gttaaaaaaa ttagcaagca gaggcatagt aaggattttg
2761  gctcctaaag taaattatat tgaatgtgga gcaggaagaa acatgtcttg agagactaag
2821  tgtggcaaat attgcaaagc tcatattgat cattgcagaa tgaacctgca tagtctcttc
2881  ccttcatttg gaagtgaatg tctctgttaa agcttctcag ggactcataa actttctgaa
2941  cataaggtct cagatacagt tttaatattt ttccccaatt ttttttctg aatttttctc
3001  aaagcagctt gagaaattga gataaatagt agctagggag aagtggccca ggaaagattt
3061  ctcctctttt tgctatcaga gggcccttgt tattattgtt attattatta cttgcattat
3121  tattgtccat cattgaagtt gaaggaggtt attgtacaga aattgcctaa gacaaggtag
3181  agggaaaacg tggacaaata gtttgtctac cttttttac ttcaaagaaa gaacggttta
3241  tgcattgtag acagttttct atcatttttg gatatttgca agccaccctg taagtaacta
3301  caaaggagg gttttttactt cccccagtcc attcccaaag ctatgtaacc agaagcatta
3361  aagaagaaag gggaagtatc tgttgttta tttacatac aataacgttc cagatcatgt
3421  ccctgtgtaa gttatatttt agattgaagc ttatatgtat agcctcagta gatccacaag
3481  tgaaaggtat actccttcag cacatgtgaa ttactgaact gagcttttcc tgcttctaaa
3541  gcatcagggg gtgttcctat taaccagtct cgccactctt gcaggttgct atctgctgtc
3601  ccttatgcat aaagtaaaaa gcaaatgtc aatgacattt gcttattgac aaggactttg
3661  ttatttgtgt tgggagttga acaatatgc cccattctaa gtaaaaagat tcaggtccac
3721  attgtattcc tgttttaatt gattttttga tttgttttc ttttcaaaa agtttataat
3781  tttaattcat gttaatttag taatataatt ttacatttc ctcaagaatg gaataattta
3841  tcagaaagca cttcttaaga aaatacttag cagtttccaa agaaaatata aaattactct
3901  tctgaaagga atacttatt ttgtcttctt attttgtta tcttatgttt ctgtttgtag
3961  atatttgcag gaaatatata attcaaataa tcaaaagatt gttaacctga agagaaggt
4021  agcccagctt gaagcacagt gccaggaacc ttgcaaagac acggtgcaaa tccatgatat
4081  cactgggaaa ggtaactgat gaaggttata ttgggattag gttcatcaaa gtaagtaatg
4141  taaggagaa agtatgtact ggaagtata ggaatagttt agaagtggc tacccattaa
4201  gtctaagaat ttcagttgtc tagacctttc ttgaatagct aaaaaaaca gtttaaaagg
4261  aatgctgatg tgaaaagtaa gaaaattatt cttggaaaat gaatagttta ctacatgtta
```

FIG. 5B (Cont'd.)

```
4321 aaagctattt ttcaaggctg gcacagtctt acctgcattt caaaccacag taaaagtcga
4381 ttctccttct ctagattgtc aagacattgc caataaggga gctaaacaga gcgggcttta
4441 ctttattaaa cctctgaaag ctaaccagca attcttagtc tactgtgaaa tcgatgggtc
4501 tggaaatgga tggactgtgt ttcagaaggt aattttttcc ccaccatgtg tatttaataa
4561 attcctacat tgtttctgcc atatggcaga tacttttcta agcaccttgt gaaccgtagc
4621 tcatttaatc cttgcaatag ccctaagagg aaggtacttc tgttactcct atttacagaa
4681 aaggaaactg aggcacacaa ggttaaataa cttgcccaag accacataac taataagcaa
4741 cagagtcagc atttgaacct aggcagtata gtttcagagt tgtgacttg actctatatt
4801 gtactggcac tgactttgta gattcatggt ggcacataat catagtacca cagtgacaaa
4861 taaaagaag gaaactcttt tgtcaggtag gtcaagacct gaggtttccc atcacaagat
4921 gaggaagccc aacaccaccc cccaccaccc caccaccatc accacccttt cacacaccag
4981 aggatacact tgggctgctc caagacaagg aacctgtgtt gcatctgcca cttgctgata
5041 cccactagga atcttggctc ctttacttc tgtttacctc ccaccactgt tataactgtt
5101 tctacagggg gcgctcagag ggaatgaatg gtggaagcat tagttgccag acaccgattg
5161 agcaatgggt tccatcataa gtgtaagaat cagtaatatc cagctagagt tctgaagtcg
5221 tctaggtgtc tttttaatat taccactcat ttagaattta tgatgtgcca gaaaccctct
5281 taagtatttc tcttatattc tctctcatga tccttgcagc aaccctaaga agtaaccatc
5341 attttttccta tttgatacat gaggaaactg aggtagcttg gccaagatca cttagttggg
5401 agttgataga accagtgctc tgtattttg acaaaatgtt gacagcattc tctttacatg
5461 cattgatagt ctattttctc cttttgctct tgcaaatgtg taattagaga cttgatggca
5521 gtgtagattt caagaaaaac tggattcaat ataagaagg atttggacat ctgtctccta
5581 ctggcacaac agaattttgg ctgggaaatg agaagattca tttgataagc acacagtctg
5641 ccatcccata tgcattaaga gtggaactgg aagactggaa tggcagaacc aggtactgtt
5701 ttgaaatgac ttccaacttt ttattgtaaa gattgcctgg aatgtgcact ttccaactat
5761 caatagacaa tggcaaatgc agcctgacaa atgcaaacag cacatccagc caccattttc
5821 tccaggagtc tgtttggttc ttgggcaatc caaaaggta aattctattc aggatgaatc
5881 taagtgtatt ggtacaatct aattaccctg gaaccattca gagtaatagc taattactga
5941 acttttaatc agtcccagga attgagcata aaattataat tttatctagt ctaaattact
6001 atttcatgaa gcaggtatta ttattaatcc catttttatag attaacttgc tcaaagtcac
6061 attgctgata agtggtagag gtagaattca gactcaagta gtttaacttt agagcctgtc
6121 ctcttaacaa ctatcctggt tgaaaagcaa atacagcctc ttcagacttc tcagtgcctt
6181 gatggccatt tattctgtca atcatgagc taccctaaaa gtaaaccagc tagctctttt
6241 gatgatctag aggcttcttt ttgcttgaga tatttgaagg ttttaagcat tgttacctaa
6301 ttaaaatgca gaaaaatatc caaccctctt gttatgttta aggaatagtg aaatatattg
6361 tcttcaaaca catggacttt tttttattgc ttggttggtt tttaatccag aaagtgctat
6421 agtcagtaga ccttcttcta ggaaaggacc ttccatttcc cagccactgg agattagaaa
6481 ataagctaaa tattttctgg aaatttctgt tcattcatta aggcccatcc tttcccccac
6541 tctatagaag tgttgtccac ttgcacaatt ttttccagga aagaatctct ctaactcctt
6601 cagctcacat gctttggacc acacagggaa gactttgatt gtgtaatgcc ctcagaagct
```

FIG. 5B (Cont'd.)

```
6661 ctccttcttg ccactaccac actgatttga ggaagaaaat ccctttagca cctaacccttt
6721 caggtgctat gagtggctaa tggaactgta cctccttcaa gttttgtgca ataattaagg
6781 gtcactcact gtcagatact ttctgtgatc tatgataatg tgtgtgcaac acataacatt
6841 tcaataaaag tagaaaatat gaaattagag tcatctacac atctggattt gatcttagaa
6901 tgaaacaagc aaaaaagcat ccaagtgagt gcaattatta gttttcagag atgcttcaaa
6961 ggcttctagg cccatcccgg gaagtgttaa tgagctgtgg actggttcac atatctattg
7021 cctcttgcca gatttgcaaa aaacttcact caatgagcaa atttcagcct taagaaacaa
7081 agtcaaaaat tccaaggaag catcctacga aagagggaac ttctgagatc cctgaggagg
7141 gtcagcatgt gatggttgta tttccttctt ctcagtactg cagactatgc catgttcaag
7201 gtgggacctg aagctgacaa gtaccgccta acatatgcct acttcgctgg tggggatgct
7261 ggagatgcct ttgatggctt tgattttggc gatgatccta gtgacaagtt tttcacatcc
7321 cataatggca tgcagttcag tacctgggac aatgacaatg ataagtttga aggcaactgt
7381 gctgaacagg atggatctgg ttggtggatg aacaagtgtc acgctggcca tctcaatgga
7441 gtttattacc aaggtatgtt ttcctttctt agattccaag ttaatgtata gtgtatacta
7501 ttttcataaa aaataataaa tagatatgaa gaaatgaaga ataatttata aagatagtag
7561 ggatttttatc atgttcttta tttcaactaa gttctttgaa actggaagtg gataatacca
7621 agttcatgcc taaaattagc ccttctaaag aaatccacct gctgcaaaat atccagtagt
7681 ttggcattat atgtgaaact atcaccatca tagctggcac tgtgggttgt gggatctcct
7741 ttagacatac aacataaatg atctggatgg attaacatta ctacatggat gcttgttgac
7801 acattaacct ggcttcccat gagctttgtg tcagatacac gcagtgaaca ggtgtttgga
7861 ggaacagaat aaagagaagg caagcactgg taagggcagg ggtttgtgaa agcttgagag
7921 aagagaccag tctgaggaca gtagacactt attttaggat gggggttgga tgaggaggct
7981 atagtttgct ataagcttgg aatggtttgg aacactggtt tcactcacct acccagcagt
8041 tatgtgtggg gaagccttac cgatgctaaa ggatccatgt tacaataatg gcattatttg
8101 gaaatcccag tggtattcca tgaataaaac cactatgaag ataatcccac tcaacagact
8161 ctccgttgga gaaggacagc aacaccaccc tgggaaagcc aaacagtcag accagacctg
8221 tttagcatca gtaggacttc cctaccatat ctgctggta gatgagtgaa accagtgttc
8281 caaaccactc cgggcttgta gcaaaccata gtctcctcat ctaccaagat gagcaacctt
8341 acctcctgat gtcctagcca atcaccaact aggaaacttt gcacagttta tttaaagtaa
8401 cagtttgatt ttcacaatat ttttaaattg gagaaacata acttatcttt gcactcacaa
8461 accacataat gagaagaaac tctaagggaa aatgcttgat ctgtgtgacc cggggcgcca
8521 tgccagagct gtagttcatg ccagtgttgt gctctgacaa gccttttaca gaattacatg
8581 agatctgctt ccctaggaca aggagaaggc aaatcaacag aggctgcact ttaaaatgga
8641 gacataaaat aacatgccag aaccatttcc taaagctcct caatcaacca acaaaattgt
8701 gctttcaaat aacctgagtt gacctcatca ggaattttgt ggctccttct cttctaacct
8761 gcctgaagaa agatggtcca cagcagctga gtccgggatg gataagctta gggacagagg
8821 ccaattaggg aactttgggt ttctagccct actagtagtg aataaattta aagtgtggat
8881 gtgactatga gtcacagcac agatgttgtt taataatatg tttattttat aaattgatat
8941 tttaggaatc tttggagata ttttcagtta gcagataata ctataaattt tatgtaactg
```

FIG. 5B (Cont'd.)

```
 9001 gcaatgcact tcgtaataga cagctcttca tagacttgca gaggtaaaaa gattccagaa
 9061 taatgatatg tacatctacg acttgtttta ggtggcactt actcaaaagc atctactcct
 9121 aatggttatg ataatggcat tatttgggcc acttggaaaa cccggtggta ttccatgaag
 9181 aaaccacta  tgaagataat cccattcaac agactcacaa ttggagaagg acagcaacac
 9241 cacctggggg gagccaaaca ggtcagacca gagcaccctg cggaaacaga atatgactca
 9301 ctttaccctg aggatgattt gtagaaaatt aactgctaat ttctattgac ccacaaagtt
 9361 tcagaaattc tctgaaagtt tcttcctttt ttctcttact atatttattg atttcaagtc
 9421 ttctattaag gacatttagc cttcaatgga aattaaaact catttaggac tgtatttcca
 9481 aattactgat atcagagtta tttaaaaatt gtttatttga ggagataaca tttcaacttt
 9541 gttcctaaat atataataat aaaatgattg actttatttg cattttatg  accacttgtc
 9601 atttattttg tcttcgtaaa ttattttcat tatatcaaat attttagtat gtacttaata
 9661 aaataggaga acatttttaga gtttcaaatt cccaggtatt ttccttgttt attaccccta
 9721 aatcattcct atttaattct tcttttttaaa tggagaaaat tatgtctttt taatatggtt
 9781 tttgttttgt tatatattca caggctggag acgtttaaaa gaccgtttca aaagagattt
 9841 acttttttaa aggactttat ctgaacagag agatataata ttttccctat tggacaatgg
 9901 acttgcaaag cttcacttca ttttaagagc aaaagacccc atgttgaaaa ctccataaca
 9961 gttttatgct gatgataatt tatctacatg catttcaata aaccttttgt ttcctaagac
10021 tagatacatg gtaccttat  tgaccattaa aaaccaccac ttttttgccaa tttaccaatt
10081 acaattgggc aaccatcagt agtaattgag tcctcatttt atgctaaatg ttatgcctaa
10141 ctctttggga gttacaaagg aaatagca
```

FIG. 9A

<u>CTAGACCACCATGG</u>GTGGCACTTACTCAAAAGCATCTACTCCTAATGGTTATGATAATGGCATTAT

<u>TTGGGCCACTTGGAAAACCCGGTGGTATTCCATGAAGAAAACCACTATGAAGATAATCCCATTCA</u>

<u>ACAGACTCACAATTGGAGAAGGACAGCAACACCACCTGGGGGGAGCC</u>`AAACAGGTCAGACCA`

`GAGCACCCT`GCGGAAACAGAATAT*GACTCACTTTACCCTGAGGATGA*TTTG*T*AGAAAATTAACT

GCTAATTTCTATTGACCCACAAAGTTTCAGAAATTCTCTGAAAGTTTCTTCCTTTTTTCTCTTACTA

TATTTATTGATTTCAAGTCTTCTATTAAGGACATTTAGCCTTCAATGGAAATTAAAACTCATTTAGG

ACTGTATTTCCAAATTACTGATATCAGAGTTATTTAAAAATTGTTTATTTGAGGAGATAACATTTCA

ACTTTGTTCCTAAATATATAATAATAAAATGATTGACTTTATTTGCATTTTTATGACCACTTGTCATT

TATTTTGTCTTC*GTAAATTATTTTCATTATATCAAATATTTTAGTATGTACTTAATAAAATAGGAGAA

CATTTTAGAGTTTCAAATTCCCAGGTATTTTCCTTGTTTATTACCCCTAAATCATTCCTATTTAATTCT

TCTTTTTAAATGGAGAAAATTATGTCTTTTTAATATGGTTTTTGTTTTGTTATATATTCACAGG`CTG`

`GAGACGTTTAAAAGACCGTTTC`AAAGAGATTTACTTTTTTAAAGGACTTTATCTGAACAGAGAG

<u>ATATAATATTTTTCCTATTGGACAAT</u>GGACTTGCAAAGCTTCACTTC<u>ATTTAAGAGCAAAAGACC</u>

<u>CCATGTTGAAAACTCCATAACAGTTTTATGCTGATGATAATTTATCTACATGCATTTCAATAAACCT</u>

<u>TTTGTTTCCTAAGAC</u>TAGATACATGGTA<u>C</u>**CTTTATTGACCATTAAAAACCACCACTTTTT

GCCAATTTACCAATTACAATTGGGCAACCATCAGTAGTAATTGAGTCCTCATTTT

A<u>TGCTAAATGTTATGCCTAACTCTTTGCATT</u> (SEQ ID NO:86)

Insert sequence: FGG nt 9090 to nt 10151
BOLD DOUBLE UNDERLINED: primers used to obtain the insert from DNA
<u>DOTTED UNDERLINED</u>: exon 9 and exon 10
NORMAL: intron 9
<u>STRIPED UNDERLINED</u>: 3'UTR
*ITALIC*: nucleotide sequence coding for the 20 amino acids of the γ' chain
BOLD UNDERLINED: reversed primers Real Time PCR
BOLD: probes Real Time PCR
C* in the middle SNP 9815
C** at the end: SNP 10034

FIG. 9B

CTAGACCACCATGGGTGGCACTTACTCAAAAGCATCTACTCCTAATGGTTATGATAATGGCATTAT
TTGGGCCACTTGGAAAACCCGGTGGTATTCCATGAAGAAAACCACTATGAAGATAATCCCATTCA
ACAGACTCACAATTGGAGAAGGACAGCAACACCACCTGGGGGGAGCCAAACAGGTCAGACCAG
AGCACCCTGCGGAAACAGAATATGACTCACTTTACCCTGAGGATGATTTGTAGAAAATTAACTGC
TAATTTCTATTGACCCACAAAGTTTCAGAAATTCTCTGAAAGTTTCTTCCTTTTTTCTCTTACTATAT
TTATTGATTTCAAGTCTTCTATTAAGGACATTTAGCCTTCAATGGAAATTAAAACTCATTTAGGACT
GTATTTCCAAATTACTGATATCAGAGTTATTTAAAAATTGTTTATTTGAGGAGATAACATTTCAACTT
TGTTCCTAAATATATAATAATAAAATGATTGACTTTATTTGCATTTTTATGACCACTTGTCATTTATTT
TGTCTTCGTAAATTATTTTCATTATATCAAATATTTTAGTATGTACTTAATAAAATAGGAGAACATTT
TAGAGTTTCAAATTCCCAGGTATTTTCCTTGTTTATTACCCCTAAATCATTCCTATTTAATTCTTCTTT
TTAAATGGAGAAAATTATGTCTTTTTAATATGGTTTTTGTTTTGTTATATATTCACAGGCTGGAGAC
GTTTAAAAGACCGTTTCAAAAGAGATTTACTTTTTTAAAGGACTTTATCTGAACAGAGAGATATAA
TATTTTTCCTATTGGACAATGGACTTGCAAAGCTTCACTTCATTTTAAGAGCAAAAGACCCCATGT
TGAAAACTCCATAACAGTTTTATGCTGATGATAATTTATCTACATGCATTTCAATAAACCTTTTGTTT
CCTAAGACTAGATACATGGTA<u>C</u>CTTTATTGACCATTAAAAACCACCACTTTTTGCCAATTTACCAAT
TACAATTGGGCAACCATCAGTAGTAATTGAGTCCTCATTTTATGCTAAATGTTATGCCTAACTCTTT
GCATT (SEQ ID NO:86)

ance with an allele frequency of 25% (http://innateimmunity.net). "Haplotype" as used herein means a series of single nucleotide polymorphisms (SNPs) that inherit together.

SEQUENCE LISTING

<160> NUMBER OF SEQ ID NOS: 86

<210> SEQ ID NO 1
<211> LENGTH: 21
<212> TYPE: DNA
<213> ORGANISM: Artificial
<220> FEATURE:
<223> OTHER INFORMATION: First oligonucleotide 1

<400> SEQUENCE: 1
cttcacagag gcaactgatt c                21

<210> SEQ ID NO 2
<211> LENGTH: 22
<212> TYPE: DNA
<213> ORGANISM: Artificial
<220> FEATURE:
<223> OTHER INFORMATION: First oligonucleotide 2

<400> SEQUENCE: 2
ccttcagaca aagggaagat tg               22

<210> SEQ ID NO 3
<211> LENGTH: 18
<212> TYPE: DNA
<213> ORGANISM: Artificial
<220> FEATURE:
<223> OTHER INFORMATION: First oligonucleotide 3

<400> SEQUENCE: 3
agctccagcc atttgcag                    18

<210> SEQ ID NO 4
<211> LENGTH: 20
<212> TYPE: DNA
<213> ORGANISM: Artificial
<220> FEATURE:
<223> OTHER INFORMATION: First oligonucleotide 4

<400> SEQUENCE: 4
tcaggtccac attgtattcc                  20

<210> SEQ ID NO 5
<211> LENGTH: 21
<212> TYPE: DNA
<213> ORGANISM: Artificial
<220> FEATURE:
<223> OTHER INFORMATION: First oligonucleotide 5

<400> SEQUENCE: 5
gggagttgat agaaccagtg c                21

<210> SEQ ID NO 6

```
<211> LENGTH: 20
<212> TYPE: DNA
<213> ORGANISM: Artificial
<220> FEATURE:
<223> OTHER INFORMATION: First oligonucleotide 6

<400> SEQUENCE: 6
ttccaaggaa gcatcctacg                                           20

<210> SEQ ID NO 7
<211> LENGTH: 20
<212> TYPE: DNA
<213> ORGANISM: Artificial
<220> FEATURE:
<223> OTHER INFORMATION: First oligonucleotide 7

<400> SEQUENCE: 7
gtaactggca atgcacttcg                                           20

<210> SEQ ID NO 8
<211> LENGTH: 25
<212> TYPE: DNA
<213> ORGANISM: Artificial
<220> FEATURE:
<223> OTHER INFORMATION: Fist oligonucleotide 8

<400> SEQUENCE: 8
gagaacattt tagagtttca aattc                                     25

<210> SEQ ID NO 9
<211> LENGTH: 30
<212> TYPE: DNA
<213> ORGANISM: Artificial
<220> FEATURE:
<223> OTHER INFORMATION: First oligonucleotide 9

<400> SEQUENCE: 9
acatgcattt caataaacct tttgtttcct                                30

<210> SEQ ID NO 10
<211> LENGTH: 21
<212> TYPE: DNA
<213> ORGANISM: Artificial
<220> FEATURE:
<223> OTHER INFORMATION: Second oligonucleotide 1

<400> SEQUENCE: 10
gtgtcaacca tgttcatagg c                                         21

<210> SEQ ID NO 11
<211> LENGTH: 21
<212> TYPE: DNA
<213> ORGANISM: Artificial
<220> FEATURE:
<223> OTHER INFORMATION: Second oligonucleotide 2

<400> SEQUENCE: 11
ccttttatgt aagctcctgg g                                         21

<210> SEQ ID NO 12
<211> LENGTH: 23
<212> TYPE: DNA
<213> ORGANISM: Artificial
<220> FEATURE:
<223> OTHER INFORMATION: Second oligonucleotide 3

<400> SEQUENCE: 12
```
cataatcagg cataatgtca ctg                                          23

<210> SEQ ID NO 13
<211> LENGTH: 19
<212> TYPE: DNA
<213> ORGANISM: Artificial
<220> FEATURE:
<223> OTHER INFORMATION: Second oligonucleotide 4

<400> SEQUENCE: 13
tgagctacgg ttcacaagg                                               19

<210> SEQ ID NO 14
<211> LENGTH: 20
<212> TYPE: DNA
<213> ORGANISM: Artificial
<220> FEATURE:
<223> OTHER INFORMATION: Second oligonucleotide 5

<400> SEQUENCE: 14
gactcctgga gaaaatggtg                                              20

<210> SEQ ID NO 15
<211> LENGTH: 21
<212> TYPE: DNA
<213> ORGANISM: Artificial
<220> FEATURE:
<223> OTHER INFORMATION: Second oligonucleotide 6

<400> SEQUENCE: 15
ggtggatttc tttagaaggg c                                            21

<210> SEQ ID NO 16
<211> LENGTH: 20
<212> TYPE: DNA
<213> ORGANISM: Artificial
<220> FEATURE:
<223> OTHER INFORMATION: Second oligonucleotide 7

<400> SEQUENCE: 16
gctttgcaag tccattgtcc                                              20

<210> SEQ ID NO 17
<211> LENGTH: 21
<212> TYPE: DNA
<213> ORGANISM: Artificial
<220> FEATURE:
<223> OTHER INFORMATION: Second oligonucleotide 8

<400> SEQUENCE: 17
gctatttcct ttgtaactcc c                                            21

<210> SEQ ID NO 18
<211> LENGTH: 24
<212> TYPE: DNA
<213> ORGANISM: Artificial
<220> FEATURE:
<223> OTHER INFORMATION: Second oligonucleotide 9

<400> SEQUENCE: 18
ggtaaattgg caaaaagtgg tggt                                         24

<210> SEQ ID NO 19
<211> LENGTH: 19
<212> TYPE: DNA
<213> ORGANISM: Artificial
<220> FEATURE:

-continued

<223> OTHER INFORMATION: Oligo for detecting FGG-H2 haplotype 1

<400> SEQUENCE: 19
atggtcaata aagatacca                                                    19

<210> SEQ ID NO 20
<211> LENGTH: 24
<212> TYPE: DNA
<213> ORGANISM: Artificial
<220> FEATURE:
<223> OTHER INFORMATION: Probe for detecting FGG-H2 haplotype 2

<400> SEQUENCE: 20
ttttaatggt caataaggt acca                                               24

<210> SEQ ID NO 21
<211> LENGTH: 21
<212> TYPE: DNA
<213> ORGANISM: Artificial
<220> FEATURE:
<223> OTHER INFORMATION: PR1 forward FGG

<400> SEQUENCE: 21
cttcacagag gcaactgatt c                                                 21

<210> SEQ ID NO 22
<211> LENGTH: 21
<212> TYPE: DNA
<213> ORGANISM: Artificial
<220> FEATURE:
<223> OTHER INFORMATION: PR1 backward FGG

<400> SEQUENCE: 22
gtgtcaacca tgttcatagg c                                                 21

<210> SEQ ID NO 23
<211> LENGTH: 22
<212> TYPE: DNA
<213> ORGANISM: Artificial
<220> FEATURE:
<223> OTHER INFORMATION: PR2 forward FGG

<400> SEQUENCE: 23
ccttcagaca aagggaagat tg                                                22

<210> SEQ ID NO 24
<211> LENGTH: 21
<212> TYPE: DNA
<213> ORGANISM: Artificial
<220> FEATURE:
<223> OTHER INFORMATION: PR2 backward FGG

<400> SEQUENCE: 24
ccttttatgt aagctcctgg g                                                 21

<210> SEQ ID NO 25
<211> LENGTH: 18
<212> TYPE: DNA
<213> ORGANISM: Artificial
<220> FEATURE:
<223> OTHER INFORMATION: Exon 1-4 forward

<400> SEQUENCE: 25
agctccagcc atttgcag                                                     18

<210> SEQ ID NO 26

```
<211> LENGTH: 23
<212> TYPE: DNA
<213> ORGANISM: Artificial
<220> FEATURE:
<223> OTHER INFORMATION: Exon 1-4 backward FGG

<400> SEQUENCE: 26
cataatcagg cataatgtca ctg                                              23

<210> SEQ ID NO 27
<211> LENGTH: 20
<212> TYPE: DNA
<213> ORGANISM: Artificial
<220> FEATURE:
<223> OTHER INFORMATION: Exon 5-6 forward FGG

<400> SEQUENCE: 27
tcaggtccac attgtattcc                                                  20

<210> SEQ ID NO 28
<211> LENGTH: 19
<212> TYPE: DNA
<213> ORGANISM: Artificial
<220> FEATURE:
<223> OTHER INFORMATION: Exon 5-6 backward

<400> SEQUENCE: 28
tgagctacgg ttcacaagg                                                   19

<210> SEQ ID NO 29
<211> LENGTH: 21
<212> TYPE: DNA
<213> ORGANISM: Artificial
<220> FEATURE:
<223> OTHER INFORMATION: Exon 7 forward FGG

<400> SEQUENCE: 29
gggagttgat agaaccagtg c                                                21

<210> SEQ ID NO 30
<211> LENGTH: 20
<212> TYPE: DNA
<213> ORGANISM: Artificial
<220> FEATURE:
<223> OTHER INFORMATION: Exon 7 backward FGG

<400> SEQUENCE: 30
gactcctgga gaaaatggtg                                                  20

<210> SEQ ID NO 31
<211> LENGTH: 20
<212> TYPE: DNA
<213> ORGANISM: Artificial
<220> FEATURE:
<223> OTHER INFORMATION: Exon 8 forward FGG

<400> SEQUENCE: 31
ttccaaggaa gcatcctacg                                                  20

<210> SEQ ID NO 32
<211> LENGTH: 21
<212> TYPE: DNA
<213> ORGANISM: Artificial
<220> FEATURE:
<223> OTHER INFORMATION: Exon 8 backward FGG

<400> SEQUENCE: 32
```
ggtggatttc tttagaaggg c                                          21

<210> SEQ ID NO 33
<211> LENGTH: 20
<212> TYPE: DNA
<213> ORGANISM: Artificial
<220> FEATURE:
<223> OTHER INFORMATION: Exon 9-10 forward FGG

<400> SEQUENCE: 33
gtaactggca atgcacttcg                                            20

<210> SEQ ID NO 34
<211> LENGTH: 20
<212> TYPE: DNA
<213> ORGANISM: Artificial
<220> FEATURE:
<223> OTHER INFORMATION: Exon 9-10 backward FGG

<400> SEQUENCE: 34
gctttgcaag tccattgtcc                                            20

<210> SEQ ID NO 35
<211> LENGTH: 25
<212> TYPE: DNA
<213> ORGANISM: Artificial
<220> FEATURE:
<223> OTHER INFORMATION: 3'UTR forward FGG

<400> SEQUENCE: 35
gagaacattt tagagtttca aattc                                      25

<210> SEQ ID NO 36
<211> LENGTH: 21
<212> TYPE: DNA
<213> ORGANISM: Artificial
<220> FEATURE:
<223> OTHER INFORMATION: 3'UTR backward FGG

<400> SEQUENCE: 36
gctatttcct ttgtaactcc c                                          21

<210> SEQ ID NO 37
<211> LENGTH: 19
<212> TYPE: DNA
<213> ORGANISM: Artificial
<220> FEATURE:
<223> OTHER INFORMATION: PR forward FGA

<400> SEQUENCE: 37
ccttcagggc cagcttatc                                             19

<210> SEQ ID NO 38
<211> LENGTH: 20
<212> TYPE: DNA
<213> ORGANISM: Artificial
<220> FEATURE:
<223> OTHER INFORMATION: PR backward FGA

<400> SEQUENCE: 38
cacttaggac caggcagacg                                            20

<210> SEQ ID NO 39
<211> LENGTH: 20
<212> TYPE: DNA
<213> ORGANISM: Artificial
<220> FEATURE:

```
<223> OTHER INFORMATION: Exon 1 forward FGA

<400> SEQUENCE: 39
cagccccacc cttagaaaag                                              20

<210> SEQ ID NO 40
<211> LENGTH: 23
<212> TYPE: DNA
<213> ORGANISM: Artificial
<220> FEATURE:
<223> OTHER INFORMATION: Exon 1 backward FGA

<400> SEQUENCE: 40
cctggggtca taaagctaag agt                                          23

<210> SEQ ID NO 41
<211> LENGTH: 20
<212> TYPE: DNA
<213> ORGANISM: Artificial
<220> FEATURE:
<223> OTHER INFORMATION: Exon 2-3 forward FGA

<400> SEQUENCE: 41
cctcttctgg ctaacattgc                                              20

<210> SEQ ID NO 42
<211> LENGTH: 23
<212> TYPE: DNA
<213> ORGANISM: Artificial
<220> FEATURE:
<223> OTHER INFORMATION: Exon 2-3 backward FGA

<400> SEQUENCE: 42
cagggatatt atgaaggtat gtg                                          23

<210> SEQ ID NO 43
<211> LENGTH: 22
<212> TYPE: DNA
<213> ORGANISM: Artificial
<220> FEATURE:
<223> OTHER INFORMATION: Exon 4 forward FGA

<400> SEQUENCE: 43
ctcagcagct acttcaataa cc                                           22

<210> SEQ ID NO 44
<211> LENGTH: 20
<212> TYPE: DNA
<213> ORGANISM: Artificial
<220> FEATURE:
<223> OTHER INFORMATION: Exon 4 backward FGA

<400> SEQUENCE: 44
gtgcataact atcgccttcc                                              20

<210> SEQ ID NO 45
<211> LENGTH: 22
<212> TYPE: DNA
<213> ORGANISM: Artificial
<220> FEATURE:
<223> OTHER INFORMATION: Exon 5-1 forward FGA

<400> SEQUENCE: 45
ctcagcagct acttcaataa cc                                           22

<210> SEQ ID NO 46
```

```
<211> LENGTH: 19
<212> TYPE: DNA
<213> ORGANISM: Artificial
<220> FEATURE:
<223> OTHER INFORMATION: Exon 5-1 backward FGA

<400> SEQUENCE: 46
ttaatgcctt ccactctgg                                               19

<210> SEQ ID NO 47
<211> LENGTH: 18
<212> TYPE: DNA
<213> ORGANISM: Artificial
<220> FEATURE:
<223> OTHER INFORMATION: Exon 5-2 forward FGA

<400> SEQUENCE: 47
ccgatcttgt cgagggtc                                                18

<210> SEQ ID NO 48
<211> LENGTH: 21
<212> TYPE: DNA
<213> ORGANISM: Artificial
<220> FEATURE:
<223> OTHER INFORMATION: Exon 5-2 backward FGA

<400> SEQUENCE: 48
cataggtgag aagaaacctg g                                            21

<210> SEQ ID NO 49
<211> LENGTH: 20
<212> TYPE: DNA
<213> ORGANISM: Artificial
<220> FEATURE:
<223> OTHER INFORMATION: Exon 5-3 forward FGA

<400> SEQUENCE: 49
ctggacctct gagagctctg                                              20

<210> SEQ ID NO 50
<211> LENGTH: 22
<212> TYPE: DNA
<213> ORGANISM: Artificial
<220> FEATURE:
<223> OTHER INFORMATION: Exon 5-3 backward FGA

<400> SEQUENCE: 50
gacatggctc tgtactgtta gg                                           22

<210> SEQ ID NO 51
<211> LENGTH: 20
<212> TYPE: DNA
<213> ORGANISM: Artificial
<220> FEATURE:
<223> OTHER INFORMATION: Exon 6 forward FGA

<400> SEQUENCE: 51
ccgtgcctat ctttgtaaag                                              20

<210> SEQ ID NO 52
<211> LENGTH: 20
<212> TYPE: DNA
<213> ORGANISM: Artificial
<220> FEATURE:
<223> OTHER INFORMATION: Exon 6 backward FGA

<400> SEQUENCE: 52
```

```
aagacagagt gctcccattc                                               20

<210> SEQ ID NO 53
<211> LENGTH: 20
<212> TYPE: DNA
<213> ORGANISM: Artificial
<220> FEATURE:
<223> OTHER INFORMATION: 3'UTR forward FGA

<400> SEQUENCE: 53
gacccaatag gctgaagaag                                               20

<210> SEQ ID NO 54
<211> LENGTH: 19
<212> TYPE: DNA
<213> ORGANISM: Artificial
<220> FEATURE:
<223> OTHER INFORMATION: 3'UTR backward FGA

<400> SEQUENCE: 54
gggtggtata ctggattgc                                                19

<210> SEQ ID NO 55
<211> LENGTH: 18
<212> TYPE: DNA
<213> ORGANISM: Artificial
<220> FEATURE:
<223> OTHER INFORMATION: PR 1 forward FGB

<400> SEQUENCE: 55
gcatgctgga ttgaatcc                                                 18

<210> SEQ ID NO 56
<211> LENGTH: 21
<212> TYPE: DNA
<213> ORGANISM: Artificial
<220> FEATURE:
<223> OTHER INFORMATION: PR 1 backward FGB

<400> SEQUENCE: 56
ccagtcagta atccaaatcc c                                             21

<210> SEQ ID NO 57
<211> LENGTH: 22
<212> TYPE: DNA
<213> ORGANISM: Artificial
<220> FEATURE:
<223> OTHER INFORMATION: PR 2 forward FGB

<400> SEQUENCE: 57
caaaccctga taacctgcca tc                                            22

<210> SEQ ID NO 58
<211> LENGTH: 21
<212> TYPE: DNA
<213> ORGANISM: Artificial
<220> FEATURE:
<223> OTHER INFORMATION: PR 2 backward FGB

<400> SEQUENCE: 58
ggttcacttg ttggctgaac c                                             21

<210> SEQ ID NO 59
<211> LENGTH: 20
<212> TYPE: DNA
<213> ORGANISM: Artificial
<220> FEATURE:
```

<223> OTHER INFORMATION: Exon 1 forward FGB

<400> SEQUENCE: 59
gttcagccaa caagtgaacc                                                    20

<210> SEQ ID NO 60
<211> LENGTH: 22
<212> TYPE: DNA
<213> ORGANISM: Artificial
<220> FEATURE:
<223> OTHER INFORMATION: Exon 1 backward FGB

<400> SEQUENCE: 60
gctaagccat cctcatctta ag                                                 22

<210> SEQ ID NO 61
<211> LENGTH: 22
<212> TYPE: DNA
<213> ORGANISM: Artificial
<220> FEATURE:
<223> OTHER INFORMATION: Exon 2-3 forward FGB

<400> SEQUENCE: 61
gggtgttgga atagttacat tc                                                 22

<210> SEQ ID NO 62
<211> LENGTH: 19
<212> TYPE: DNA
<213> ORGANISM: Artificial
<220> FEATURE:
<223> OTHER INFORMATION: Exon 2-3 backward FGB

<400> SEQUENCE: 62
ttatctggca agttgcagg                                                     19

<210> SEQ ID NO 63
<211> LENGTH: 21
<212> TYPE: DNA
<213> ORGANISM: Artificial
<220> FEATURE:
<223> OTHER INFORMATION: Exon 4-5 forward FGB

<400> SEQUENCE: 63
aactgcttgg tgatagctca g                                                  21

<210> SEQ ID NO 64
<211> LENGTH: 20
<212> TYPE: DNA
<213> ORGANISM: Artificial
<220> FEATURE:
<223> OTHER INFORMATION: Exon 4-5 backward FGB

<400> SEQUENCE: 64
ccaaggtgct ggaattacag                                                    20

<210> SEQ ID NO 65
<211> LENGTH: 20
<212> TYPE: DNA
<213> ORGANISM: Artificial
<220> FEATURE:
<223> OTHER INFORMATION: Exon 6-7 forward FGB

<400> SEQUENCE: 65
aatggacagg ggattcagat                                                    20

<210> SEQ ID NO 66

```
<211> LENGTH: 20
<212> TYPE: DNA
<213> ORGANISM: Artificial
<220> FEATURE:
<223> OTHER INFORMATION: Exon 6-7 backward FGB

<400> SEQUENCE: 66
gaaatgcttt cgagtgatgc                                              20

<210> SEQ ID NO 67
<211> LENGTH: 20
<212> TYPE: DNA
<213> ORGANISM: Artificial
<220> FEATURE:
<223> OTHER INFORMATION: Exon 8 forward FGB

<400> SEQUENCE: 67
gactactgtg cacacgagtg                                              20

<210> SEQ ID NO 68
<211> LENGTH: 22
<212> TYPE: DNA
<213> ORGANISM: Artificial
<220> FEATURE:
<223> OTHER INFORMATION: Exon 8 backward FGB

<400> SEQUENCE: 68
gtctgcttga gagttttaga gg                                           22

<210> SEQ ID NO 69
<211> LENGTH: 20
<212> TYPE: DNA
<213> ORGANISM: Artificial
<220> FEATURE:
<223> OTHER INFORMATION: 3'UTR forward FGB

<400> SEQUENCE: 69
ccttcttccc acagcaatag                                              20

<210> SEQ ID NO 70
<211> LENGTH: 20
<212> TYPE: DNA
<213> ORGANISM: Artificial
<220> FEATURE:
<223> OTHER INFORMATION: 3'UTR backward FGB

<400> SEQUENCE: 70
gaggttgtga acgcttctcc                                              20

<210> SEQ ID NO 71
<211> LENGTH: 20
<212> TYPE: PRT
<213> ORGANISM: Homo sapiens

<400> SEQUENCE: 71

Val Arg Pro Glu His Pro Ala Glu Thr Glu Tyr Asp Ser Leu Tyr Pro
 1               5                  10                  15

Glu Asp Asp Leu
            20

<210> SEQ ID NO 72
<211> LENGTH: 30
<212> TYPE: DNA
<213> ORGANISM: Artificial
<220> FEATURE:
<223> OTHER INFORMATION: Forward primer
```

<400> SEQUENCE: 72
acatgcattt caataaacct tttgtttcct                                       30

<210> SEQ ID NO 73
<211> LENGTH: 24
<212> TYPE: DNA
<213> ORGANISM: Artificial
<220> FEATURE:
<223> OTHER INFORMATION: Reverse primer

<400> SEQUENCE: 73
ggtaaattgg caaaaagtgg tggt                                             24

<210> SEQ ID NO 74
<211> LENGTH: 24
<212> TYPE: DNA
<213> ORGANISM: Artificial
<220> FEATURE:
<223> OTHER INFORMATION: Probe 1

<400> SEQUENCE: 74
ttttaatggt caataaaggt acca                                             24

<210> SEQ ID NO 75
<211> LENGTH: 19
<212> TYPE: DNA
<213> ORGANISM: Artificial
<220> FEATURE:
<223> OTHER INFORMATION: Probe 2

<400> SEQUENCE: 75
atggtcaata aagatacca                                                   19

<210> SEQ ID NO 76
<211> LENGTH: 10168
<212> TYPE: DNA
<213> ORGANISM: Homo sapiens

<400> SEQUENCE: 76
cttcttcaca gaggcaactg attcaagtca ttacatagtt attgagtgtt aactacaact      60
atgttaagta cagctatata tgttagatgc cgtagccaca gaaatcagtt tacaatctaa     120
tgcagtggtt acagcatgta tacatataat ataaggttgc tacaaatgct atctgaggta     180
gagctgtttg aaagaatact aatacttaaa tgtttaattc aactgacttg attgacaact     240
gattagctga gtggaaaaga tggatgagaa agattgtgag acttaattgg ctggtggtat     300
ggtgatatga ttgacaataa ctgctaagtc agagagggat atattaagga ggagaagaaa     360
agcaacaaat ctggttttga tgtgttcact ttgttataat tattgattat ttactgaata     420
tgaatattta tctttgtttt tgagtcaata aatatacctt tgtaaagaca gaattaaagt     480
attagtattt ctttcaaact ggaggcattt ctcccactaa catatttcat caaaacttat     540
aataagcttg gttccagagg aagaaatgag ggataaccaa aaatagagac attaataata     600
gtgtaacgcc cagtgataaa tctcaatagg cagtgatgac agacatgttt tcccaaacac     660
aaggatgctg taagggccaa acagaaatga tggcccctcc ccagcacctc attttgcccc     720
ttccttcagc tatgcctcta ctctccttag atacaaggga ggtggatttt tctcttctct     780
gagatagctt gatggaacca caggaacaat gaagtgggct cctggctctt ttctctgtgg     840
cagatggggt gccatgccca ccttcagaca aagggaagat tgagctcaaa agctccctga     900
gaagtgagag cctatgaaca tggttgacac agagggacag gaatgtattt ccagggtcat     960

```
tcattcctgg gaatagtgaa ctgggacatg ggggaagtca gtctcctcct gccacagcca   1020
cagattaaaa ataataatgt taactgatcc ctaggctaaa ataatagtgt taactgatcc   1080
ctaagctaag aaagttcttt tggtaattca ggtgatggca gcaggaccca tcttaaggat   1140
agactaggtt tgcttagttc gaggtcatat ctgtttgctc tcagccatgt actggaagaa   1200
gttgcatcac acagcctcca ggactgccct cctcctcaca gcaatggata atgcttcact   1260
agcctttgca gataattttg gatcagagaa aaaaccttga gctgggccaa aaaggaggag   1320
cttcaacctg tgtgcaaaat ctgggaacct gacagtatag gttgggggcc aggatgagga   1380
aaaaggaacg ggaaagacct gcccacccct ctggtaagga ggcccgtga tcagctccag    1440 ccatttgcag tcctggctat cccaggagct tacataaagg gacaattgga gcctgagagg   1500
tgacagtgct gacactacaa ggctcggagc tccgggcact cagacatcat gagttggtcc   1560
ttgcaccccc ggaatttaat tctctacttc tatgctcttt tatttctctc ttcaacatgt   1620
gtagcagtaa gtgtgctctt cacaaaacgt tgtttaaaat ggaaagctgg aaaataaaac   1680
agataataaa ctagtgaaat ttctgtattt tttctctttt agtatgttgc taccagagac   1740
aactgctgca tcttagatga agattcgta agtagttttt atgtttctcc ctttgtgtgt    1800
gaactggaga ggggcagagg aatagaaata attccctcat aaatatcatc tggcacttgt   1860 aacttttaa aaacatagtc taggttttac ctattttct taatagattt taagagtagc     1920
atctgtctac attttaatc actgttatat tttcaggta gttattgtcc aactacctgt     1980
ggcattgcag atttcctgtc tacttatcaa accaaagtag acaaggatct acagtctttg   2040
gaagacatct tacatcaagt tgaaaacaaa acatcagaag tcaaacagct gataaaagca   2100
atccaactca cttataatcc tgatgaatca tcaaaaccaa gtgagaaaat aaagactact   2160
gaccaaaaaa taataataat aatctgtgaa gttcttttgc tgttgttta gttgttctat    2220 ttgcttaagg atttttatgt ctctgatcct atattacaga tatgatagac gctgctactt   2280
tgaagtccag gaaaatgtta aagaaaatta tgaaatatga agcatcgatt ttaacacatg   2340
actcaagtat tcggtaagga ttttgtttt aatttgctct gcaagactga tttagttttt    2400
atttaatatt ctatacttga gtgaaagtaa tttttaatgt gttttcccca tttataatat   2460
cccagtgaca ttatgcctga ttatgttgag catagtagag atagaagttt ttagtgcaat   2520
ataaattata ctgggttata attgcttatt aataatcaca ttgaagaaag atgttctaga   2580
tgtcttcaaa tgctagtttg accatattta tcaaaaattt tttccccatc ccccatttat   2640
cttacaacat aaaatcaatc tcataggaat ttgggtgttg aaaataaaat cctctttata   2700
aaaatgctga caaattggtg gttaaaaaaa ttagcaagca gaggcatagt aaggattttg   2760
gctcctaaag taaattatat tgaatgtgga gcaggaagaa acatgtcttg agagactaag   2820
tgtggcaaat attgcaaagc tcatattgat cattgcagaa tgaacctgca tagtctcttc   2880
ccttcatttg gaagtgaatg tctctgttaa agcttctcag ggactcataa actttctgaa   2940
cataaggtct cagatacagt tttaatattt ttccccaatt tttttttctg aattttctc    3000 aaagcagctt gagaaattga gataaatagt agctagggag aagtggccca ggaaagattt   3060
ctcctctttt tgctatcaga gggcccttgt tattattgtt attattatta cttgcattat   3120
tattgtccat cattgaagtt gaaggaggtt attgtacaga aattgcctaa gacaaggtag   3180
agggaaaacg tggacaaata gtttgtctac ccttttttac ttcaaagaaa gaacggttta   3240
tgcattgtag acagttttct atcatttttt gatatttgca agccaccctg taagtaacta   3300
caaaaggagg gttttttactt cccccagtcc attcccaaag ctatgtaacc agaagcatta   3360
```

```
aagaagaaag gggaagtatc tgttgtttta ttttacatac aataacgttc cagatcatgt   3420
ccctgtgtaa gttatatttt agattgaagc ttatatgtat agcctcagta gatccacaag   3480
tgaaaggtat actccttcag cacatgtgaa ttactgaact gagcttttcc tgcttctaaa   3540
gcatcagggg gtgttcctat taaccagtct cgccactctt gcaggttgct atctgctgtc   3600
ccttatgcat aaagtaaaaa gcaaaatgtc aatgacattt gcttattgac aaggactttg   3660
ttatttgtgt tgggagttga gacaatatgc cccattctaa gtaaaaagat tcaggtccac   3720
attgtattcc tgttttaatt gattttttga tttgttttc ttttcaaaa agtttataat    3780 tttaattcat gttaatttag taatataatt ttacattttc ctcaagaatg gaataattta   3840
tcagaaagca cttcttaaga aaatacttag cagtttccaa agaaaatata aaattactct   3900
tctgaaagga atacttattt ttgtcttctt atttttgtta tcttatgttt ctgtttgtag   3960
atatttgcag gaaatatata attcaaataa tcaaaagatt gttaacctga agagaaggt    4020 agcccagctt gaagcacagt gccaggaacc ttgcaaagac acggtgcaaa tccatgatat   4080
cactgggaaa ggtaactgat gaaggttata ttgggattag gttcatcaaa gtaagtaatg   4140
taaaggagaa agtatgtact ggaaagtata ggaatagttt agaaagtggc tacccattaa   4200
gtctaagaat ttcagttgtc tagacctttc ttgaatagct aaaaaaaaca gtttaaaagg   4260
aatgctgatg tgaaaagtaa gaaaattatt cttggaaaat gaatagttta ctacatgtta   4320
aaagctattt ttcaaggctg gcacagtctt acctgcattt caaaccacag taaaagtcga   4380
ttctccttct ctagattgtc aagacattgc caataaggga gctaaacaga gcgggcttta   4440
ctttattaaa cctctgaaag ctaaccagca attcttagtc tactgtgaaa tcgatgggtc   4500
tggaaatgga tggactgtgt ttcagaaggt aattttttcc ccaccatgtg tatttaataa   4560
attcctacat tgtttctgcc atatggcaga tacttttcta agcaccttgt gaaccgtagc   4620
tcatttaatc cttgcaatag ccctaagagg aaggtacttc tgttactcct atttacagaa   4680
aaggaaactg aggcacacaa ggttaaataa cttgcccaag accacataac taataagcaa   4740
cagagtcagc atttgaacct aggcagtata gtttcagagt ttgtgacttg actctatatt   4800
gtactggcac tgactttgta gattcatggt ggcacataat catagtacca cagtgacaaa   4860 taaaagaag gaaactcttt tgtcaggtag gtcaagacct gaggtttccc atcacaagat    4920
gaggaagccc aacaccaccc cccaccaccc caccaccatc accacccttt cacacaccag   4980
aggatacact tgggctgctc caagacaagg aacctgtgtt gcatctgcca cttgctgata   5040
cccactagga atcttggctc ctttactttc tgtttacctc ccaccactgt tataactgtt   5100
tctacagggg gcgctcagag ggaatgaatg gtggaagcat tagttgccag acaccgattg   5160
agcaatgggt tccatcataa gtgtaagaat cagtaatatc cagctagagt tctgaagtcg   5220
tctaggtgtc tttttaatat taccactcat ttagaattta tgatgtgcca gaaaccctct   5280
taagtatttc tcttatattc tctctcatga tccttgcagc aacccctaaga agtaaccatc   5340 attttttccta tttgatacat gaggaaactg aggtagcttg gccaagatca cttagttggg   5400
agttgataga accagtgctc tgtattttg acaaaatgtt gacagcattc tctttacatg    5460
cattgatagt ctatttttctc ctttttgctct tgcaaatgtg taattagaga cttgatggca   5520
gtgtagattc caagaaaaac tggattcaat ataagaagg atttggacat ctgtctccta    5580
ctggcacaac agaatttgg ctgggaaatg agaagattca tttgataagc acacagtctg    5640
ccatcccata tgcattaaga gtggaactgg aagactggaa tggcagaacc aggtactgtt   5700
ttgaaatgac ttccaacttt ttattgtaaa gattgcctgg aatgtgcact ttccaactat   5760
```

-continued

```
caatagacaa tggcaaatgc agcctgacaa atgcaaacag cacatccagc caccattttc    5820
tccaggagtc tgtttggttc ttgggcaatc caaaaaggta aattctattc aggatgaatc    5880
taagtgtatt ggtacaatct aattaccctg gaaccattca gagtaatagc taattactga    5940
acttttaatc agtcccagga attgagcata aaattataat tttatctagt ctaaattact    6000
atttcatgaa gcaggtatta ttattaatcc cattttatag attaacttgc tcaaagtcac    6060
attgctgata agtggtagag gtagaattca gactcaagta gtttaacttt agagcctgtc    6120
ctcttaacaa ctatcctggt tgaaaagcaa atacagcctc ttcagacttc tcagtgcctt    6180
gatggccatt tattctgtca aatcatgagc taccctaaaa gtaaaccagc tagctctttt    6240
gatgatctag aggcttcttt ttgcttgaga tatttgaagg ttttaagcat tgttacctaa    6300
ttaaaatgca gaaaaatatc caaccctctt gttatgttta aggaatagtg aaatatattg    6360
tcttcaaaca catggacttt tttttattgc ttggttggtt tttaatccag aaagtgctat    6420
agtcagtaga ccttcttcta ggaaaggacc ttccatttcc cagccactgg agattagaaa    6480
ataagctaaa tattttctgg aaatttctgt tcattcatta aggcccatcc tttcccccac    6540
tctatagaag tgttgtccac ttgcacaatt ttttccagga aagaatctct ctaactcctt    6600
cagctcacat gctttggacc acacagggaa gactttgatt gtgtaatgcc ctcagaagct    6660
ctccttcttg ccactaccac actgatttga ggaagaaaat ccctttagca cctaaccctt    6720
caggtgctat gagtggctaa tggaactgta cctccttcaa gttttgtgca ataattaagg    6780
gtcactcact gtcagatact ttctgtgatc tatgataatg tgtgtgcaac acataacatt    6840
tcaataaaag tagaaaatat gaaattagag tcatctacac atctggattt gatcttagaa    6900
tgaaacaagc aaaaaagcat ccaagtgagt gcaattatta gttttcagag atgcttcaaa    6960
ggcttctagg cccatcccgg gaagtgttaa tgagctgtgg actggttcac atatctattg    7020
cctcttgcca gatttgcaaa aaacttcact caatgagcaa atttcagcct taagaaacaa    7080
agtcaaaaat tccaaggaag catcctacga aagagggaac ttctgagatc cctgaggagg    7140
gtcagcatgt gatggttgta tttccttctt ctcagtactg cagactatgc catgttcaag    7200
gtgggacctg aagctgacaa gtaccgccta acatatgcct acttcgctgg tggggatgct    7260
ggagatgcct ttgatggctt tgattttggc gatgatccta gtgacaagtt tttcacatcc    7320
cataatggca tgcagttcag tacctgggac aatgacaatg ataagtttga aggcaactgt    7380
gctgaacagg atggatctgg ttggtggatg aacaagtgtc acgctggcca tctcaatgga    7440
gtttattacc aaggtatgtt ttcctttctt agattccaag ttaatgtata gtgtatacta    7500
ttttcataaa aaataataaa tagatatgaa gaaatgaaga ataatttata aagatagtag    7560
ggattttatc atgttcttta tttcaactaa gttctttgaa actggaagtg gataatacca    7620
agttcatgcc taaaattagc ccttctaaag aaatccacct gctgcaaaat atccagtagt    7680
ttggcattat atgtgaaact atcaccatca tagctggcac tgtgggttgt gggatctcct    7740
ttagacatac aacataaatg atctggatgg attaacatta ctacatggat gcttgttgac    7800
acattaacct ggcttcccat gagctttgtg tcagatacac gcagtgaaca ggtgtttgga    7860
ggaacagaat aaaaagaagg caagcactgg taagggcagg ggtttgtgaa agcttgagag    7920
aagagaccag tctgaggaca gtagacactt attttaggat gggggttgga tgaggaggct    7980
atagtttgct ataagcttgg aatggtttgg aacactggtt tcactcacct acccagcagt    8040
tatgtgtggg gaagccttac cgatgctaaa ggatccatgt tacaataatg gcattatttg    8100
gaaatcccag tggtattcca tgaataaaac cactatgaag ataatcccac tcaacagact    8160
```

```
ctccgttgga gaaggacagc aacaccaccc tgggaaagcc aaacagtcag accagacctg      8220
tttagcatca gtaggacttc cctaccatat ctgctgggta gatgagtgaa accagtgttc      8280
caaaccactc cgggcttgta gcaaaccata gtctcctcat ctaccaagat gagcaacctt      8340
acctcctgat gtcctagcca atcaccaact aggaaacttt gcacagttta tttaaagtaa      8400
cagtttgatt ttcacaatat ttttaaattg gagaaacata acttatcttt gcactcacaa      8460
accacataat gagaagaaac tctaagggaa aatgcttgat ctgtgtgacc cggggcgcca      8520
tgccagagct gtagttcatg ccagtgttgt gctctgacaa gccttttaca gaattacatg      8580
agatctgctt ccctaggaca aggagaaggc aaatcaacag aggctgcact ttaaaatgga      8640
gacataaaat aacatgccag aaccatttcc taaagctcct caatcaacca acaaaattgt      8700
gctttcaaat aacctgagtt gacctcatca ggaattttgt ggctccttct cttctaacct      8760
gcctgaagaa agatggtcca cagcagctga gtccgggatg gataagctta gggacagagg      8820
ccaattaggg aactttgggt ttctagccct actagtagtg aataaattta agtgtggat      8880 gtgactatga gtcacagcac agatgttgtt taataatatg tttattttat aaattgatat      8940
tttaggaatc tttggagata ttttcagtta gcagataata ctataaattt tatgtaactg      9000
gcaatgcact tcgtaataga cagctcttca tagacttgca gaggtaaaaa gattccagaa      9060
taatgatatg tacatctacg acttgtttta ggtggcactt actcaaaagc atctactcct      9120
aatggttatg ataatggcat tatttgggcc acttggaaaa cccggtggta ttccatgaag      9180
aaaaccacta tgaagataat cccattcaac agactcacaa ttggagaagg acagcaacac      9240
cacctggggg gagccaaaca ggtcagacca gagcaccctg cggaaacaga atatgactca      9300
ctttaccctg aggatgattt gtagaaaatt aactgctaat ttctattgac ccacaaagtt      9360
tcagaaattc tctgaaagtt tcttcctttt ttctcttact atatttattg atttcaagtc      9420
ttctattaag gacatttagc cttcaatgga aattaaaact catttaggac tgtatttcca      9480
aattactgat atcagagtta tttaaaaatt gtttatttga ggagataaca tttcaacttt      9540
gttcctaaat atataataat aaaatgattg actttatttg cattttatg accacttgtc      9600 atttattttg tctttgtaaa ttatttcat tatatcaaat attttagtat gtacttaata      9660
aaataggaga acattttaga gtttcaaatt cccaggtatt ttccttgttt attaccccta      9720
aatcattcct atttaattct tcttttttaaa tggagaaaat tatgtctttt taatatggtt      9780
tttgttttgt tatatattca caggctggag acgtttaaaa gaccgtttca aaagagattt      9840
acttttttaa aggactttat ctgaacagag agatataata ttttttcctat tggacaatgg      9900 acttgcaaag cttcacttca ttttaagagc aaaagacccc atgttgaaaa ctccataaca      9960
gttttatgct gatgataatt tatctacatg catttcaata aaccttttgt ttcctaagac      10020
tagatacatg gtatctttat tgaccattaa aaaccaccac tttttgccaa tttaccaatt      10080
acaattgggc aaccatcagt agtaattgag tcctcatttt atgctaaatg ttatgcctaa      10140
ctctttggga gttacaaagg aaatagca                                        10168

<210> SEQ ID NO 77
<211> LENGTH: 10168
<212> TYPE: DNA
<213> ORGANISM: Homo sapiens

<400> SEQUENCE: 77
cttcttcaca gaggcaactg attcaagtca ttacatagtt attgagtgtt aactacaact        60
atgttaagta cagctatata tgttagatgc cgtagccaca gaaatcagtt tacaatctaa       120
```

```
tgcagtggat acagcatgta tacatataat ataaggttgc tacaaatgct atctgaggta      180
gagctgtttg aaagaatact aatacttaaa tgtttaattc aactgacttg attgacaact      240
gattagctga gtggaaaaga tggatgagaa agattgtgag acttaattgg ctggtggtat      300
ggtgatatga ttgacaataa ctgctaagtc agagagggga atattaagga ggagaagaaa      360
agcaacaaat ctggttttga tgtgttcact tgttataat tattgattat ttactgaata       420
tgaatattta tctttgtttt tgagtcaata aatatacctt tgtaaagaca gaattaaagt      480
attagtattt ctttcaaact ggaggcattt ctcccactaa catatttcat caaaacttat      540
aataagcttg gttccagagg aagaaatgag ggataaccaa aaatagagac attaataata     600
gtgtaacgcc cagtgataaa tctcaatagg cagtgatgac agacatgttt cccaaacac      660 aaggatgctg taagggccaa acagaaatga tggcccctcc ccagcacctc attttgcccc      720
ttccttcagc tatgcctcta ctctccttag atacaaggga ggtggatttt tctcttctct      780
gagatagctt gatggaacca caggaacaat gaagtgggct cctggctctt ttctctgtgg     840
cagatggggt gccatgccca ccttcagaca aagggaagat tgagctcaaa agctccctga     900
gaagtgagag cctatgaaca tggttgacac agagggacag gaatgtattt ccagggtcat    960
tcattcctgg gaatagtgaa ctgggacatg ggggaagtca gtctcctcct gccacagcca   1020
cagattaaaa ataataatgt taactgatcc ctaggctaaa ataatagtgt taactgatcc   1080
ctaagctaag aaagttcttt tggtaattca ggtgatggca gcaggaccca tcttaaggat   1140
agactaggtt tgcttagttc gaggtcatat ctgtttgctc tcagccatgt actggaagaa   1200
gttgcatcac acagcctcca ggactgccct cctcctcaca gcaatggata atgcttcact   1260
agcctttgca gataattttg gatcagagaa aaaaccttga gctgggccaa aaaggaggag   1320
cttcaacctg tgtgcaaaat ctgggaacct gacagtatag gttgggggcc aggatgagga   1380
aaaaggaacg ggaaagacct gcccaccctt ctggtaagga ggcccgtga tcagctccag    1440 ccatttgcag tcctggctat cccaggagct tacataaagg gacaattgga gcctgagagg   1500
tgacagtgct gacactacaa ggctcggagc tccgggcact cagacatcat gagttggtcc   1560
ttgcaccccc ggaattaat tctctacttc tatgctcttt tatttctctc ttcaacatgt    1620
gtagcagtaa gtgtgctctt cacaaaacgt tgtttaaaat ggaaagctgg aaaataaaac   1680
agataataaa ctagtgaaat ttctgtattt tttctctttt agtatgttgc taccagagac   1740
aactgctgca tcttagatga aagattcgta agtagttttt atgtttctcc ctttgtgtgt   1800
gaactggaga ggggcagagg aatagaaata attccctcat aaatatcatc tggcacttgt   1860 aacttttttaa aaacatagtc taggttttac ctattttct taatagattt taagagtagc   1920
atctgtctac attttaatc actgttatat tttcagggta gttattgtcc aactacctgt    1980
ggcattgcag atttcctgtc tacttatcaa accaaagtag acaaggatct acagtctttg    2040
gaagacatct tacatcaagt tgaaaacaaa acatcagaag tcaaacagct gataaaagca   2100
atccaactca cttataatcc tgatgaatca tcaaaaccaa gtgagaaaat aaagactact   2160
gaccaaaaaa taataataat aatctgtgaa gttcttttgc tgttgttta gttgttctat    2220 ttgcttaagg atttttatgt ctctgatcct atattacaga tatgatagac gctgctactt   2280
tgaagtccag gaaatgttta gaagaaatta tgaaatatga agcatcgatt ttaacacatg   2340
actcaagtat tcggtaagga tttttgtttt aatttgctct gcaagactga tttagttttt    2400
atttaatatt ctatacttga gtgaaagtaa tttttaatgt gttttcccca tttataatat   2460
cccagtgaca ttatgcctga ttatgttgag catagtagag atagaagttt ttagtgcaat   2520
```

-continued

```
ataaattata ctgggttata attgcttatt aataatcaca ttgaagaaag atgttctaga    2580
tgtcttcaaa tgctagtttg accatattta tcaaaaattt tttccccatc ccccatttat    2640
cttacaacat aaaatcaatc tcataggaat ttgggtgttg aaaataaaat cctctttata    2700
aaaatgctga caaattggtg gttaaaaaaa ttagcaagca gaggcatagt aaggattttg    2760
gctcctaaag taaattatat tgaatgtgga gcaggaagaa acatgtcttg agagactaag    2820
tgtggcaaat attgcaaagc tcatattgat cattgcagaa tgaacctgca tagtctcttc    2880
ccttcatttg gaagtgaatg tctctgttaa agcttctcag ggactcataa actttctgaa    2940
cataaggtct cagatacagt tttaatattt ttccccaatt ttttttttctg aattttttctc    3000 aaagcagctt gagaaattga gataaatagt agctagggag aagtggccca ggaaagattt    3060 ctcctcttt tgctatcaga gggcccttgt tattattgtt attattatta cttgcattat    3120
tattgtccat cattgaagtt gaaggaggtt attgtacaga aattgcctaa gacaaggtag    3180
agggaaaacg tggacaaata gtttgtctac cctttttac ttcaaagaaa gaacggttta    3240
tgcattgtag acagttttct atcattttg gatatttgca agccaccctg taagtaacta    3300
caaaaggagg gttttactt cccccagtcc attcccaaag ctatgtaacc agaagcatta    3360
aagaagaaag gggaagtatc tgttgttta ttttacatac aataacgttc cagatcatgt    3420
ccctgtgtaa gttatatttt agattgaagc ttatatgtat agcctcagta gatccacaag    3480
tgaaaggtat actccttcag cacatgtgaa ttactgaact gagcttttcc tgcttctaaa    3540
gcatcagggg gtgttcctat taaccagtct cgccactctt gcaggttgct atctgctgtc    3600
ccttatgcat aaagtaaaaa gcaaaatgtc aatgacattt gcttattgac aaggactttg    3660
ttatttgtgt tgggagttga gacaatatgc cccattctaa gtaaaaagat tcaggtccac    3720
attgtattcc tgttttaatt gattttttga tttgtttttc tttttcaaaa agtttataat    3780
tttaattcat gttaatttag taatataatt ttacattttc ctcaagaatg gaataattta    3840
tcagaaagca cttcttaaga aaatacttag cagtttccaa agaaaatata aaattactct    3900
tctgaaagga atacttattt ttgtcttctt attttttgtta tcttatgttt ctgtttgtag    3960
atatttgcag gaaatatata attcaaataa tcaaaagatt gttaacctga agagaaggt    4020 agcccagctt gaagcacagt gccaggaacc ttgcaaagac acggtgcaaa tccatgatat    4080
cactgggaaa ggtaactgat gaaggttata ttgggattag gttcatcaaa gtaagtaatg    4140
taaaggagaa agtatgtact ggaaagtata ggaatagttt agaaagtggc tacccattaa    4200
gtctaagaat ttcagttgtc tagacctttc ttgaatagct aaaaaaaaca gtttaaaagg    4260
aatgctgatg tgaaaagtaa gaaaattatt cttggaaaat gaatagttta ctacatgtta    4320 aaagctatt ttcaaggctg gcacagtctt acctgcattt caaaccacag taaaagtcga    4380
ttctccttct ctagattgtc aagacattgc caataaggga gctaaacaga gcgggcttta    4440
ctttattaaa cctctgaaag ctaaccagca attcttagtc tactgtgaaa tcgatgggtc    4500
tggaaatgga tggactgtgt tcagaaggt aattttttcc ccaccatgtg tatttaataa    4560
attcctacat tgtttctgcc atatggcaga tactttctca agcaccttgt gaaccgtagc    4620
tcatttaatc cttgcaatag ccctaagagg aaggtacttc tgttactcct atttacagaa    4680
aaggaaactg aggcacacaa ggttaaataa cttgcccaag accacataac taataagcaa    4740
cagagtcagc atttgaacct aggcagtata gtttcagagt ttgtgacttg actctatatt    4800
gtactggcac tgactttgta gattcatggt ggcacataat catagtacca cagtgacaaa    4860
taaaaagaag gaaactcttt tgtcaggtag gtcaagacct gaggtttccc atcacaagat    4920
```

-continued

| | |
|---|---|
| gaggaagccc aacaccaccc cccaccaccc caccaccatc accacccttt cacacaccag | 4980 |
| aggatacact tgggctgctc caagacaagg aacctgtgtt gcatctgcca cttgctgata | 5040 |
| cccactagga atcttggctc ctttactttc tgtttacctc ccaccactgt tataactgtt | 5100 |
| tctacagggg gcgctcagag ggaatgaatg gtggaagcat tagttgccag acaccgattg | 5160 |
| agcaatgggt tccatcataa gtgtaagaat cagtaatatc cagctagagt tctgaagtcg | 5220 |
| tctaggtgtc ttttttaatat taccactcat ttagaattta tgatgtgcca gaaaccctct | 5280 |
| taagtatttc tcttatattc tctctcatga tccttgcagc aaccctaaga agtaaccatc | 5340 |
| atttttccta tttgatacat gaggaaactg aggtagcttg gccaagatca cttagttggg | 5400 |
| agttgataga accagtgctc tgtattttg acaaaatgtt gacagcattc tctttacatg | 5460 |
| cattgatagt ctattttctc cttttgctct tgcaaatgtg taattagaga cttgatggca | 5520 |
| gtgtagattt caagaaaaac tggattcaat ataagaagg atttggacat ctgtctccta | 5580 |
| ctggcacaac agaattttgg ctgggaaatg agaagattca tttgataagc acacagtctg | 5640 |
| ccatcccata tgcattaaga gtggaactgg aagactggaa tggcagaacc aggtactgtt | 5700 |
| ttgaaatgac ttccaacttt ttattgtaaa gattgcctgg aatgtgcact ttccaactat | 5760 |
| caatagacaa tggcaaatgc agcctgacaa atgcaaacag cacatccagc caccattttc | 5820 |
| tccaggagtc tgtttggttc ttgggcaatc caaaaggta aattctattc aggatgaatc | 5880 |
| taagtgtatt ggtacaatct aattaccctg gaaccattca gagtaatagc taattactga | 5940 |
| acttttaatc agtcccagga attgagcata aaattataat tttatctagt ctaaattact | 6000 |
| atttcatgaa gcaggtatta ttattaatcc cattttatag attaacttgc tcaaagtcac | 6060 |
| attgctgata agtggtagag gtagaattca gactcaagta gtttaacttt agagcctgtc | 6120 |
| ctcttaacaa ctatcctggt tgaaaagcaa atacagcctc ttcagacttc tcagtgcctt | 6180 |
| gatggccatt tattctgtca aatcatgagc taccctaaaa gtaaaccagc tagctctttt | 6240 |
| gatgatctag aggcttcttt ttgcttgaga tatttgaagg ttttaagcat tgttacctaa | 6300 |
| ttaaaatgca gaaaaatatc caaccctctt gttatgttta aggaatagtg aaatatattg | 6360 |
| tcttcaaaca catggacttt ttttttattgc ttggttggtt tttaatccag aaagtgctat | 6420 |
| agtcagtaga ccttcttcta ggaaaggacc ttccatttcc cagccactgg agattagaaa | 6480 |
| ataagctaaa tattttctgg aaatttctgt tcattcatta aggcccatcc tttcccccac | 6540 |
| tctatagaag tgttgtccac ttgcacaatt ttttccagga aagaatctct ctaactcctt | 6600 |
| cagctcacat gctttggacc acacagggaa gactttgatt gtgtaatgcc ctcagaagct | 6660 |
| ctccttcttg ccactaccac actgatttga ggaagaaaat ccctttagca cctaacccttt | 6720 |
| caggtgctat gagtggctaa tggaactgta cctccttcaa gttttgtgca ataattaagg | 6780 |
| gtcactcact gtcagatact ttctgtgatc tatgataatg tgtgtgcaac acataacatt | 6840 |
| tcaataaaag tagaaaatat gaaattagag tcatctacac atctggattt gatcttagaa | 6900 |
| tgaaacaagc aaaaaagcat ccaagtgagt gcaattatta gttttcagag atgcttcaaa | 6960 |
| ggcttctagg cccatcccgg gaagtgttaa tgagctgtgg actggttcac atatctattg | 7020 |
| cctcttgcca gatttgcaaa aaacttcact caatgagcaa atttcagcct taagaaacaa | 7080 |
| agtcaaaaat tccaaggaag catcctacga aagagggaac ttctgagatc cctgaggagg | 7140 |
| gtcagcatgt gatggttgta tttccttctt ctcagtactg cagactatgc catgttcaag | 7200 |
| gtgggacctg aagctgacaa gtaccgccta acatatgcct acttcgctgg tggggatgct | 7260 |
| ggagatgcct tgatggcttt tgattttggc gatgatccta gtgacaagtt tttcacatcc | 7320 |

```
cataatggca tgcagttcag tacctgggac aatgacaatg ataagtttga aggcaactgt    7380
gctgaacagg atggatctgg ttggtggatg aacaagtgtc acgctggcca tctcaatgga    7440
gtttattacc aaggtatgtt ttcctttctt agattccaag ttaatgtata gtgtatacta    7500
ttttcataaa aaataataaa tagatatgaa gaaatgaaga ataatttata agatagtag     7560
ggatttttatc atgttcttta tttcaactaa gttcttgaa actggaagtg gataatacca    7620
agttcatgcc taaaattagc ccttctaaag aaatccacct gctgcaaaat atccagtagt    7680
ttggcattat atgtgaaact atcaccatca tagctggcac tgtgggttgt gggatctcct    7740
ttagacatac aacataaatg atctggatgg attaacatta ctacatggat gcttgttgac    7800
acattaacct ggcttcccat gagctttgtg tcagatacac gcagtgaaca ggtgtttgga    7860
ggaacagaat aaagagaagg caagcactgg taagggcagg ggtttgtgaa agcttgagag    7920
aagagaccag tctgaggaca gtagacactt attttaggat gggggttgga tgaggaggct    7980
atagtttgct ataagcttgg aatggttgg aacactggtt tcactcacct acccagcagt     8040
tatgtgtggg gaagccttac cgatgctaaa ggatccatgt tacaataatg gcattatttg    8100
gaaatcccag tggtattcca tgaataaaac cactatgaag ataatcccac tcaacagact    8160
ctccgttgga gaaggacagc aacaccaccc tgggaaagcc aaacagtcag accagacctg    8220
tttagcatca gtaggacttc cctaccatat ctgctgggta gatgagtgaa accagtgttc    8280
caaaccactc cgggcttgta gcaaaccata gtctcctcat ctaccaagat gagcaacctt    8340
acctcctgat gtcctagcca atcaccaact aggaaacttt gcacagttta tttaaagtaa    8400
cagtttgatt ttcacaatat ttttaaattg gagaaacata acttatcttt gcactcacaa    8460
accacataat gagaagaaac tctaagggaa aatgcttgat ctgtgtgacc cggggcgcca    8520
tgccagagct gtagttcatg ccagtgttgt gctctgacaa gccttttaca gaattacatg    8580
agatctgctt ccctaggaca aggagaaggc aaatcaacag aggctgcact ttaaaatgga    8640
gacataaaat aacatgccag aaccatttcc taaagctcct caatcaacca acaaaattgt    8700
gctttcaaat aacctgagtt gacctcatca ggaattttgt ggctccttct cttctaacct    8760
gcctgaagaa agatggtcca cagcagctga gtccgggatg gataagctta gggacagagg    8820
ccaattaggg aactttgggt ttctagccct actagtagtg aataaattta agtgtggat     8880
gtgactatga gtcacagcac agatgttgtt taataatatg tttattttat aaattgatat    8940
tttaggaatc tttggagata ttttcagtta gcagataata ctataaattt tatgtaactg    9000
gcaatgcact tcgtaataga cagctcttca tagacttgca gaggtaaaaa gattccagaa    9060
taatgatatg tacatctacg acttgtttta ggtggcactt actcaaaagc atctactcct    9120
aatggttatg ataatggcat tatttgggcc acttggaaaa cccggtggta ttccatgaag    9180
aaaaccacta tgaagataat cccattcaac agactcacaa ttggagaagg acagcaacac    9240
cacctggggg gagccaaaca ggtcagacca gagcaccctg cggaaacaga atatgactca    9300
ctttaccctg aggatgattt gtagaaaatt aactgctaat ttctattgac ccacaaagtt    9360
tcagaaattc tctgaaagtt tcttcctttt ttctcttact atatttattg atttcaagtc    9420
ttctattaag gacatttagc cttcaatgga aattaaaact catttaggac tgtatttcca    9480
aattactgat atcagagtta tttaaaaatt gtttatttga ggagtaaaca tttcaacttt    9540
gttcctaaat atataataat aaaatgattg actttatttg cattttatg accacttgtc     9600
atttattttg tcttcgtaaa ttattttcat tatatcaaat attttagtat gtacttaata    9660
aaataggaga acatttttaga gtttcaaatt cccaggtatt ttccttgttt attacccta    9720
```

```
aatcattcct atttaattct tcttttttaaa tggagaaaat tatgtctttt taatatggtt    9780
tttgttttgt tatatattca caggctggag acgtttaaaa gaccgtttca aaagagattt    9840
acttttttaa aggactttat ctgaacagag agatataata ttttcctat tggacaatgg    9900 acttgcaaag cttcacttca ttttaagagc aaaagacccc atgttgaaaa ctccataaca    9960
gttttatgct gatgataatt tatctacatg catttcaata aaccttttgt ttcctaagac   10020
tagatacatg gtaccttat tgaccattaa aaaccaccac tttttgccaa tttaccaatt    10080
acaattgggc aaccatcagt agtaattgag tcctcatttt atgctaaatg ttatgcctaa   10140
ctctttggga gttacaaagg aaatagca                                       10168
```

<210> SEQ ID NO 78
<211> LENGTH: 4
<212> TYPE: PRT
<213> ORGANISM: Homo sapiens

<400> SEQUENCE: 78

Ala Gly Asp Val
1

<210> SEQ ID NO 79
<211> LENGTH: 20
<212> TYPE: PRT
<213> ORGANISM: Homo sapiens

<400> SEQUENCE: 79

Val Arg Pro Glu His Pro Ala Glu Thr Glu Tyr Asp Ser Leu Tyr Pro
1               5                   10                  15

Glu Asp Asp Leu
            20

<210> SEQ ID NO 80
<211> LENGTH: 18
<212> TYPE: DNA
<213> ORGANISM: Artificial
<220> FEATURE:
<223> OTHER INFORMATION: Mini-gene construct sequence

<400> SEQUENCE: 80
ggtaccttta ttgaccat                                                      18

<210> SEQ ID NO 81
<211> LENGTH: 18
<212> TYPE: DNA
<213> ORGANISM: Artificial
<220> FEATURE:
<223> OTHER INFORMATION: CstF consensus sequence
<220> FEATURE:
<221> NAME/KEY: misc_feature
<222> LOCATION: (14)..(15)
<223> OTHER INFORMATION: n is a, c, g, or t

<400> SEQUENCE: 81
ygtgtyttya ytgnnygt                                                      18

<210> SEQ ID NO 82
<211> LENGTH: 18
<212> TYPE: DNA
<213> ORGANISM: Artificial
<220> FEATURE:
<223> OTHER INFORMATION: CstF mutant sequence

<400> SEQUENCE: 82
gataccttta ttgaccat                                                      18

<210> SEQ ID NO 83
<211> LENGTH: 18
<212> TYPE: DNA
<213> ORGANISM: Artificial
<220> FEATURE:
<223> OTHER INFORMATION: CstF mutant sequence

<400> SEQUENCE: 83
gataccttta ttaaccat                                                   18

<210> SEQ ID NO 84
<211> LENGTH: 18
<212> TYPE: DNA
<213> ORGANISM: Artificial
<220> FEATURE:
<223> OTHER INFORMATION: CstF mutant sequence

<400> SEQUENCE: 84
ggtgccttta ttgaccat                                                   18

<210> SEQ ID NO 85
<211> LENGTH: 18
<212> TYPE: DNA
<213> ORGANISM: Artificial
<220> FEATURE:
<223> OTHER INFORMATION: CstF mutant sequence

<400> SEQUENCE: 85
ggtgccttta ttgaccgt                                                   18

<210> SEQ ID NO 86
<211> LENGTH: 1074
<212> TYPE: DNA
<213> ORGANISM: Homo sapiens

<400> SEQUENCE: 86
ctagaccacc atgggtggca cttactcaaa agcatctact cctaatggtt atgataatgg     60
cattatttgg gccacttgga aaacccggtg gtattccatg aagaaaacca ctatgaagat    120
aatcccattc aacagactca caattggaga aggacagcaa caccacctgg ggggagccaa    180
acaggtcaga ccagagcacc ctgcggaaac agaatatgac tcactttacc ctgaggatga    240
tttgtagaaa attaactgct aatttctatt gacccacaaa gtttcagaaa ttctctgaaa    300
gtttcttcct tttttctctt actatattta ttgatttcaa gtcttctatt aaggacattt    360
agccttcaat ggaaattaaa actcatttag gactgtattt ccaaattact gatatcagag    420
ttatttaaaa attgtttatt tgaggagata acatttcaac tttgttccta aatatataat    480
aataaaatga ttgactttat ttgcattttt atgaccactt gtcatttatt ttgtcttcgt    540
aaattatttt cattatatca aatatttag tatgtactta ataaaatagg agaacatttt    600
agagtttcaa attcccaggt attttccttg tttattaccc ctaaatcatt cctatttaat    660
tcttcttttt aaatggagaa aattatgtct ttttaatatg gtttttgttt tgttatatat    720
tcacaggctg gagacgttta aaagaccgtt tcaaaagaga tttactttt taaaggactt    780
tatctgaaca gagagatata atattttttcc tattggacaa tggacttgca agcttcact    840
tcattttaag agcaaaagac cccatgttga aaactccata acagttttat gctgatgata    900
atttatctac atgcatttca ataaaccttt tgtttcctaa gactagatac atggtacctt    960

```
tattgaccat taaaaaccac cactttttgc caatttacca attacaattg ggcaaccatc    1020
agtagtaatt gagtcctcat tttatgctaa atgttatgcc taactctttg catt         1074
```

METHOD OF SCREENING FOR THE PRESENCE OF A GENETIC DEFECT ASSOCIATED WITH DEEP VENOUS THROMBOSIS

CROSS-REFERENCE TO RELATED APPLICATIONS

The present application is a 35 U.S.C. §371 national phase application of International PCT Application No. PCT/EP2006/003195, having an international filing date of Mar. 31, 2006, which claims priority to European Patent Application No. 05075764.0, filed Apr. 1, 2005, the disclosures of each of which are incorporated herein by reference in their entireties.

The present invention relates to a method of screening for the presence of a genetic defect associated with venous thrombosis, in particular deep venous thrombosis. The invention further relates to a diagnostic kit for use in the method.

Venous thrombosis (VT) is the obstruction of the circulation by clots that have been formed locally in the veins or have been released from a thrombus elsewhere (embolization). The usual sites of thrombus formation are the superficial and deep veins of the legs, but it also may occur in veins in the brain, retina, liver and mesentery. Major complications are the post-thrombotic syndrome and death from pulmonary embolism, which occur in 20-40% and 1-2% of patients, respectively. In developed countries the annual incidence of VT is about 1/1000.

Venous thrombosis is a multicausal disease. Besides well known acquired risk factors like immobilization, recent surgery or trauma, pregnancy and puerperium, and current use of oral contraceptives there are also several genetic risk factors for VT, like the factor V Leiden and the prothrombin 20210A mutation.

It is the object of the present invention to provide a screening method that enables determination of the presence of a genetic risk factor for venous thrombosis, in particular deep venous thrombosis, in an individual.

This object was solved by the identification of a fibrinogen γ haplotype (in the present context defined as a series of single nucleotide polymorphisms (SNPs) that inherit together) that is linked to a reduced plasma fibrinogen γ' level, a reduced fibrinogen γ'/total fibrinogen ratio (γ'/γ) and an increased risk of deep venous thrombosis (DVT).

Fibrinogen is an essential component of the haemostatic system, being the precursor of fibrin, the end product of the coagulation cascade. Fibrinogen is converted into fibrin through limited proteolysis by thrombin, which exposes polymerization sites on the fibrin monomers. These monomers spontaneously associate to form insoluble fibrin. Activated factor XIII-forms covalent bonds between adjacent fibrin monomers. These cross-links strengthen the fibrin clot and increase its resistance to degradation by the fibrinolytic system.

Fibrinogen, depicted in FIG. 1 by Fiona Green (http://www.well.ox.ac.uk/~fionag/fibrinogen.shtml), is a plasma glycoprotein with a molecular weight of 340 kDa, which is primarily synthesized by hepatocytes. It circulates in plasma at a concentration of approximately 9 μM (3 g/L). Fibrinogen molecules are elongated 45 nm structures with two outer D domains, connected by a coiled-coil segment to a central E-domain. They consist of two symmetric half molecules, each containing one set of three different polypeptide chains termed Aα, Bβ and γ. The three chains are encoded by three separate genes, encoding fibrinogen alpha (FGA), fibrinogen beta (FGB), and fibrinogen gamma (FGG), clustered in a region of approximately 50 kb on chromosome 4q31.3.

The FGG gene contains 10 exons and is oriented in tandem with the FGA gene, which contains 6 exons. They are transcribed in the opposite direction to the FGB gene, which is located downstream from the FGA gene and contains 8 exons.

Alternative splicing may occur in the FGA and FGG genes. The predominant Aα chain of circulating fibrinogen contains 610 amino acid residues, whereas the alternative Aα chain contains 846 amino acid residues. The Bβ chain consists of 461 amino acids. The most abundant form of the γ chain, γA, consists of 411 amino acid residues. The variant γ' (γB) chain contains 427 amino acid residues.

Abnormalities of fibrinogen are known to affect the risk of deep venous thrombosis (DVT). Koster et al. (Thromb. Haemost. 71: 719-722 (1994)) described that elevated levels of plasma fibrinogen (>5 g/L) increase the risk of DVT. The mechanism of this effect is not known. The fibrinogen concentration has a profound effect on fibrin clot structure in vitro experiments. The rate of fibrinopeptide A release increases with rising fibrinogen levels and this is associated with the formation of a more lysis-resistant and more dense and tight fibrin network (Blombäck, Thromb Res. 75: 327-328 (1994); Siebenlist & Mosesson, J Biol. Chem. 68:315-320 (1994)).

Another mechanism by which high fibrinogen levels may contribute to thrombosis risk is by increasing blood viscosity. In addition, genetic variants of fibrinogen (dysfibrinogenemias) have been found in patients with thrombosis and a prolonged thrombin time (reviewed by Mosesson (Semin. Thromb. Hemost. 25:311-319 (1999)); Hanss & Biot (Ann. N.Y. Acad. Sci., 936: 89-90 (2001))). The majority of these patients have a mutation in the FGA or FGG gene, although the precise relation between carriership of these mutations and venous thrombosis is poorly documented (Haverkate et al. Thromb. Haemost. 73:151-161 (1995)).

The present inventors thus hypothesized that relatively common variations in the fibrinogen genes might exist that influence the risk of venous thrombosis, in particular deep venous thrombosis. These variations may affect fibrinogen levels, the formation of the fibrin network structure or the sensitivity of the fibrin clot to the fibrinolytic system.

In the research that led to the invention, the inventors typed 15 haplotype-tagging single nucleotide polymorphisms (htSNPs, which are SNPs specific to a haplotype) in the three genes of the fibrinogen cluster in a large population-based case-control study on risk factors for venous thrombosis, the Leiden Thrombophilia Study (LETS). Furthermore, the combined levels of the fibrinogen isoforms γA/γ' and γ'/γ', containing an alternatively spliced variant of the fibrinogen γ chain (γ'), were measured in all subjects.

It was found that individuals homozygous for FGB-H2, FGA-H2 or FGG-H2 all had an increased risk for venous thrombosis (FGB-H2: OR=1.9, 95% CI:1.1-3.4; FGA-H2: OR=2.0, 95% CI:1.3-3.2; FGG-H2: OR=2.4, 95%:1.5-3.9). Since the three fibrinogen genes are located on a single stretch of DNA of 50 kb, multiple logistic regression was used to adjust for the linkage disequilibrium between the genes. After adjustment, the elevated risk only remained for individuals homozygous for FGG-H2. None of the fibrinogen haplotypes was associated with total fibrinogen levels as measured with the Clauss method. FGG-H2 was also associated with reduced fibrinogen γ' levels and a reduced fibrinogen γ'/γ ratio. Logistic regression showed that both reduced fibrinogen γ' levels and increased total fibrinogen levels were associated with a threefold increased risk of DVT, even after adjustment for FGG-H2.

On the basis of this finding it was concluded that FGG-H2 is associated with reduced fibrinogen γ' levels and that in multivariate analysis reduced fibrinogen γ' levels are associated with a threefold increased risk of developing DVT, demonstrating that the FGG-H2 haplotype acts on thrombotic risk via the phenotype of a reduced fibrinogen γ' level.

Because the plasma concentration of fibrinogen γ' and of total fibrinogen both influence thrombotic risk and because the fibrinogen γ' level depends always on the total fibrinogen level, the inventors also analysed the effect of the fibrinogen γ'/total fibrinogen ratio (γ'/γ ratio) on the risk of venous thrombosis. They found that individuals with a γ'/γ ratio below 0.69, which represents the tenth percentile (P10) as measured in the control subjects, have an increased risk of venous thrombosis (OR=2.4, 95% CI: 1.7-3.5) compared to those with a γ'/γ ratio ≧0.69. Because FGG-H2 was associated with reduced fibrinogen γ' levels, but also with a reduced γ'/γ ratio, FGG-H2 together with the P10 of the γ'/γ ratio were entered in the same logistic regression model. The risk associated with a reduced γ'/γ ratio (<0.69) remained (OR=2.2, 95% CI: 1.3-3.5), while the risk associated with FGG-H2 homozygosity largely disappeared (OR=1.2, 95% CI: 0.6-2.3). This indicates that the FGG-H2 haplotype acts on the risk of venous thrombosis via reduction of the γ'/γ ratio. 82% of the controls and 91% of the cases with γ'/γ<0.69 were homozygous carriers of the FGG-H2 allele.

Further research showed that by increasing the use of polyadenylation signal-2 (pA2) in the FGG-H2 transcript (see FIG. 2 and FIG. 8) the 10034C>T is responsible for a decreased efficiency of γ' formation and therefore for the reduced γ' content which was found to be associated with the risk of venous thrombosis. Furthermore, it was found that 10034C is part of a functional Cleavage stimulatory Factor (CstF) consensus 2a sequence. For this, mini-gene constructs were made which contained exon 9, intron 9, exon 10 and the 3'-UTR of the FGG gene and the FGG-H2 specific SNPs were introduced in this construct, both together and apart. The presence of 10034C>T resulted in increased use of pA2 and therefore in a reduced pA1/pA2 ratio (FIG. 10). In addition, mutations were introduced in the CstF site, which improved and decreased the consensus sequence, to demonstrate that indeed this site is a functional CstF site. This shows that the 10034 C/T mutation is causing the risk of Venous Thrombosis (VT), in particular deep venous thrombosis (DVT).

Based on these findings the invention provides a method for screening an individual for the presence in his genome of a genetic marker that is indicative of an increased risk of venous thrombosis, in particular deep venous thrombosis, comprising determining the presence in the individual's genome of a genetic marker that is indicative of an increased risk of venous thrombosis, in particular deep venous thrombosis, wherein the genetic marker is haplotype 2 of the fibrinogen γ gene (FGG-H2) as given in FIG. 5.

As is shown in Table 1A, haplotype 2 (H2) of the fibrinogen gamma gene (FGG) can be specifically identified by the presence in the gene of a set of mutations when compared to the reference sequence of FGG (GenBank accession number AF350254 at www.ncbi.nlm.nih.gov). The Nucleotide numbering is according to Seattle database (Nickerson, D, SeattleSNPs. NHLBI Program for genomic Applications, UW-FHCRC. Seattle, Wash. http://pga.gs.washington.edu 15-4-2003). Such a set comprises one, two, three or four mutations selected from the group consisting of 129A/T (rs2066854), 7874G/A (rs2066861), 9615C/T (rs2066864) and 10034C/T (rs2066865) in the nucleic acid material encoding fibrinogen γ, in particular in the FGG gene depicted in FIG. 5B (SEQ ID NO:22). The numbering refers to the nucleotide position in the fibrinogen γ gene as depicted in FIG. 5. The rs numbers identify the SNPs according to the dbSNP (accessible via http://www.ncbi.nlm.nih.gov).

TABLE 1A

|  | 129 A/T | 902 G/A | 5836 G/A | 7874 G/A | 9340 T/C | 9615 C/T | 10034 C/T |
|---|---|---|---|---|---|---|---|
| Haplotype 1 | A | G | G | G | T | C | C |
| Haplotype 2 | T | A | G | A | T | T | T |
| Haplotype 3 | A | A | G | G | C | C | C |
| Haplotype 4 | A | G | A | G | T | C | C |

The set of mutations that is used to identify haplotype 2 is selected from the sets listed in Table 1B. Preferably mutation 10034C/T is at least present. The set of mutations is therefore preferably selected from the sets 5-8, 11, 12, 14 and 15 listed in Table 1B. Specifically, the presence of FGG-H2 is associated with the presence of mutation 10034C/T (rs2066865) in the nucleic acid material encoding fibrinogen γ. In this application a "set" can comprise one, two, three or four mutations.

TABLE 1B

All possible combinations of genetic markers

| Set | Mutations | | | |
|---|---|---|---|---|
| 1 | 129A/T | | | |
| 2 | 129A/T | 7874G/A | | |
| 3 | 129A/T | 7874G/A | 9615C/T | |
| 4 | 129A/T | | 9615C/T | |
| 5 | 129A/T | | 9615C/T | 10034C/T |
| 6 | 129A/T | | | 10034C/T |
| 7 | 129A/T | 7874G/A | | 10034C/T |
| 8 | 129A/T | 7874G/A | 9615C/T | 10034C/T |
| 9 | | 7874G/A | | |
| 10 | | 7874G/A | 9615C/T | |
| 11 | | 7874G/A | 9615C/T | 10034C/T |
| 12 | | 7874G/A | | 10034C/T |
| 13 | | | 9615C/T | |
| 14 | | | 9615C/T | 10034C/T |
| 15 | | | | 10034C/T |

In the method of the invention the genetic marker is detected by carrying out a target nucleic acid amplification reaction of a stretch of DNA comprising said set of mutations and analysing the amplified target nucleic acid for the presence of the set of mutations.

Various techniques for amplifying nucleic acid are known in the art, such as:

PCR (Polymerase Chain Reaction), described in U.S. Pat. Nos. 4,683,195, 4,683,202 and 4,800,159, and its RT-PCR alternative (Reverse Transcription PCR), particularly in its one-step format as disclosed in patent EP-B-0.569.272, LCR (Ligase Chain Reaction), exposed for example in the patent application EP-A-0.201.184, RCR (Repair Chain Reaction), claimed in international application WO-A-90/01069, 3SR (Self Sustained Sequence Replication) described in patent application WO-A-90/06995, NASBA (Nucleic Acid Sequence-Based Amplification) disclosed for instance in EP-B-0.397.269 or U.S. Pat. No. 5,466,586 using double stranded DNA as template, and TMA (Transcription Mediated Amplification), see for instance U.S. Pat. No. 5,399,491.

One example of a technique for the specific amplification of a DNA target segment is the so-called "polymerase chain reaction" (PCR). With the PCR technique the copy number of a particular target segment is increased exponentially with the number of cycles. A pair of primers is used and in each cycle a DNA primer is annealed to the 3' side of each of the two strands of the double stranded DNA-target sequence. The primers are extended with a DNA polymerase in the presence of the various mononucleotides to generate double stranded DNA again. The strands of the double stranded DNA are separated from each other by thermal denaturation and each strand serves as a template for primer annealing and subsequent elongation in a following cycle. The PCR method has also been described in Saiki et al., Science 230, 135, 1985 and in patents EP-B-0.200.362 and EP-A-0.201.184.

Detection of the presence of one or more of the mutations in the amplified product can be performed in various manners that are well known in the art, such as
  use of restriction enzymes
  allele specific amplification
  peptide Nucleic Acid (PNA)-mediated PCR clamping
  detection of conformational differences, like Single Strand Conformation Polymorphism (SSCP) and Denaturing Gradient Gel Electrophoresis (DGGE)
  Assays with detection steps on membranes (dot blot) using labeled oligonucleotide probes
  Assays with detection steps in microtiter plates, like Reverse Hybridisation, Oligonucleotide Ligation Assay (OLA, MLPA), First Nucleotide Change (FNC) technology, Cross-linking technology
  Rapid cycle PCR and simultaneous fluorescence analysis (e.g. 5'nuclease/Taqman)
  PCR followed by mini-sequencing using mass spectrometry or capillary electrophoresis The invention further relates to a kit for performing the method indicative of an increased risk of venous thrombosis, in particular deep venous thrombosis, comprising at least one pair of primers recognizing and hybridizing to stretches of nucleic acid surrounding at least one stretch of nucleic acid comprising at least one mutation, the mutation being a genetic marker of haplotype 2 of the fibrinogen γ gene (FGG-H2) and means for detecting the amplified-target nucleic acid for the presence of said mutation.

More specifically, the kit comprises one pair of primers recognizing and hybridizing to stretches of nucleic acid surrounding one stretch of nucleic acid comprising at least one mutation, the mutation being a genetic marker of haplotype 2 of the fibrinogen γ gene (FGG-H2) and at least one probe for detecting the amplified target nucleic acid for the presence of said mutation. In particular the pair of primers recognizing and hybridizing to stretches of nucleic acid surrounding one stretch of nucleic acid comprise at least one mutation selected from the group consisting of 129A/T, 7874G/A, 9615C/T and 10034C/T, and the at least one probe detects each mutation of interest in the amplified target nucleic acid.

In a first embodiment the kit comprises
  a first oligonucleotide being 10-50 nucleotides in length and comprising one of the following nucleotide sequences or at least a fragment of 10 consecutive nucleotides thereof:

SEQ ID NO: 1:  CTTCACAGAGGCAACTGATTC,

SEQ ID NO: 2:  CCTTCAGACAAAGGGAAGATTG,

SEQ ID NO: 3:  AGCTCCAGCCATTTGCAG,

SEQ ID NO: 4:  TCAGGTCCACATTGTATTCC,

SEQ ID NO: 5:  GGGAGTTGATAGAACCAGTGC,

SEQ ID NO: 6:  TTCCAAGGAAGCATCCTACG,

SEQ ID NO: 7:  GTAACTGGCAATGCACTTCG,

SEQ ID NO: 8:  GAGAACATTTTAGAGTTTCAAATTC,
or

SEQ ID NO: 9:  ACATGCATTTCAATAAACCTTTTGTTTCCT, or the complementary sequence thereof,
  a second oligonucleotide being 10-50 nucleotides in length and comprising one of the following nucleotide sequences or at least a fragment of 10 consecutive nucleotides thereof:

SEQ ID NO: 10:  GTGTCAACCATGTTCATAGGC,

SEQ ID NO: 11:  CCTTTTATGTAAGCTCCTGGG,

SEQ ID NO: 12:  CATAATCAGGCATAATGTCACTG,

SEQ ID NO: 13:  TGAGCTACGGTTCACAAGG,

SEQ ID NO: 14:  GACTCCTGGAGAAAATGGTG,

SEQ ID NO: 15:  GGTGGATTTCTTTAGAAGGGC,

SEQ ID NO: 16:  GCTTTGCAAGTCCATTGTCC,

SEQ ID NO: 17:  GCTATTTCCTTTGTAACTCCC,
or

SEQ ID NO: 18:  GGTAAATTGGCAAAAAGTGGTGGT, or the complementary sequence thereof.

Suitable combinations are the following combinations of SEQ ID NOS: 1&10, 1&11, 1&12, 1&13, 1&14, 1&15, 1&16, 1&17, 1&18, 2&10, 2&11, 2&12, 2&13, 2&14, 2&15, 2&16, 2&17, 2&18, 3&10, 3&11, 3&12, 3&13, 3&14, 3&15, 3&16, 3&17, 3&18, 4&10, 4&11, 4&12, 4&13, 4&14, 4&15, 4&16, 4&17, 4&18, 5&10, 5&11, 5&12, 5&13, 5&14, 5&15, 5&16, 5&17, 5&18, 6&10, 6&11, 6&12, 6&13, 6&14, 6&15, 6&16, 6&17, 6&18, 6&10, 6&11, 6&12, 6&13, 6&14, 6&15, 6&16, 6&17, 6&18, 7&10, 7&11, 7&12, 7&13, 7&14, 7&15, 7&16, 7&17, 7&18, 8&10, 8&11, 8&12, 8&13, 8&14, 8&15, 8&16, 8&17, 8&18, 9&10, 9&11, 9&12, 9&13, 9&14, 9&15, 9&16, 9&17, 9&18.

In a further embodiment the kit for detecting mutation 129A/T comprises
  a first oligonucleotide being 10-50 nucleotides in length and comprising one of the following nucleotide sequences or at least a fragment of 10 nucleotides thereof:
    SEQ ID NO:1: CTTCACAGAGGCAACTGATTC, or the complementary sequence thereof,
  a second oligonucleotide being 10-50 nucleotides in length and comprising the following nucleotide sequences or at least a fragment of 10 consecutive nucleotides thereof:

SEQ ID NO: 2:  CCTTCAGACAAAGGGAAGATTG,

SEQ ID NO: 3:  AGCTCCAGCCATTTGCAG,

SEQ ID NO: 4:  TCAGGTCCACATTGTATTCC,

SEQ ID NO: 5:  GGGAGTTGATAGAACCAGTGC,

SEQ ID NO: 6:  TTCCAAGGAAGCATCCTACG,

-continued

```
SEQ ID NO: 7:    GTAACTGGCAATGCACTTCG,

SEQ ID NO: 8:    GAGAACATTTTAGAGTTTCAAATTC,

SEQ ID NO: 9:    ACATGCATTTCAATAAACCTTTTGTTTCCT,

SEQ ID NO: 10:   GTGTCAACCATGTTCATAGGC,

SEQ ID NO: 11:   CCTTTTATGTAAGCTCCTGGG,

SEQ ID NO: 12:   CATAATCAGGCATAATGTCACTG,

SEQ ID NO: 13:   TGAGCTACGGTTCACAAGG,

SEQ ID NO: 14:   GACTCCTGGAGAAAATGGTG,

SEQ ID NO: 15:   GGTGGATTTCTTTAGAAGGGC,

SEQ ID NO: 16:   GCTTTGCAAGTCCATTGTCC,

SEQ ID NO: 17:   GCTATTTCCTTTGTAACTCCC,
or

SEQ ID NO: 18:   GGTAAATTGGCAAAAAGTGGTGGT,
``` or the complementary sequence thereof.

Suitable combinations are the following combinations of SEQ ID NOS: 1&2, 1&3, 1&4, 1&5, 1&6, 1&7, 1&8, 1&9, 1&10, 1&11, 1&12, 1&13, 1&14, 1&15, 1&16, 1&17, 1&18.

Preferably, the kit for detecting mutation 129A/T comprises a pair of oligonucleotides, wherein the first oligonucleotide is 10-26 nucleotides in length, and the second oligonucleotide is 10-26 nucleotides in length and comprises SEQ ID NO:10: GTGTCAACCATGTTCATAGGC or at least a fragment of 10 consecutive nucleotides thereof, in particular the fragment GTGTCAACCA, TGTCAACCAT, GTCAACCATG, TCAACCATGT, CAACCATGTT, AACCATGTTC, ACCATGTTCA, CCATGTTCAT, CATGTTCATA, ATGTTCATAG, TGTTCATAGG or GTTCATAGGC.

For detecting mutation 7874G/A the kit comprises
a first oligonucleotide being 10-50 nucleotides in length and comprising one of the following nucleotide sequences or at least a fragment of 10 consecutive nucleotides thereof:

```
SEQ ID NO: 1:    CTTCACAGAGGCAACTGATTC,

SEQ ID NO: 2:    CCTTCAGACAAAGGGAAGATTG,

SEQ ID NO: 3:    AGCTCCAGCCATTTGCAG,

SEQ ID NO: 4:    TCAGGTCCACATTGTATTCC,

SEQ ID NO: 5:    GGGAGTTGATAGAACCAGTGC,

SEQ ID NO: 6:    TTCCAAGGAAGCATCCTACG,

SEQ ID NO: 10:   GTGTCAACCATGTTCATAGGC,

SEQ ID NO: 11:   CCTTTTATGTAAGCTCCTGGG,

SEQ ID NO: 12:   CATAATCAGGCATAATGTCACTG,

SEQ ID NO: 13:   TGAGCTACGGTTCACAAGG,

SEQ ID NO: 14:   GACTCCTGGAGAAAATGGTG,
or

SEQ ID NO: 15:   GGTGGATTTCTTTAGAAGGGC,
``` or the complementary sequence thereof,
a second oligonucleotide being 10-50 nucleotides in length and comprising one of the following nucleotide sequences or at least a fragment of 10 consecutive nucleotides thereof:

```
SEQ ID NO: 7:    GTAACTGGCAATGCACTTCG,

SEQ ID NO: 8:    GAGAACATTTTAGAGTTTCAAATTC,

SEQ ID NO: 9:    ACATGCATTTCAATAAACCTTTTGTTTCCT,

SEQ ID NO: 16:   GCTTTGGAAGTCCATTGTCC,

SEQ ID NO: 17:   GCTATTTCCTTTGTAACTCCC,
or

SEQ ID NO: 18:   GGTAAATTGGCAAAAAGTGGTGGT,
``` or the complementary sequence thereof.

Suitable combinations are combinations of SEQ ID NOS: 1&7, 1&8, 1&9, 1&16, 1&17, 1&18, 2&7, 2&8, 2&9, 2&16, 2&17, 2&18, 3&7, 3&8, 3&9, 3&16, 3&17, 3&18, 4&7, 4&8, 4&9, 4&16, 4&17, 4&18, 5&7, 5&8, 5&9., 5&16, 5&17, 5&18, 6&7, 6&8, 6&9, 6&16, 6&17, 6&18, 10&7, 10&8, 10&9, 10&16, 10&17, 10&18, 11&7, 11&8, 11&9, 11&16, 11&17, 11&18, 12&7, 12&8, 12&9, 12&16, 12&17, 12&18, 13&7, 13&8, 13&9, 13&16, 13&17, 13&18, 14&7, 14&8, 14&9, 14&16, 14&17, 14&18, 15&7, 15&8, 15&9, 15&16, 15&17, 15&18.

Preferably, the first oligonucleotide is 10-26 nucleotides in length and comprises SEQ ID NO:6: TTCCAAGGAAGCATCCTACG or at least a fragment of 10 consecutive nucleotides thereof, in particular the fragments TTCCAAGGAA, TCCAAGGAAG, CCAAGGAAGC, CAAGGAAGCA, AAGGAAGCAT, AGGAAGCATC, GGAAGCATCC, GAAGCATCCT, AAGCATCCTA, AGCATCCTAC or GCATCCTACG and the second oligonucleotide being 10-26 nucleotides in length and comprising at least a fragment of 10 consecutive nucleotides of SEQ ID NO:16: GCTTTGCAAGTCCATTGTCC, in particular the fragment GCTTTGCAAG, CTTTGCAAGT, TTTGCAAGTC, TTGCAAGTCC, TGCAAGTCCA, GCAAGTCCAT, CAAGTCCATT, AAGTCCATTG, AGTCCATTGT, GTCCATTGTC or TCCATTGTCC.

For detecting mutation 9615C/T the kit comprises
a first oligonucleotide being 10-50 nucleotides in length and comprising one of the following nucleotide sequences or at least a fragment of 10 consecutive nucleotides thereof:

```
SEQ ID NO: 1:    CTTCACAGAGGCAACTGATTC,

SEQ ID NO: 2:    CCTTCAGAGAAAGGGAAGATTG,

SEQ ID NO: 3:    AGCTCCAGCCATTTGCAG,

SEQ ID NO: 4:    TCAGGTCCACATTGTATTCC,

SEQ ID NO: 5:    GGGAGTTGATAGAACCAGTGC,

SEQ ID NO: 6:    TTCCAAGGAAGCATCCTACG,

SEQ ID NO: 7:    GTAACTGGCAATGCACTTCG,

SEQ ID NO: 10:   GTGTCAACCATGTTCATAGGC,

SEQ ID NO: 11:   CCTTTTATGTAAGCTCCTGGG,

SEQ ID NO: 12:   CATAATCAGGCATAATGTCACTG,

SEQ ID NO: 13:   TGAGCTACGGTTCACAAGG,

SEQ ID NO: 14:   GACTCCTGGAGAAAATGGTG,
or

SEQ ID NO: 15:   GGTGGATTTCTTTAGAAGGGC,
``` or the complementary sequence thereof,
a second oligonucleotide being 10-50 nucleotides in length and comprising one of the following nucleotide sequences or at least a fragment of 10 consecutive nucleotides thereof:

SEQ ID NO: 8:   GAGAACATTTTAGAGTTTCAAATTC,

SEQ ID NO: 9:   ACATGCATTTCAATAAACCTTTTGTTTCCT,

SEQ ID NO: 16:  GCTTTGCAAGTCCATTGTCC,

SEQ ID NO: 17:  GCTATTTCCTTTGTAACTCCC,
or

SEQ ID NO: 18:  GGTAAATTGGCAAAAAGTGGTGGT, or the complementary sequence thereof.
Suitable combinations are the combinations of the SEQ ID NOS: 1&8, 1&9, 1&16, 1&17, 1&18, 2&8, 2&9, 2&16, 2&17, 2&18, 3&8, 3&9, 3&16, 3&17, 3&18, 4&8, 4&9, 4&16, 4&17, 4&18, 5&8, 5&9, 5&16, 5&17, 5&18, 6&8, 6&9, 6&16, 6&17, 6&18, 7&8, 7&9, 7&16, 7&17, 7&18, 10&8, 10&9, 10&16, 10&17, 10&18, 11&8, 11&9, 11&16, 11&17, 11&18, 12&8, 12&9, 12&16, 12&17, 12&18, 13&8, 13&9, 13&16, 13&17, 13&18, 14&8, 14&9, 14&16, 14&17, 14&18, 15&8, 15&9, 15&16, 15&17, 15&18.

Preferably, the first oligonucleotide is 10-26 nucleotides in length and comprises SEQ ID NO:7: GTAACTGGCAATG-CACTTCG or at least a fragment of 10 consecutive nucleotides thereof, in particular the fragment GTAACTGGCA, TAACTGGCAA, AACTGGCAAT, ACTGGCAATG, CTG-GCAATGC, TGGCAATGCA, GGCAATGCAC, GCAATG-CACT, CAATGCACTT, AATGCACTTC, or ATGCACT-TCG and the second oligonucleotide is 10-26 nucleotides in length and comprises SEQ ID NO:16: GCTTTGCAAGTC-CATTGTCC or at least a fragment of 10 nucleotides thereof, in particular the fragment GCTTTGCAAG, CTTTGCAAGT, TTTGCAAGTC, TTGCAAGTCC, TGCAAGTCCA, GCAAGTCCAT, CAAGTCCATT, AAGTCCATTG, AGTC-CATTGT, GTCCATTGTC, TCCATTGTCC.

For detecting mutation 10034C/T the kit comprises
a first oligonucleotide being 10-50 nucleotides in length and comprising one of the following nucleotide sequences or at least a fragment of 10 nucleotides thereof:

SEQ ID NO: 1:   CTTCACAGAGGCAACTGATTC,

SEQ ID NO: 2:   CCTTCAGACAAAGGGAAGATTG,

SEQ ID NO: 3:   AGCTCCAGCCATTTGCAG,

SEQ ID NO: 4:   TCAGGTCCACATTGTATTCC,

SEQ ID NO: 5:   GGGAGTTGATAGAACCAGTGC,

SEQ ID NO: 6:   TTCCAAGGAAGCATCCTACG,

SEQ ID NO: 7:   GTAACTGGCAATGCACTTCG,

SEQ ID NO: 8:   GAGAACATTTTAGAGTTTCAAATTC,

SEQ ID NO: 9:   ACATGCATTTCAATAAACCTTTTGTTTCCT,

SEQ ID NO: 10:  GTGTCAACCATGTTCATAGGC,

SEQ ID NO: 11:  CCTTTTATGTAAGCTCCTGGG,

SEQ ID NO: 12:  CATAATCAGGCATAATGTCACTG,

-continued

SEQ ID NO: 13:  TGAGCTACGGTTCACAAGG,

SEQ ID NO: 14:  GACTCCTGGAGAAAATGGTG,

SEQ ID NO: 15:  GGTGGATTTCTTTAGAAGGGC,
or

SEQ ID NO: 16:  GCTTTGCAAGTCCATTGTCC, or the complementary sequence thereof,
a second oligonucleotide being 10-50 nucleotides in length and comprising one of the following nucleotide sequences or at least a fragment of 10 nucleotides thereof:

SEQ ID NO: 17:  GCTATTTCCTTTGTAACTCCC,
or

SEQ ID NO: 18:  GGTAAATTGGCAAAAAGTGGTGGT, or the complementary sequence thereof.
Suitable combinations are combinations of SEQ ID NOS: 1&17, 1&18, 2&17, 2&18, 3&17, 3&18, 4&17, 4&18, 5&17, 5&18, 6&17, 6&18, 7&17, 7&18, 8&17, 8&18, 9&17, 9&18, 10&17, 10&18, 11&17, 11&18, 12&17, 12&18, 13&17, 13&18, 14&17, 14&18, 15&17, 15&18, 16&17, 16&18.

Preferably, the first oligonucleotide is 10-26 nucleotides in length and comprises SEQ ID NO:8: GAGAACATTTTA-GAGTTTCAAATTC, in particular the fragment AGAA-CATTTT, GAACATTTTA, AACATTTTAG, ACATTT-TAGA, CATTTTAGAG, ATTTTAGAGT, TTTTAGAGTT, TTTAGAGTTT, TTAGAGTTTC, TAGAGTTTCA, AGAGTTTCAA, GAGTTTCAAA, AGTTTCAAAT, GTTTCAAATT or TTTCAAATTC or SEQ ID NO:9: ACAT-GCATTTCAATAAACCTTTTGTTTCCT, in particular the fragment ACATGCATTT, CATGCATTTC, ATGCATTTCA, TGCATTTCAA, GCATTTCAAT, CATTTCAATA, ATTTCAATAA, TTTCAATAAA, TTCAATAAAC, TCAATAAACC, CAATAAACCT, AATAAACCTT, ATAAACCTTT, TAAACCTTTT, AAACCTTTTG, AAC-CTTTTGT, ACCTTTTGTT, CCTTTTGTTT, CTTTTGTTTC, TTTTGTTTCC, or TTTGTTTCCT or at least a fragment of 10 consecutive nucleotides thereof, and the second oligonucleotide is 10-26 nucleotides in length.

In a particularly advantageous embodiment the kit comprises one probe for detecting each mutation (129A/T, 7874G/A, 9615C/T or 10034C/T) of interest in the amplified target nucleic acid, said probe comprising a nucleic acid sequence corresponding to the analyte nucleic acid that has been mutated to discriminate it from an non-mutated analyte nucleic acid. Preferably, the probe is a molecular beacon.

The probe for detecting FGG-H2 haplotype by binding to the 10034T allele (mutation 10034C/T) is or contains an oligonucleotide being 10-50 nucleotides in length, preferentially 10-26, and comprising SEQ ID NO:19: ATGGT-CAATAAAGATACCA or at least a fragment of 10 consecutive nucleotides thereof, in particular the fragment ATGGTCAATA, TGGTCAATAA, GGTCAATAAA, GTCAATAAAG, TCAATAAAGA, CAATAAAGAT, AATAAAGATA, ATAAAGATAC, TAAAGATACC, or AAAGATACCA. The kit may further contain a probe for detecting FGG-H2 haplotype by binding to the 10034C allele which is or contains an oligonucleotide being 10-50 nucleotides in length, preferentially 10-26, and comprising SEQ ID NO:20: TTTTAATGGTCAATAAAGGTACCA or at least a fragment of 10 consecutive nucleotides thereof, in particular the fragment TTTTAATGGT, TTTAATGGTC, TTAATG-GTCA, TAATGGTCAA, AATGGTCAAT, ATGGTCAATA, TGGTCAATAA, GGTCAATAAA, GTCAATAAAG, TCAATAAAGG, CAATAAAGGT, AATAAAGGTA, ATAAAGGTAC, TAAAGGTACC, or AAAGGTACCA.

Each kit may further contain suitable amplification reagents. This is however not an essential part of the kit as these reagents may also be provided separately.

In many methods of biological analysis, a solid phase has to be separated from a liquid phase and subsequently washed. To wash the solid phase, a defined amount of buffer solution is pipetted into the reaction vessel containing the solid phase to suspend the solid phase in the buffer solution. The solid and the liquid phases are then separated. The liquid phase is then removed by suction (aspiration) and a new washing process begins. Usually a number of washing cycles are carried out, each including a suspension, separation and aspiration process.

The use of magnetic particles as a solid phase and separation by permanent magnets is known in principle. Permanent magnets attract the particles to the wall of the reaction vessel and hold them there.

Magnetic particles are often used in separation processes. There are many biological assay methods and purification methods in which magnetic particles are used. For example, immunoassay methods, nucleic acid hybridisation assays and the like. Magnetic particles can also be used in purification methods, to isolate particular components, proteins, nucleic acids, from the material in which they were contained. The particles can be used to separate certain components from a mixture, for example, because they are coated with a reagent with a specific affinity for the component. Magnetic particles can be drawn to, for example, the wall of a container in which the fluid with the magnetic particles was contained and the fluid can be removed and, optionally, be replaced with another fluid. Thus, the particles can be mixed with the fluid from which the specific component is to be removed, the component will bind to the magnetic particle, and a magnet can be used to separate the particles with the component from the remainder of the mixture in the fluid. Optionally the magnetic particles can be washed, and can be separated in another fluid. Or the component can be removed from the particles again into another fluid. The use of the magnetic particles is a heterogeneous procedure as the detection takes place after amplification and separation of the amplicons from the rest of the sample.

In a homogeneous procedure, amplification and detection occur without separating the reaction components. Amplicons are detected in the course of the amplification. Thus, the generation of amplicons can be monitored real-time and the data thus obtained can be used to determine the presence or absence or the amount of the amplicon. One type of probe that is very useful in such homogeneous techniques is the molecular beacon.

Molecular beacons are single-stranded oligonucleotides having a stem-loop structure. The loop portion-contains the sequence complementary to the target nucleic acid (either DNA or RNA). The stem is formed due to hydridisation of the complementary sequence of the 3' end with the 5' end. The stem can be unrelated to the target and is double-stranded. One arm of the stem is labelled with a fluorescent dye (fluorophore), whereas the other one is coupled to a quenching molecule. In the stem-loop state the probe does not produce fluorescence because the energy of the fluorophore is transferred to the quenching molecule. When the molecular beacon hybridises to the target the stem-loop structure is lost and the quencher and fluorophore are separated. At that stage the fluorescence emitted by the fluorophore can be detected and quantified.

In this application the terms "analyte", "amplicons" and "target" or "target sequence" may be used interchangeably. The analyte is the original nucleic acid molecule to be detected. The target sequence is the part of the analyte that is amplified by means of the primers. The amplification leads to formation of amplicons, which are the nucleic acid molecules that are physically detected by hybridisation to the probe. The sequence of the amplicons is the same or complementary to the target sequence within the analyte.

The present invention is further elucidated in the examples that follow and in which reference is made to the following figures:

FIG. 1 shows the structure of fibrinogen.

Figure 2:
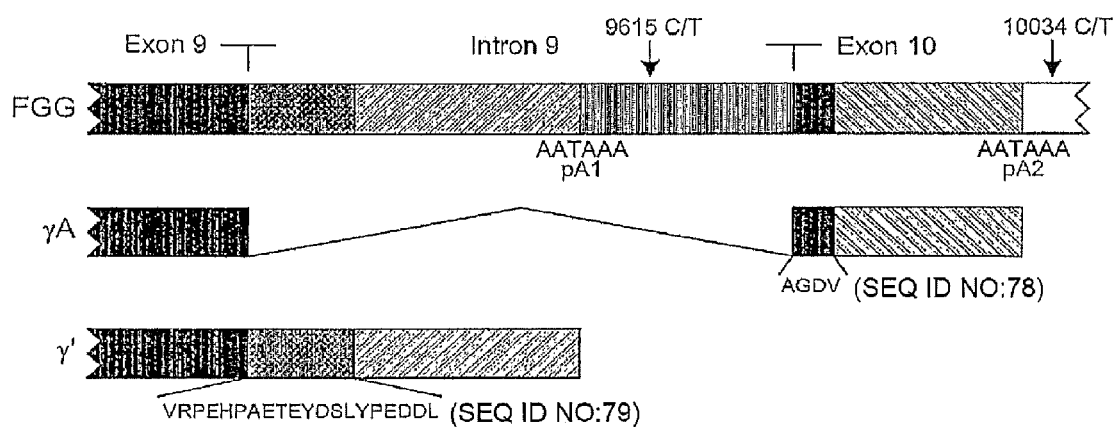

FIG. 2 shows alternative mRNA processing of γ chain mRNA. The γA chain is translated from an mRNA in which all 9 introns of the pre-mRNA have been removed and polyadenylation occurred downstream from exon 10. In contrast, the γ' chain arises from alternative processing of the FGG pre-mRNA. Intron 9 is not removed and polyadenylation occurs at an alternative site located in this intron. This leads to the translation of a polypeptide with a unique 20-amino acid extension (SEQ ID NO:79), encoded by intron 9, substituted for the carboxyl-terminal four amino acids (SEQ ID NO:78) of the γ chain encoded by exon 10. This variant chain comprises approximately 7-15% of the fibrinogen γ chain found in plasma. Nearly all of the γ' protein occurs in vivo as a heterodimer with the γA variant where one D region contains a γ' carboxyl terminus and the other a γA carboxyl terminus (γA/γ' fibrinogen).

Figures 3, 4:
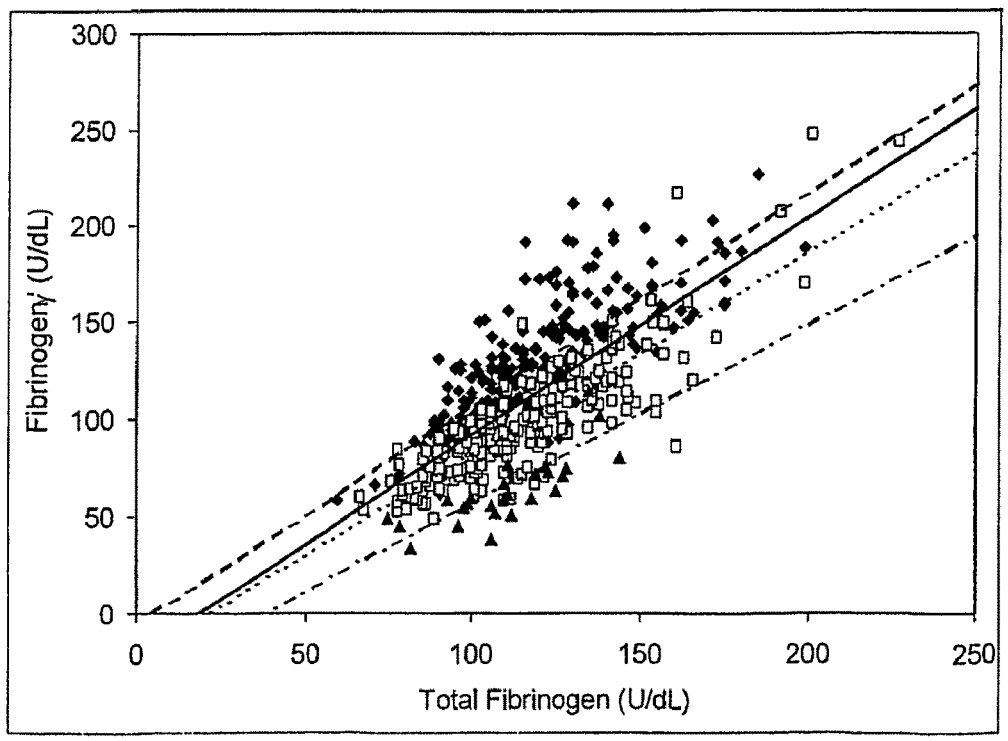

FIG. 3 shows the htSNPs in the fibrinogen gene cluster used for genotyping the Leiden Thrombophilia Study. The numbering of the nucleotides is according to SeattleSNPs (deposited in GenBank as AF350254 (FGG), AF361104 (FGA), AF388026(FGB)). The numbering of the haplotypes in the three fibrinogen genes (FGG, FGA, FGB) is arbitrary. F: haplotype frequencies in control population of the Leiden Thrombophilia Study.

FIG. 4 shows the FGG haplotype dependent correlation between total fibrinogen levels (U/dL) and fibrinogen γ' levels (U/dL) in control subjects (n=471). ♦ ( - - - ) FGG HxHx, ☐ ( . . . ) FGG H2Hx, ▲ (_._._._) FGG H2H2, (_____) A11

FIG. 5A shows the sequence of the haplotype 2 allele of the fibrinogen γ gene (SEQ ID NO:76). The mutations are shown in bold capitals. Reference sequence is the FGG sequence with the GenBank accession number AF350254 (FIG. 5B; SEQ ID NO:77).

Figure 6:
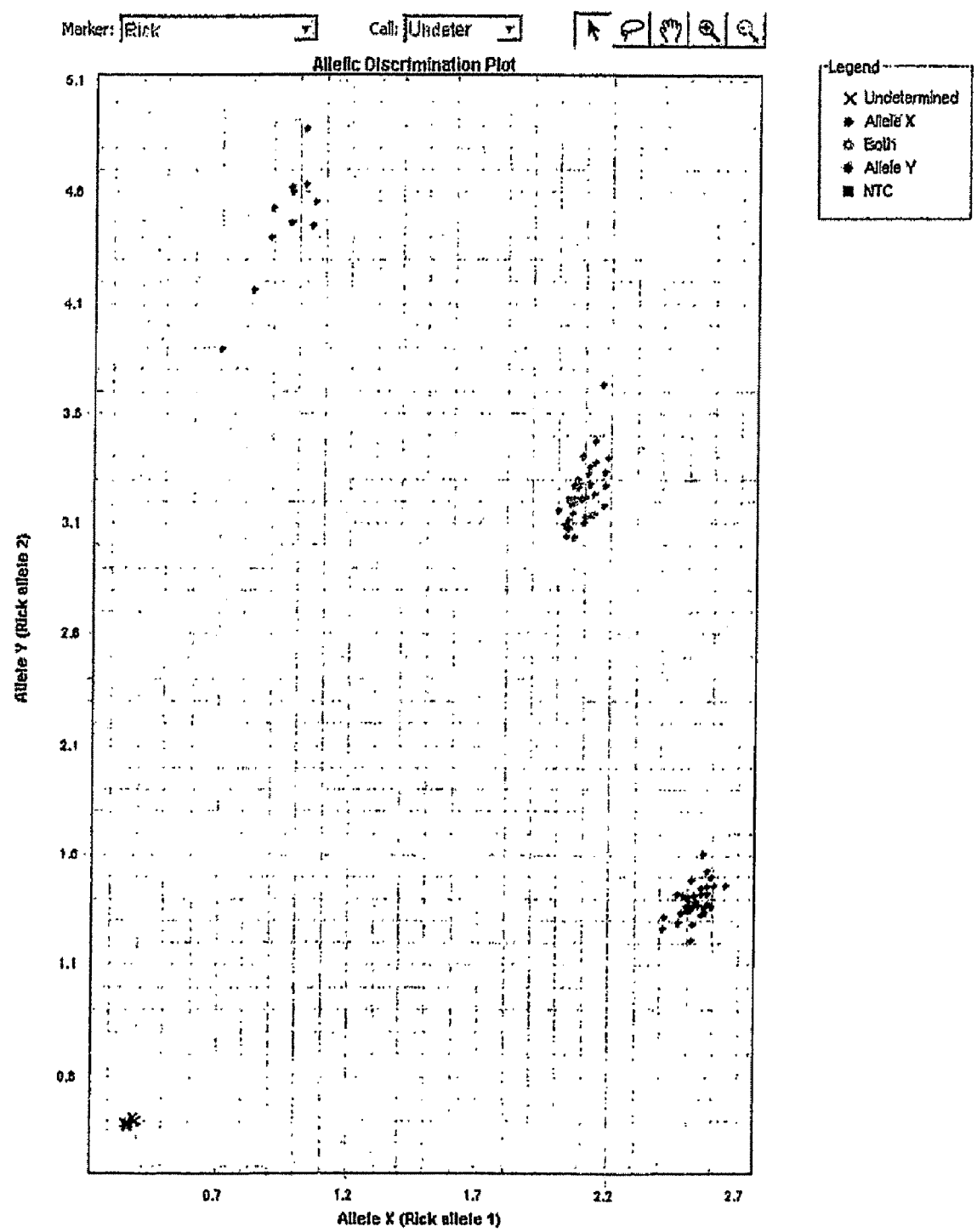
Figure 7:
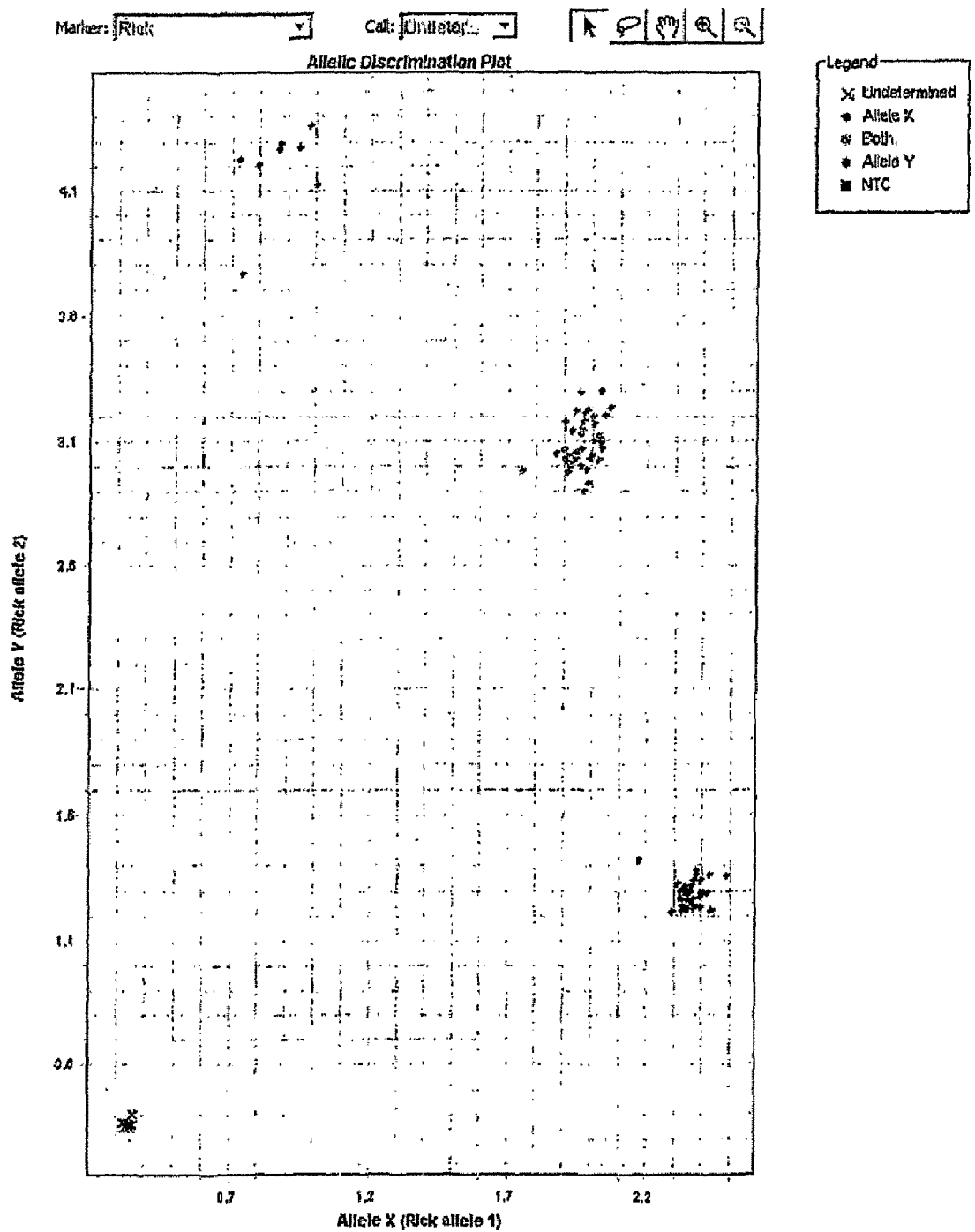

FIGS. 6 and 7 show the results of Example 2.

Figure 8:
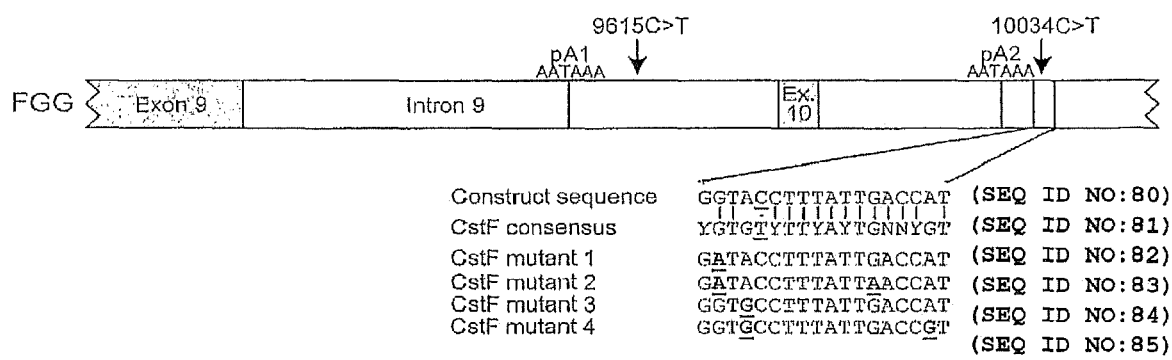

FIG. 8 shows the schematic representation of the insert of the mini-gene constructs. The insert contains exon 9, intron 9, exon 10 and the 3'UTR of the FGG gene, containing polymorphisms 9615C>T and 10034C>T. For details on the insert see the file in FIG. 9. Enlarged, part of the construct sequence (SEQ ID NO:80) containing SNP 10034C>T (underlined) is depicted, aligned with the CstF consensus sequence (SEQ ID NO:81)and the CstF mutants (SEQ ID NO:82-85). The mutated nucleotides of the CstF mutant constructs are bold and underlined. The vertical lines indicate the nucleotides between the construct sequence and the CstF consensus sequence that align (14 out of 18).

FIG. 9A shows the nucleotide sequence (SEQ ID NO:86)of the insert in the mini-gene constructs.

Insert sequence: FGG nt 9090 to nt 10151

BOLD DOUBLE UNDERLINED: primers used to obtain the insert from DNA

DOTTED UNDERLINED: exon 9 and exon 10

NORMAL: intron 9

STRIPED UNDERLINED: 3'UTR

ITALIC: nucleotide sequence coding for the 20 amino acids of the γ' chain
BOLD UNDERLINED: reversed primers Real Time PCR
BOLD: probes Real Time PCR
C* in the middle: SNP 9615
C** at the end: SNP 10034
FIG. 9B shows the same picture of SEQ ID NO:86 in color.
Pink: primers used to obtain the insert from DNA
Blue: exon 9 and exon 10
Black: intron 9
Green: 3'UTR
Brown Italic: nucleotide sequence coding for the 20 amino acids of the γ' chain
orange: reversed primers Real Time PCR
Bold: probes Real Time PCR
Red C in the middle: SNP 9615
Red C at the end: SNP 10034
Primers and probes Real Time PCR:

```
Forward on construct:
TGCAGATATCCATCACACTGG         (SEQ ID NO: 23)

Reverse pA1-transcripts:
TCATCCTCAGGGTAAAGTGAGTC       (SEQ ID NO: 24)

Reverse pA2-transcripts:
GAAGTGAAGCTTTGCAAGTCC         (SEQ ID NO: 25)

Probe pA1-transcripts:
AAACAGGTCAGACCAGAGCACCCT      (SEQ ID NO: 26)

Probe pA2-transcripts:
CTGGAGACGTTTAAAAGACCGTTTC     (SEQ ID NO: 27)
```

FIG. 10 shows the relative use of pA1 and pA2 (pA1/pA2 ratio (%)) after three independent transfection experiments, using two separate construct preparations. Four real time PCRs were done with each cDNA sample in triplo. Reference construct CC (9615C and 10034C) set at 100%; mean±sd TT (961ST and 10034T): 71.5%±12; CT (9615C and 10034T): 85.3%±3.3; TC (9615T and 10034C): 101.6%±18.

FIG. 11 shows the relative use of pA1 and pA2 (pA1/pA2 ratio (%)) for the different CstF mutant mini-gene constructs after three independent transfection experiments, using two separate construct preparations. Three real time PCRs were done with each cDNA sample in triplo. Reference construct CstFC was set at 100%; mean±sd CstFmut1: 142.4%±26; CstFmut2: 160.7%±23; CstFmut3: 66.2%±6; CstFmut4: 59.7%±7.

EXAMPLES

Example 1

Fibrinogen Haplotypes and the Risk of Venous Thrombosis
1. Methods
1.1 Study Population The design of the Leiden Thrombophilia Study has been described in detail in Koster et al., Lancet 342: 1503-1506 (1993) and Van der Meer et al. Thromb Haemost. 78: 631-635 (1997).

In total, 474 consecutive patients with an objectively confirmed first episode of deep vein thrombosis and 474 controls, frequency matched for sex and age, were included in this study. Individuals with active cancer were excluded. The control subjects were acquaintances or partners of the patients, also without individuals with cancer. The mean age for both groups was 45 years (range 15-69 for patients, 15-72 for controls). Both groups consisted of 272 (57.4%) women and 202 (42.6%) men.

Venous blood was collected into 0.1 volume of 0.106 mol/L trisodium citrate. Plasma was prepared by centrifugation for 10 minutes at 2000 g at room temperature and stored at −70° C. High molecular weight DNA was isolated from leukocytes by standard methods and stored at −20° C. DNA samples were available from 471 patients and 471 controls. Plasma samples were available from 473 patients and 474 controls.

1.2 Genetic Analysis

There are five haplotypes known in the FGG gene, seven in the FGA gene and seven in the FGB gene (FIG. 3). To tag these haplotypes all subjects were genotyped for 15 haplotype-tagging (ht) SNPs; four in FGG, five in FGA and six in FGB (Table 2). Genotyping of FGB was performed by polymerase chain reaction and restriction fragment length polymorphism analysis.

TABLE 2

| Name and rs numbers of the htSNPs | | | |
|---|---|---|---|
| Gene | SeattleSNP | Rs number | Haplotype (s) |
| FGG | 129 A/T | rs2066854 | H2 + H5 |
|  | 5836 G/A | rs2066860 | H4 |
|  | 7874 G/A | rs2066861 | H2 |
|  | 9340 T/C | rs1049636 | H3 |
|  | 9615 C/T | rs2066864 | H2 |
|  | 10034 C/T | rs2066865 | H2 |
| FGA | 251 G/A | rs2070006 | H2 + H3 |
|  | 3655 G/A | rs2070014 | H7 − |
|  | 3807 T/C | rs2070016 | H4 + H6 |
|  | 3845 G/A | rs2070017 | H5 |
|  | 6534 A/G | rs6050 | H2 |
| FGB | 1038 G/A | rs1800791 | H6 |
|  | 1643 C/T | rs1800789 | H2 |
|  | 3471 T/C | rs2227432 | H5 |
|  | 9952 A/C | rs2227421 | H1 |
|  | 10149 C/T | rs2227439 | H3 |
|  | 11046 T/C | rs209502 | H4 + H5 |

Genotyping of FGA and FGG was performed using the 5' nuclease/TaqMan assay (Livak, Genet. Anal. 14: 143-149 (1999)).

The polymerase chain reactions with fluorescent allele-specific oligonucleotide probes (Assay-by-Design/Assay-on-Demand, Applied Biosystems, Foster City, USA) were performed on a PTC-225 (Biozym, Hessisch Oldendorf, Germany) and fluorescence endpoint reading for allelic discrimination was done on an ABI 7900 HT (Applied Biosystems, Foster City, USA). No haplotypes could be assigned to 10 patients and 9 controls, because of missing DNA, genotyping failure, or recombination within a gene. Arlequin population genetics software (Version 2) (Schneider et al. (2000) Arlequin: a software for population genetics data analysis. Genetics and Biometry Lab, Department of Antropology, University of Geneva) and Haploview software v2.0530 were used for haplotype and LD analyses.

1.3 Sequencing

In selected individuals, all promoters, 5' UTRs, exons, intron/exon boundaries, and 3' UTRs of the three fibrinogen genes were sequenced on an ABI PRISM® 310 genetic Analyzer (Perkin Elmer, Boston, USA). Reactions were performed using the ABI PRISM® BigDye Terminator Cycle Sequencing kit (Perkin Elmer). Primers are listed below.

Sequence primers Fibrinogeen:

| Gene | Target | Forward primer | Reverse primer |
|---|---|---|---|
| FGG | PR 1 | CTTCACAGAGGCAACTGATTC | GTGTCAACCATGTTCATAGGC |
| | PR 2 | CCTTCAGACAAAGGGAAGATTG | CCTTTTATGTAAGCTCCTGGG |
| | Exon 1-4 | AGCTCCAGCCATTTGCAG | CATAATCAGGCATAATGTCACTG |
| | Exon 5-6 | TCAGGTCCACATTGTATTCC | TGAGCTACAGTTCACAAGG |
| | Exon 7 | GGGAGTTGATAGAACCAGTGC | GACTCCTGGAGAAAATGGTG |
| | Exon 8 | TTCCAAGGAAGCATCCTACG | GGTGGATTTCTTTAGAAGGGC |
| | Exon 9-10 | GTAACTGGCAATGCACTTCG | GCTTTGCAAGTCCATTGTCC |
| | 3'UTR | GAGAACATTTTAGAGTTTCAAATTC | GCTATTTCCTTTGTAACTCCC |
| FGA | PR | CCTTCAGGGCCAGCTTATC | CACTTAGGACCAGGCAGACG |
| | Exon 1 | CAGCCCCACCCTTAGAAAAG | CCTGGGGTCATAAAGCTAAGAGT |
| | Exon 2-3 | CCTCTTCTGGCTAACATTGC | CAGGGATATTATGAAGGTATGTG |
| | Exon 4 | CTCAGCAGCTACTTCAATAACC | GTGCATAACTATCGCCTTCC |
| | Exon 5-1 | Same as exon 4 | TTAATGCCTTCCACTCTGG |
| | Exon 5-2 | CCGATCTTGTCGAGGGTC | CATAGGTGAGAAGAAACCTGG |
| | Exon 5-3 | CTGGACCTCTGAGAGCTCTG | GACATGGCTCTGTACTGTTAGG |
| | Exon 6 | CCGTGCCTATCTTTGTAAAG | AAGACAGAGTGCTCCCATTC |
| | 3'UTR | GACCCAATAGGCTGAAGAAG | GGGTGGTATACTGGATTGC |
| FGB | PR 1 | GCATGCTGGATTGAATCC | CCAGTCAGTAATCCAAATCCC |
| | PR 2 | CAAACCCTGATAACCTGCCATC | GGTTCACTTGTTGGCTGAACC |
| | Exon 1 | GTTCAGCCAACAAGTGAACC | GCTAAGCCATCCTCATCTTAAG |
| | Exon 2-3 | GGGTGTTGGAATAGTTACATTG | TTATCTGGCAAGTTGCAGG |
| | Exon 4-5 | AACTGCTTGGTGATAGCTCAG | CCAAGGTGCTGGAATTACAG |
| | Exon 6-7 | AATGGACAGGGGATTCAGAT | GAAATGCTTTCGAGTGATGC |
| | Exon 8 | GACTACTGTGCACACGAGTG | GTCTGCTTGAGAGTTTTAGAGG |
| | 3'UTR | CCTTCTTCCCACAGCAATAG | GAGGTTGTGAACGCTTCTCC |

1.4 Fibrinogen Measurement

Total fibrinogen was determined according to the method of Clauss using Dade® thrombin reagent (Baxter, Miami, Fla., USA). The test was performed on an Electra 1000 (MLA, Pleasantville, USA). Total fibrinogen levels were expressed in U/dL, where 100 U/dL corresponds to 2.8 g/L. Total fibrinogen as measured by Clauss corresponded well with total fibrinogen as measured by ELISA using commercial rabbit anti fibrinogen antibodies (DAKO A/S, Glostrup, Denmark) ($R^2$=0.902; n=60).

1.5 Fibrinogen γ' Antigen Measurement

Fibrinogen γ' (i.e. γA/γ' and γ'/γ' fibrinogen) antigen levels were measured by ELISA using the antibody 2.G2.H9 raised against a peptide consisting of the carboxyterminal sequence (VRPEHPAETEYDSLYPEDDL (SEQ ID NO:28)) of the γ' chain as disclosed in US2003/0003515 (available from Campro Scientific, Veenendaal, the Netherlands). This antibody recognizes an epitope including the high affinity binding site for thrombin and is specific for the γ' chain.

Plastic 96-well microtiter plates (Greiner, Alphen a/d Rijn, the Netherlands) were coated (110 μl/well) with 2 μg/ml mouse anti-human γ' fibrinogen, during an overnight incubation at 4° C. Plates were blocked with 110 μl 1% bovine serum albumin (BSA) in washing buffer (50 mM Triethanolamine, 100 mM NaCl, 10 mM EDTA, 0.1% Tween-20, pH 7.5) for one hour at room temperature. One hundred μl of plasma sample diluted in dilution buffer (50 mM Triethanolamine, 100 mM NaCl, 10 mM EDTA, 0.1% Tween-20, 10 mM benzamidine, pH 7.5) was added to the wells and plates were incubated at room temperature for 1 hour. Sample dilutions were stable for at least three hours at room temperature.

Bound fibrinogen γ' (γA/γ' plus γ'/γ') was detected with 100 μl 1:20,000 diluted HRP-conjugated rabbit anti-human fibrinogen (DAKO A/S, Glostrup, Denmark). After 1 hour incubation at room temperature, plates were incubated with 100 μl/well substrate buffer (0.1 M sodium acetate pH 5.0, 0.1 mg/ml tetramethyl-benzidine, 0.01% $H_2O_2$). After 15 minutes, the reaction was stopped by adding 1 M $H_2SO_4$ (50 μl/well) and the absorbance at 450 nm was read spectrophotometrically. Between all incubation steps, wells were washed three times with washing buffer.

A calibration curve was obtained using 1:2,000 to 1:128,000 dilutions of pooled normal plasma, which contained 100 U/dL fibrinogen γ' (γA/γ' plus γ'/γ') by definition. Fibrinogen γ' antigen of a plasma sample was calculated as the mean result of the measurements of two different independent dilutions (1:8,000, 1:16,000). Results were expressed in U/dL. The mean coefficient of variation (CV) was 9.3%. Intra-assay variation was 4.5%.

1.7 Statistical Analysis

In the healthy controls, Hardy-Weinberg equilibrium for each htSNP was tested by $\chi^2$ analysis. To investigate whether haplotypes of fibrinogen were associated with thrombosis, odds ratios (ORs) and 95% confidence intervals (95% CIs) according to Woolf (Ann. Hum. Genet. 19:251-253 (1955)) were calculated as a measure of the relative risk, which indicates the risk of developing thrombosis in a category of exposure (e.g. haplotype 2 carriers) relative to the reference category (e.g. non-haplotype 2 carriers).

The three fibrinogen genes are located on a single stretch of 50 kb of DNA. This results in a high degree of linkage disequilibrium (LD). To adjust for this, the odds ratios of the risk haplotypes of each gene were calculated by means of multiple logistic regression.

The primary measure of association in case-control studies is the relative risk as estimated by the odds ratio. This odds ratio indicates the risk of developing disease in those with a risk factor (or a category of a risk factor) relative to the risk in those without the risk factor (or reference category of the risk factor). In a case-control study, this odds ratio is calculated as the exposure odds ratio, i.e. the ratio of the odds of exposure in the cases over the odds of exposure in the controls. This odds ratio may be biased due to confounding, which occurs when an extraneous determinant of disease has an uneven distribution over the categories of the risk factor under study. In this case, the odds ratio needs to be adjusted, which is performed by calculating a common estimate from a stratified analysis, with strata based on categories of the confounding factor. To accommodate multiple confounders simultaneously, the main analytic technique is unconditional logistic regression. Briefly, $$\log(p/(1-p)) = b_0 + b_1 x_1 + b_k x_k$$

p=1 if a case; 0 if a control $b_0$=intercept $b_1$ regression coefficient of variable of interest x1=categories of variable of interest $b_k$=fitted logistic regression coefficients for potential confounders (k=2, 3, 4 . . . )

$x_k$=categories of confounding variables (k=2, 3, 4 . . . )

In this model, antilog($b_1$) is the odds ratio of the variable of interest. Logistic regression algorithms estimate coefficients by iterative procedures, and standard errors are derived from the likelihood function. These standard-errors serve to construct 95% confidence intervals.

To investigate the association between the various fibrinogen haplotypes, plasma fibrinogen levels and fibrinogen γ' levels, mean levels with 95% CIs were calculated. Quartiles of the fibrinogen γ' levels, measured in the control subjects, were used as cut-off points to assess whether a low fibrinogen γ' level was associated with the risk of venous thrombosis. Multiple logistic regression was used to adjust fibrinogen γ' levels (quartiles) for high levels of total fibrinogen (quartiles) and the risk genotype/haplotype (FGG-H2). The tenth percentile (P10) of the γ'/γ ratio, measured in the control subjects, was used as cut-off point to assess whether a low γ'/γ ratio was associated with the risk of venous thrombosis.

Results

Genotyping of all 942 subjects showed that the 15 selected htSNPs identified four haplotypes of FGG, five of FGA and six of FGB (see FIG. 3). For all htSNPs, the distribution of the genotypes in the control subjects was in Hardy-Weinberg equilibrium. Inspection of the genotypic data by Haploview revealed, as expected, a high degree of linkage disequilibrium between the SNPs of the three different fibrinogen genes (data not shown). The Arlequin output showed that haplotypes were continuous over the gene-cluster. In Table 3 the continuous haplotypes with an allele frequency >1% in the control subjects are shown. Most recombination was present between the FGB and the FGA gene.

TABLE 3

The continuous haplotypes with allele frequencies >1%

| FGG-FGA-FGB | Frequency controls |
|---|---|
| H1-H1-H1 | 21.1 |
| H1-H1-H4 | 1.6 |
| H1-H4-H1 | 1.9 |
| H1-H4-H4 | 7.8 |
| H1-H4-H5 | 1.8 |
| H2-H2-H1 | 5.5 |
| H2-H2-H2 | 16.7 |
| H2-H2-H4 | 3.7 |
| H3-H3-H3 | 10.3 |
| H3-H7-H1 | 1.2 |
| H3-H7-H4 | 1.2 |
| H3-H7-H6 | 14.4 |
| H4-H1-H1 | 2.7 |

In all three genes, subjects homozygous for one of the haplotypes, all designated H2, had an increased thrombosis risk compared to all other subjects (Table 4a).

TABLE 4a

Thrombosis risk of haplotypes of FGG, FGA and FGB

| | FGG | | | FGA | | | FGB | | |
|---|---|---|---|---|---|---|---|---|---|
| Haplotype | cases (%) | controls (%) | OR* (95% CI) | cases (%) | controls (%) | OR* (95% CI) | cases (%) | controls (%) | OR* (95% CI) |
| Haplotype 1 | | | | | | | | | |
| H1Hx | 222 (47.3) | 236 (50.1) | 0.8 (0.6-1.1) | 192 (41.0) | 200 (42.5) | 1.0 (0.7-1.3) | 212 (45.3) | 210 (45.1) | 1.1 (0.8-1.4) |
| H1H1 | 56 (11.9) | 65 (13.8) | 0.8 (0.5-1.2) | 33 (7.0) | | 1.2 (0.7-2.0) | 58 (12.4) | 50 (10.7) | 1.2 (0.8-1.9) |
| Haplotype 2 | | | | | | | | | |
| H2Hx | 201 (42.8) | 198 (42.0) | 1.2 (0.9-1.5) | 200 (42.7) | 202 (42.9) | 1.1 (0.9-1.5) | 165 (35.3) | 151 (32.4) | 1.2 (0.9-1.6) |
| H2H2 | 57 (12.2) | 28 (6.0) | 2.4 (1.5-3.9) | 60 (12.8) | 34 (7.2) | 2.0 (1.3-3.2) | 33 (7.1) | 19 (4.1) | 1.9 (1.1-3.4) |
| Haplotype 3 | | | | | | | | | |
| H3Hx | 185 (39.4) | 211 (44.8) | 0.8 (0.6-1.0) | 85 (18.2) | 103 (21.9) | 0.8 (0.6-1.1) | 78 (16.7) | 95 (20.4) | 0.8 (0.6-1.1) |
| H3H3 | 32 (6.8) | 39 (8.3) | 0.7 (0.4-1.2) | 5 (1.1) | 7 (1.5) | 0.7 (0.2-2.2) | 5 (1.1) | 5 (1.1) | 1.0 (0.3-3.3) |
| Haplotype 4 | | | | | | | | | |
| H4Hx | 38 (8.1) | 32 (6.8) | 1.2 (0.7-2.0) | 94 (20.1) | 101 (21.4) | 0.9 (0.7-1.2) | 119 (25.4) | 123 (26.4) | 0.9 (0.7-1.3) |
| H4H4 | 1 (0.2) | 0 (0.0) | — | 3 (0.6) | 10 (2.1) | 0.3 (0.1-1.1) | 8 (1.7) | 13 (2.8) | 0.6 (0.2-1.5) |
| Haplotype 5 | | | | | | | | | |
| H5Hx | | NP | | | NP | | 11 (2.4) | 16 (3.4) | 0.7 (0.3-1.5) |
| H5H5 | | NP | | | NP | | 0 (0.0) | 1 (0.2) | — |

TABLE 4a-continued

Thrombosis risk of haplotypes of FGG, FGA and FGB

| | FGG | | | FGA | | | FGB | | |
|---|---|---|---|---|---|---|---|---|---|
| Haplotype | cases (%) | controls (%) | OR* (95% CI) | cases (%) | controls (%) | OR* (95% CI) | cases (%) | controls (%) | OR* (95% CI) |
| Haplotype 6 | | | | | | | | | |
| H6Hx | | | | | NP | | 114 (24.4) | 131 (28.1) | 0.8 (0.6-1.1) |
| H6H6 | | | | | NP | | 7 (1.5) | 6 (1.3) | 1.1 (0.4-3.3) |
| Haplotype 7 | | | | | | | | | |
| H7Hx | | | | 129 (27.6) | 142 (30.1) | 0.9 (0.6-1.2) | 13 (2.8) | 16 (3.4) | 0.8 (0.4-1.7) |
| H7H7 | | | | 11 (2.4) | 13 (2.8) | 0.8 (0.4-1.9) | 1 (0.2) | 1 (0.2) | 1.0 (0.1-15.9) |

Because the haplotypes in these genes will not be inherited independently, it is difficult to identify the gene (and subsequently the SNP) responsible for the effect on thrombosis. Therefore, the ORs and 95% CIs of both the risk haplotype (H2) and the protective haplotype (H3) of each gene were calculated by means of multiple logistic regression. By entering the three separate haplotypes of a continuous haplotype (e.g. FGG-H2, FGA-H2 and FGB-H2) in one model, it is possible to correct the effect of a haplotype of one gene for that of the haplotypes of the other two genes. The risk associated with FGA-H2H2 (OR=0.5, 95% CI-0.2-1.9) and FGB-H2H2 (OR=1.3, 95% CI-0.6-2.8) almost completely disappeared, but the risk associated with FGG-H2H2 remained (OR=3.5, 95% CI:1.0-12.5). From this we conclude that the causal mutation of H2 must be located somewhere in the FGG gene. For H3 the risk reduction only remained in FGG-H3H3 (Table 4b).

TABLE 4b

ORs of haplotypes H2 and H3 of a gene after adjustment for the effects of respectively haplotypes H2 or H3 of the other genes

| Haplotype | FGG OR (95% CI)* | FGA OR (95% CI)* | FGB OR (95% CI)* |
|---|---|---|---|
| Haplotype 2 | | | |
| H2Hx | 1.7 (0.8-3.7) | 0.6 (0.3-1.4) | 1.1 (0.8-1.6) |
| H2H2 | 3.5 (1.0-12.5) | 0.5 (0.1-1.9) | 1.3 (0.6-2.8) |
| Haplotype 3 | | | |
| H3Hx | 0.7 (0.5-1.0) | 1.3 (0.7-2.4) | 0.8 (0.4-1.4) |
| H3H3 | 0.7 (0.3-1.3) | 1.1 (0.3-4.4) | 1.4 (0.3-1.7) |

*All ORs were calculated with HxHx as reference category, OR = 1
Hx: All haplotypes but the one given
Adjustment for linkage disequilibrium by multiple logistic regression Since increased fibrinogen levels are associated with the risk of DVT, it was first investigated in the control subjects whether haplotypes of FGG, FGA and FGB were associated with plasma levels of fibrinogen. In Table 5, the mean fibrinogen levels of homozygous carriers of the various haplotypes are shown. None of the haplotypes was associated with plasma fibrinogen levels.

TABLE 5

Association of FGG, FGA and FGB haplotypes and fibrinogen levels (U/dL) in homozygous carriers (controls)

| Haplotype | N | Mean | (95% CI) |
|---|---|---|---|
| FGG | | | |
| H1H1 | 65 | 320 | (306-334) |
| H2H2 | 28 | 311 | (292-329) |
| H3H3 | 39 | 318 | (301-334) |
| FGA | | | |
| H1H1 | 33 | 329 | (304-354) |
| H2H2 | 34 | 313 | (297-330) |
| H3H3 | 7 | 324 | (281-367) |
| H4H4 | 10 | 336 | (285-387) |
| H7H7 | 13 | 315 | (280-350) |
| FGB | | | |
| H1H1 | 50 | 320 | (301-339) |
| H2H2 | 19 | 335 | (311-360) |
| H3H3 | 5 | 313 | (260-365) |
| H4H4 | 13 | 324 | (290-359) |
| H5H5 | 1 | 281 | |
| H6H6 | 6 | 283 | (243-323) |
| H7H7 | 1 | 282 | |

Since no quantitative effect on plasma fibrinogen levels of any of the FGA, FGB and FGG haplotypes was observed, FGG-H2 (which increased the risk of thrombosis) should contain a qualitative defect, i.e. a SNP that alters the amino acid sequence and by that some functional property of the fibrinogen gamma chain. Since none of the four FGG H2-tagging SNPs that were determined in the FGG gene changed the amino acid sequence, the possibility was considered that part of the FGG-H2 carriers had an additional variation in the coding region of the FGG gene. The genes of ten DVT patients homozygous for FGG-H2 (20 FGG-H2 alleles) were therefore sequenced over the complete gene-cluster, including the promoters, 5'UTRs, exons, intron/exon boundaries and 3'UTRs, but no novel variations were found. This indicated that one of the four SNPs that is specific for FGG-H2 in this study is the risk enhancing SNP.

One of these four FGG-H2 specific SNPs is located in the promoter (129 A/T [rs2066854], one in intron 8 (7874 G/A [rs2066861]), one in intron 9 (9615 C/T [rs2066864]) and one downstream from the 3' untranslated region (10034 C/T [rs2066865]). It was reasoned by the inventors that these last two SNPs (9615 C/T or 10034 C/T) influenced the efficiency of alternative splicing of the FGG pre-mRNA by their close proximity to the polyadenylation sites of the fibrinogen γ' and γA transcripts, respectively, and therefore alter fibrinogen γ' expression (FIG. 2)

The gamma chain exists in two forms, γA and γ' (FIG. 2). The γA chain is translated from an mRNA in which all 9 introns of the pre-mRNA have been removed. In contrast, the γ' chain arises from alternative processing of the FGG pre-mRNA. Intron 9 is not spliced out and polyadenylation occurs within this intron. This leads to the translation of a polypeptide with a unique 20-amino acid extension encoded by intron 9 substituted for the carboxyl-terminal four amino acids encoded by exon 10. This variant chain comprises approximately 7-15% of the fibrinogen γ chain found in plasma. Nearly all of the γ' protein occurs in vivo as a heterodimer with the γA variant where one D region contains a γ' carboxyl terminus and the other a γA carboxyl terminus.

FGG-H2, which contains both 9615 T and 10034 T, is associated with γ' formation and γ' formation effects thrombosis risk. To identify possible recombinations between H2-specific SNPs 7874 G/A, and 10034 C/T, all subjects were also typed for SNP 10034 C/T. The finding that 10034 C/T was completely linked to 7874 G/A excluded the possibility of recombinations between SNPs 7874 G/A and 10034 C/T.

Fibrinogen γ' (i.e. γA/γ' and γ'γ') levels were measured in 473 patients and 474 controls by ELISA. FGG-H2, which was identified by the inventors as risk haplotype, was strongly associated with reduced fibrinogen γ' levels (Table 6). There was a clear allele specific and dosage dependent effect of the FGG-H2 haplotype on fibrinogen γ' levels with homozygous H2 carriers having the lowest levels and intermediate values for carriers of one H2-alelle. Additionally, FGG-H3 alleles were associated with increased fibrinogen γ' levels.

TABLE 6

Association of FGG haplotypes with absolute and normalized fibrinogen γ' levels

| Haplotype FGG | N | Absolute fibrinogen γ' levels Mean (95% CI) | Normalized fibrinogen γ' levels Median | Range | Mean (95% CI) | Median | Range |
|---|---|---|---|---|---|---|---|
| H2H2 | 28 | 0.67 (0.59-0.76) | 0.61 | 0.34-1.22 | 0.60 (0.55-0.65) | 0.58 | 0.36-0.96 |
| H1H2 | 106 | 0.96 (0.90-1.01) | 0.93 | 0.49-1.70 | 0.81 (0.79-0.84) | 0.82 | 0.53-1.07 |
| H2H3 | 83 | 1.03 (0.95-1.11) | 0.95 | 0.53-2.48 | 0.89 (0.86-0.92) | 0.88 | 0.62-1.35 |
| H2H4 | 8 | 0.85 (0.70-1.01) | 0.95 | 0.60-1.05 | 0.81 (0.71-0.90) | 0.77 | 0.69-1.00 |
| H2H5 | 1 | 1.09 | | | 0.73 | | |
| H1H1 | 65 | 1.13 (1.06-1.20) | 1.10 | 0.62-1.91 | 0.99 (0.95-1.02) | 0.97 | 0.69-1.47 |
| H1H4 | 13 | 1.23 (1.06-1.40) | 1.24 | 0.87-1.64 | 1.06 (0.96-1.16) | 1.01 | 0.88-1.47 |
| H1H3 | 117 | 1.31 (1.25-1.38) | 1.26 | 0.59-2.27 | 1.09 (1.05-1.12) | 1.07 | 0.63-1.65 |
| H3H3 | 39 | 1.31 (1.22-1.40) | 1.32 | 0.88-1.92 | 1.15 (1.11-1.19) | 1.15 | 0.84-1.41 |
| H3H4 | 11 | 1.40 (1.20-1.60) | 1.38 | 0.97-2.12 | 1.10 (1.00-1.21) | 1.05 | 0.93-1.52 |

There was no difference in fibrinogen γ' levels between patients (mean: 111 U/dL, 95% CI: 107-115) and controls (mean: 111 U/dL, 95% CI: 108-114). To assess whether reduced fibrinogen γ' levels were associated with an increased risk of venous thrombosis, quartiles as measured in the control subjects were used as cut-off points. Reduced fibrinogen γ' levels (lowest quartile) were associated with a slightly increased risk (OR=1.3, 95% CI:0.9-1.8) compared to the highest quartile (Table 7a) However, the fibrinogen γ' level is not only determined by the splicing and polyadenylation efficiency of the FGG pre-mRNA, but also by the rate of fibrinogen synthesis, consumption and clearance. Indeed a good correlation between total fibrinogen levels and fibrinogen γ' levels was found (FIG. 4).

TABLE 7a

Thrombosis risk of fibrinogen γ' levels (U/dL) and
total fibrinogen levels (U/dL) in quartiles as measured in
control subjects

|  | A<br>$OR_{crude}$ (95% CI) | B<br>$OR_{adjusted}$ (95% CI)† | C<br>$OR_{adjusted}$ (95% CI)† |
|---|---|---|---|
| Fibrinogen γ' levels | | | |
| ≧132 | 1* | 1* | 1* |
| 109-132 | 0.8 (0.6-1.2) | 1.2 (0.8-1.8) | 1.2 (0.8-1.9) |
| 86-109 | 0.9 (0.6-1.3) | 1.9 (1.2-3.0) | −1.9 (1.1-3.0) |
| <86 | 1.3 (0.9-1.8) | 3.0 (1.8-4.9) | 2.9 (1.6-5.4) |
| Total fibrinogen levels | | | |
| <101 | 1* | 1* | 1* |
| 101-114 | 0.9 (0.6-1.3) | 1.1 (0.7-1.6) | 1.0 (0.7-1.5) |
| 114-130 | 1.0 (0.7-1.5) | 1.6 (1.1-2.5) | 1.6 (1.0-2.4) |
| ≧130 | 1.5 (1.1-2.2) | 3.2 (2.0-5.2) | 3.2 (1.8-5.4) |
| FGG haplotype 2 | | | |
| HxHx | 1* | — | 1* |
| H2Hx | 1.2 (0.9-1.5) | — | 0.9 (0.6-1.2) |
| H2H2 | 2.4 (1.5-3.9) | — | 1.4 (0.8-2.5) |

*Reference category
†OR adjusted for each other by multiple logistic regression

Therefore the inventors calculated the risk of venous thrombosis stratified for quartiles of fibrinogen γ' levels and for quartiles of total fibrinogen levels (as measured in controls) (Table 8). In each total fibrinogen quartile the risk of venous thrombosis increased when fibrinogen γ' levels decreased, while in each fibrinogen γ' quartile the thrombosis risk increased when total fibrinogen levels increased. This showed that reduced fibrinogen γ' levels and elevated fibrinogen levels were two separate risk factors for venous thrombosis. To confirm these findings, we used logistic regression to calculate the risk of venous thrombosis for quartiles of fibrinogen γ' levels and for quartiles of total fibrinogen levels. This analysis showed that both reduced fibrinogen γ' levels and increased total fibrinogen levels were associated with an increased risk of venous thrombosis (Table 7a, column B).

TABLE 8

Thrombosis risk (OR and 95% CI) after stratification
for quartiles of fibrinogen γ' and total fibrinogen as measured
in control subjects

| Total fibrinogen | Fibrinogen γ' | | | | | | | |
|---|---|---|---|---|---|---|---|---|
| | <86 | | 86-108 | | 109-131 | | ≧132 | |
| | Ca | Co | Ca | Co | Ca | Co | Ca | Co |
| <101 | 68 | 69 | 32 | 36 | 5 | 13 | 2 | 0 |
| | OR = 1* | | 0.9 (0.5-1.6) | | 0.4 (0.1-1.2) | | — | |
| 101-113 | 43 | 34 | 29 | 44 | 16 | 29 | 1 | 9 |
| | 1.3 (0.7-2.3) | | 0.7 (0.4-1.2) | | 0.6 (0.3-1.1) | | 0.1 (0.0-0.9) | |
| 114-129 | 28 | 13 | 32 | 30 | 32 | 50 | 19 | 27 |
| | 2.2 (1.0-4.6) | | 1.1 (0.6-2.0) | | 0.6 (0.4-1.1) | | 0.7 (0.4-1.4) | |
| ≧130 | 9 | 1 | 16 | 9 | 43 | 27 | 93 | 80 |
| | 9.1 (1.1-74.1) | | 1.8 (0.7-4.4) | | 1.6 (0.9-2.9) | | 1.2 (0.8-1.9) | |

*Reference category;
Ca: number of cases,
Co: number of controls

Since FGG-H2 was associated with reduced fibrinogen γ' levels and an increased risk of DVT, FGG-H2 together with quartiles of fibrinogen γ' and quartiles of fibrinogen were entered in the same model (Table 7a, column C). The risks associated with both reduced fibrinogen γ' levels and elevated total fibrinogen levels did not change, while the risk associated with FGG-H2 homozygosity almost completely disappeared (OR=1.4, 95% CI: 0.8-2.5). This indicates that the effect of FGG-H2 is mediated by its effect on the fibrinogen γ' level.

Because the plasma concentration of fibrinogen γ' and of total fibrinogen both influence thrombotic risk and because the fibrinogen γ' level depends always on the total fibrinogen level, the effect of the fibrinogen γ'/total fibrinogen ratio (γ'/γ ratio) on the risk of venous thrombosis was also analysed. It was found that the γ'/γ ratio was lower in patients (mean: 0.89, 95% CI: 0.87-0.92) than in controls (mean: 0.95, 95% CI: 0.93-0.97). Individuals with γ'/γ ratio below 0.69, which represents the tenth percentile (P10) as measured in the control subjects, have an increased risk of venous thrombosis (OR=2.4, 95% CI: 1.7-3.5) compared to those with a γ'/γ ratio ≧0.69 (Table 7b). FGG-H2 was associated with reduced fibrinogen γ' levels, but also with a reduced γ'/γ ratio (Table 6). FGG-H2 was entered together with the P10 of the γ'/γ ratio in the same logistic regression model. The risk associated with a reduced γ'/γ ratio (<0.69) remained (OR=2.2, 95% CI: 1.3-3.5), while the risk associated with FGG-H2 homozygosity largely disappeared (OR=1.2, 95% CI: 0.6-2.3). This shows that the FGG-H2 haplotype acts on the risk of venous thrombosis via reduction of the γ'/γ ratio.

TABLE 7b

Thrombosis risk of the tenth percentile (P10) of the
γ'/γ ratio as measured in control subjects

| | Cases (%)<br>N = 473 | Controls (%)<br>N = 474 | OR | 95% CI |
|---|---|---|---|---|
| ≧0.69 | 373 (78.9) | 427 (90.1) | 1* | — |
| <0.69 | 100 (21.1) | 47 (9.9) | 2.4 | 1.7-3.5 |

*Reference category

Discussion

The effect of the most common haplotypes of the FGG, FGA and FGB genes on the risk of venous thrombosis was investigated in a large population based case control study, the Leiden Thrombophilia Study. Three haplotypes were found to increase the risk of thrombosis, FGG-H2, FGA-H2 and FGB-H2. After adjustment for linkage disequilibrium between the three genes, only the FGG-H2 haplotype remained associated with an increased risk of venous thrombosis. Homozygous carriers of the FGG-H2 haplotype (5.9% of the population) had a 2.4 (95% CI: 1.5-3.9) fold increased risk to develop a first venous thrombotic event. The FGG-H2 haplotype was also found to be associated with reduced plasma fibrinogen γ' levels (γA/γ' plus γ'/γ' fibrinogen) and with a reduced fibrinogen γ'/total fibrinogen ratio (γ'/γ ratio).

It was further found that the risk of venous thrombosis increases dose dependently with increasing levels of fibrinogen and decreasing levels of fibrinogen γ', even after adjustment for the presence of the FGG-H2 haplotype. It was concluded that the FGG-2 haplotype increases the risk of venous thrombosis by decreasing the plasma level of fibrinogen γ'. Because fibrinogen γ' levels are associated with fibrinogen levels (FIG. 5) and because elevated fibrinogen levels are also associated with an increased risk of venous thrombosis, it was considered more practical to use the γ'/γ ratio as a risk determinant. Individuals with a γ'/γ ratio below the P10 of the distribution as measured in healthy subjects (0.69) had a 2.4-fold increased risk of venous thrombosis even after adjustment for the FGG-H2 haplotype. 82% of the controls and 91% of the cases with γ'/γ<0.69 were homozygous carriers of the FGG-H2 haplotype.

The risk haplotype FGG-H2 is defined by four completely linked polymorphisms, of which the rare allele is unique for this haplotype: 129 A/T (rs2066854), 7874 G/A (rs2066861), 9615 C/T (rs2066864) and 10034 C/T (rs2066865). The rs numbers identify the SNPs according to the dbSNP (accessible via http://www.ncbi.nlm.nih.gov). Also, in the present study population of 940 individuals no recombination was found between the 7874 G/A and 10034 C/T polymorphisms. It is proposed by the inventors that it is the 10034 C>T change which results in reduced plasma fibrinogen γ' and a reduced γ'/γ ratio because it improves a CstF consensus site.

FGG-H2 was identified as the only haplotype associated with an increased risk of venous thrombosis, while none of the FGG, FGA or FGB haplotypes was associated with plasma fibrinogen levels in healthy control subjects. Thus, testing for the FGG-H2 can be used as a diagnostic tool.

Example 2

The T Allele of the Fibrinogen Gamma 10034C>T Polymorphism Reduces the Efficiency of Alternative Splicing of the Fibrinogen Gamma Gene by Strengthening the Consensus for the CstF Site at Nucleotides 10030-10047 in the FGG Gene
Introduction In Example 1 it was reported that a haplotype of the fibrinogen gamma gene (FGG-H2) was associated with an increased risk of deep venous thrombosis and with reduced fibrinogen γ' levels. After inspection of FGG-H2 for the haplotype tagging single nucleotide polymorphisms (htSNPs) present in this haplotype, it was hypothesised that the T allele of the 10034C>T polymorphism [rs2066865] (Numbering according to SeattleSNPs (Nickerson D. SeattleSNPs. NHLBI Program for Genomic Applications, UW-FHCRC, Seattle, Wash. http://pga.gs.washington.edu. 15-4-2003), GenBank Accession number AF350254 was responsible for the reduction in fibrinogen γ' levels by influencing the efficiency of alternative splicing of the fibrinogen gamma gene.

The 10034C>T polymorphism is located in a Cleavage stimulatory Factor (CstF) consensus 2a (Beyer K et al., J Biol Chem. (1997) 272:26769-26779) sequence (YGTGTYT-TYAYTGNNYGT at nt 10030-10047) just downstream from the second polyadenylation (pA) signal (nt 9997-10002 (pA2); FIG. 8. This polyadenylation signal is used for the formation of the mRNA encoding the fibrinogen γA chain. The polyadenylation signal used for the formation of the mRNA encoding the fibrinogen γ' chain (pA1) is located in intron 9 at nt 9558-9563. In FGG-H2, which contains a T at nucleotide 10034 (underlined in the CstF consensus sequence), the CstF sequence is strengthened compared to that of the other common FGG haplotypes (H1, H3, and H4), which all have a C at position 10034.

It was hypothesised that this improvement of the CstF consensus results in more frequent use of the polyadenylation signal at nt 9997-10002 (pA2) in pre-mRNAs derived from the FGG-H2 allele and that as a consequence pA1 (γ' specific polyadenylation) is relatively less frequently used. FGG-H2 is therefore expected to produce relatively more γA transcripts (using pA2) and relatively less γ' transcripts (using pA1), which would correspond with the reduced fibrinogen γ' levels and fibrinogen γ'/total fibrinogen ratios observed in homozygous carriers of FGG-H2 in vivo.

There is one additional polymorphism located in intron 9, which is specific to FGG-H2 and which based on its position might influence the efficiency of alternative splicing of the fibrinogen gamma gene. The 9615C>T [rs2066864] polymorphism is located in a position 3' from the first polyadenylation signal at nt 9558-9563 (pA1) in intron 9, that leads to the fibrinogen γ' specific transcript.

To investigate the role of polymorphisms 9615C>T and 10034C>T on the efficiency of alternative splicing of the fibrinogen gamma pre-mRNA, different FGG mini-gene constructs (see Table 9) were made and transfected in liver derived HepG2 cells. After transfection, mRNAs were isolated from the cells and the relative use of pA1 and pA2 estimated, as a measure for the efficiency of alternative splicing, for each of the different constructs by real time PCR. To confirm the importance of the CstF consensus sequence at nt 10030-10047 in determining the efficiency of alternative splicing of the FGG pre-mRNA, the CstF consensus at nt 10030-10047 was additionally strengthened and weakened by introducing mutations at other positions based on the same consensus sequence (see Table 10).

Methods
1. FGG Haplotype Mini-gene Constructs

Mini-gene constructs used in this study were based on expression vector pcDNA3 (Invitrogen), containing a strong CMV promoter. A 1090 bp fragment containing exon 9, intron 9, exon 10 and the 3'UTR of the fibrinogen gamma gene was amplified by PCR with high fidelity polymerase (Taq/Tgo mixture, Roche) on genomic DNA samples homozygous for FGG-H1 and FGG-H2. The forward primer (5'-GTC GAT CGG TCTAGA CCA CCA TGG GTG GCA CTT ACT CAA AAG CAT C-3' (SEQ ID NO:29)) contained a Kozak sequence with a translation start site (italic) and an introduced restriction site for XbaI (underlined). The startcodon, which is in frame with the natural reading frame of exon 9, was introduced to prevent potential problems with nonsense mediated decay of the spliced mRNAs. The reverse primer (5'-CAA CTA GAA TGCAAA GAG TTA GGC ATA ACA TTT AGC A-3' (SEQ ID NO:30) contained an introduced restriction site for BsmI (underlined).

PCR products and vector were double digested with XbaI and BsmI and PCR products were cloned into the XbaI and BsmI sites of the vector. By double digestion with XbaI and BsmI, the Bovine Growth Hormone and SV40 polyadenylation sites were removed from the vector to prevent interference with the experiments.

Several different FGG mini-gene constructs were made (Table 9). Construct 1 (9615C, 10034C (FGG-H1)) and construct 2 (9615T, 10034T (FGG-H2)) each carried a haplotype of FGG. Construct 3 (9615C, 10034T) and construct 4 (9615T, 10034C) were derived by the exchange of the HindIII restriction fragment between constructs 1 and 2, using a HindIII site upstream of the fragment in the vector and an internal HindIII site at nt 9908-9913 of the insert.

TABLE 9

FGG mini-gene construct variants

| Construct | FGG haplotype | SNP 9615 | SNP 10034 |
|---|---|---|---|
| 1 (wild type) | H1 | C | C |
| 2 | H2 | T | T |
| 3 | — | C | T |
| 4 | — | T | C |

All constructs were analysed by sequencing to verify the identity of the polymorphic sites and to make sure that no PCR artefacts had been introduced. Sequencing was performed on an ABI PRISM® 3100 Genetic Analyzer (Applied Biosystems). Reactions were performed using the ABI PRISM® BigDye Terminator Cycle Sequencing kit (Applied Biosystems). Primer sequences are listed in the table below.

```
Sequence primers (5'-3')
pcDNA3Fw        TCACTATAGGGAGACCCAAGC
                (SEQ ID NO: 31)

pcDNA3Rv        ACCATGATTACGCCAAGCTC
                (SEQ ID NO: 32)

FGGex9-10Rv     GCTTTGCAAGTCCATTGTCC
                (SEQ ID NO: 33)

seqmut1Fw       AAAATAGGAGAACATTTTAGGTTTCAA
                (SEQ ID NO: 34)

seqmut1Rv       GCTGAATGAAGCCATACCAAA
                (SEQ ID NO: 35)

seqmut2Fw       TAGAGCTTGGCGTAATCATGG
                (SEQ ID NO: 36)

seqmut2Rv       TTTTTCTGCGCGTAATCTGC
                (SEQ ID NO: 37)
```

2. CstF Consensus Mutagenesis

Site directed mutagenesis was performed using the Quikchange™ site directed mutagenesis kit (Stratagene) according to the manufacturer's protocol. In total, four CstF consensus mutants were made (Table 10). In CstF mutant 1, 10031G was mutated into an A. In CstF mutant 2, both 10031G and 10042G were mutated into an A. In CstF mutant 3, 10033A was mutated into a G and in CstF mutant 4, both 10033A and 10046A were mutated into a G.

TABLE 10

FGG mini-gene constructs with mutations in the CstF site

| Construct | mutations in CstF consensus | SNP 9615 | SNP 10034 |
|---|---|---|---|
| wild type | no | C | C |
| mutant 1 | 10031G > A | C | C |
| mutant 2 | 10031G > A; 10042G > A | C | C |
| mutant 3 | 10033A > G | C | C |
| mutant 4 | 10033A > G; 10046A > G | C | C |

The following mutant oligos were used (mutated nucleotides are underlined): CstF mutant 1: 5'-GAC TAG ATA CAT GAT ACC TTT ATT GAC CAT TAA AAA CCA CC-3' (SEQ ID NO:38) and reversed complementary, CstF mutant 2: 5'-GAC TAG ATA CAT GAT ACC TTT ATT AAC CAT TAA AAA CCA CC-3' (SEQ ID NO:39) and reversed complementary, CstF mutant 3: 5'-GAC TAG ATA CAT GGT GCC TTT ATT GAC CAT TAA AAA CCA CC-3' (SEQ ID NO:40) and reversed complementary, CstF mutant 4: 5'-GAC TAG ATA CAT GGT GCC TTT ATT GAC CGT TAA AAA CCA CC-3' (SEQ ID NO:41) and reversed complementary. To verify the mutations, all mutated constructs were analysed by sequencing.

3. Transfection Conditions

Constructs were transfected into HepG2 cells. The human Caucasian hepatocyte hepatoma cell line HepG2 (ECACC, #85011430), which produces endogenous fibrinogen, was cultured according to the instructions of the ECACC. Cells were cultured in 12 well plates and transfections were performed after 24 hours at 60-80% confluency using the Tfx-20 reagent (Promega), according to the manufacturer's protocol. 1 µg of each construct was transfected using 3 µl Tfx-20 reagent in a total volume of 400 µl growth medium (MEM supplemented with 10% (v/v) foetal calf albumin, 60 U/ml penicillin/streptomycin and 0.1 mM non-essential amino acids). Since each construct produced both transcripts (γA and γ'), there was no need to correct for differences in transfection efficiency. Three independent transfection experiments were performed using two separate construct preparations.

4. Total RNA Isolation

After harvesting the cells by trypsinisation, total RNA was isolated using the RNeasy mini kit (Qiagen), according to the manufacturer's protocol. Each RNA sample was incubated with 10 units DNase I (Roche) for 15 min at 37° C., followed by 15 min of inactivation at 65° C. The quality of each total RNA sample was checked by agarose gel electrophoresis.

5. cDNA Synthesis cDNA synthesis was performed using a first-strand cDNA synthesis kit for reverse transcriptase (RT) (SuperScript™ II Reverse Transcriptase, Invitrogen) and 1 µg RNA from HepG2 cells according to the protocol, except that a modified oligo d(T) primer (5'-AGC TGG TCA GTC GTC AGC TGA (T)16-3' (SEQ ID NO:42)) was used. With this primer, only mRNA could be used as template for cDNA synthesis.

6. Real Time PCR Analysis

For each sample, the efficiency of alternative splicing was measured by real-time PCR using fluorescently labelled probes. To prevent formation of heteroduplexes, the concentration of pA1 and pA2 transcripts in two separate PCR reactions were analysed. In both reactions, the forward primer (5'-TGC AGA TAT CCA TCA CAC TGG-3' (SEQ ID NO:43)) was located on the vector, to amplify only the cDNAs derived from the construct transcripts, without amplification of the endogenous fibrinogen mRNAs.

For the measurement of pA2 transcripts, the reverse primer (5'-GAA GTG AAG CTT TGC AAG TCC-3' (SEQ-ID NO:44)) was located in the 3'UTR of FGG (see FIG. 9). The probe specific for the pA2 transcript (5'-FAM-GAC GTT TAA AAG ACC GTT TCA AA-BHQ-3' (SEQ ID NO:45)) was located on the boundary of exon 10 and the 3'UTR (FIG. 9). For the measurement of pA1 transcripts, the reverse primer (5'-TCA TCC TCA GGG TAA AGT GAG TC-3' (SEQ ID NO:46)) was located in that part of intron 9 that encodes the 20 additional amino acids of the γ' chain carboxyterminus (FIG. 9). The probe specific for the pA1 transcript (5'-TET-AGG TCA GAC CAG AGC ACC CT-BHQ-3' (SEQ ID NO:47)) was located on the boundary of exon 9 and the 20 additional amino acids of the γ' chain carboxyterminus (FIG. 9). The sizes of the products were 340 bp (γA) and 280 bp (γ').

Real-Time PCR efficiencies were calculated from the slopes of a serially diluted cDNA preparation. The corresponding real-time PCR efficiency (E) of one cycle in the exponential phase was calculated according to the equation: $E=10^{[-1/slope]}$ (Pfaffl MW. Nucleic Acids Res. 2001; 29:e45). Both the pA2- and pA1-transcripts showed a real time PCR efficiency rate of 2.14 in the investigated range from undiluted to $10^{-5}$ diluted cDNA input (n=6) with high linearity (Pearson correlation coefficient r>0.98).

Quantitative values were obtained from the threshold cycle number at which the fluorescence generated within a reaction crosses the threshold (Ct value). In both reactions fixed thresholds were chosen at a point at which amplification was in the exponential phase (0.25 for the γA-reaction and 0.10 for the γ'-reaction). The function $2^{-\Delta Ct}$ was used as a measure for the ratio pA1-transcript/pA2-transcript, where ΔCt is the difference between $Ct_{pA1}$ and $Ct_{pA2}$.

To confirm accuracy and reproducibility of the real time PCR, each cDNA sample was analysed three times within one run, and in four different runs. Ct values were approved when the intra-assay CV was <1%. The inter-assay CV was <4%. Two different DNA preparations of all the constructs were compared in three independent transfection experiments.

7. Statistical Analysis

To analyse the differences in expression of pA1 and pA2 transcripts between constructs, the relative expression of pA1-transcript to pA2 transcript(pA1/pA2 ratio) of the haplotype 1 carrying construct (9615C, 10034C) was set at 100% (wild type construct). In this way, the pA1/pA2 for constructs with increased use of pA2 will be lower than 100%. Conversely, the pA1/pA2 ratio for constructs with decreased use of pA2 will be higher than 100%. Mean relative pA1/pA2 ratios of all constructs were tested for differences with the wild type construct using two sided Student's t-test.

Results

1. FGG Haplotype Mini-gene Constructs

The mean relative use of pA1 and pA2 transcripts (pA1/pA2 ratio) for the different FGG mini gene constructs as compared to the wild type construct (construct 1, FGG-H1) is shown in FIG. 10. The pA1/pA2 ratio for construct 2 (FGG-H2) was decreased compared to that obtained for the wild type construct (71.5 12%, p<0.001). This corresponded to our previous finding that FGG-H2 is associated with decreased fibrinogen γ' levels in vivo. Since FGG-H2 contains two SNPs in the region of alternative splicing (9615C>T and 10034C>T)1, exchange constructs 3 (9615C, 10034T) and 4 (9615T, 10034C) were made. These haplotypes do not occur in vivo, but these constructs were made to determine which one of the two FGG-H2 specific SNPs causes the reduction in fibrinogen γ' expression.

The pA1/pA2 ratio for construct 3 was decreased compared to that obtained for the wild type construct (85.3 3.3%, p=0.007), while the ratio for construct 4 did not differ significantly from that for the wild type construct (101.6 18.4%, p=0.881). This indicated that a T in position 10034 decreased the relative use of pA1 compared to a C in this position.

These data demonstrate that the 10034 C>T change is responsible for the relative increased use of pA2 and decreased use of pA1, and therefore for the reduced γ' content, which we previously found to be associated with the risk of venous thrombosis.

2. CstF Consensus Mutant Constructs

To support the CstF consensus used to predict the functionality of the T allele of SNP 10034, constructs were made in which the CstF consensus was mutated in other positions (see Table 10). In CstF mutant 1, 10031G was mutated into an A. Hypothetically, this nucleotide change would favor the use of pA1 by reducing the use of pA2, since this mutation weakens the CstF consensus. This would also be true for CstF mutant 2, in which both 10031G and 10042G were mutated into an A. In CstF mutants 0.3 and 4 an increase in the use of pA2 and consequently a decrease in the use of pA1 decrease in fibrinogen γ' expression would be expected, since in these mutants the CstF consensus was strengthened by one or two nucleotides. In CstF mutant 3, 10033A was mutated into a G and in CstF mutant 4, both 10033A and 10046A were mutated into a G.

FIG. 11 shows the mean relative use of pA1 and pA2 for the CstF mutant constructs compared to the wild type construct (9615C, 10034C). In CstF mutants 1 (142.4%) and 2 (160.7%) pA1 was used relatively more frequent than in the wild type construct (1: p=0.008, 2: p<0.001). In contrast, in CstF mutants 3 (66.2%) and 4 (59.7%) the relative use of pA1 is decreased compared to that in the wild type construct (3: p<0.001, 4: p<0.001). These data demonstrate that the 10034C is part of a functional CstF consensus site.

Example 3

Method for Determining the Presence of Haplotype FGG-H2 in a Subject

One method that can be used to demonstrate the presence of the FGG-H2 haplotype in an individual is to genotype that individual for the FGG-H2 tagging polymorphism 10034C/T using the 5' nuclease/TaqMan assay.

In a typical assay 90 DNA samples and 6 blanks are analysed in a 96-wells plate. For genotyping of FGG SNP 10034C/T a PCR was performed using 10 ng of genomic DNA, 200 μM of each dNTP, PCR buffer (KCl, Tris-HCl), 3 mM $MgCl_2$, 490 nM of each primer, 109 nM of each probe and 0.5 U Hot Goldstar polymerase (Eurogentec) in a final volume of 22 μl. Reaction buffer, $MgCl_2$, dNTP mix and Goldstar polymerase were from Eurogentec, Seraing, Belgium (qPCR™ Core Kit, Cat. no. RT-QP73-05)

The primers and the probes were obtained as a single-mix Assay-on-Demand from Applied Biosystems (Foster City, USA). Thermal cycling was carried out by incubation at 95° C. for 10 minutes, followed by 40 cycles of denaturation at 95° C. for 15 seconds and annealing/extension at 60° C. for 1 minute. The thermal reactions were performed on a PTC-225 thermal cycler (Biozym, Hessisch Oldendorf, Germany) and fluorescence endpoint reading for allelic discrimination was done on an ABI 7900 HT (Applied Biosystems, Foster City, USA).

A typical example of results that can be obtained are given in FIGS. 6 and 7, where allele X is FGG 10034C and allele Y is FGG 10034T. Individuals with genotype 10034CC are red (lower right), those with genotype 10034CT are green (middle right) and those with the risk genotype 10034TT are blue(upper left). The blanks are in black (lower left). DNA samples were randomly selected from the Leiden Thrombophilia Study, without information on the patient/control status.

The following primers and probes were used:

```
Forward primer:
                                        (SEQ ID NO: 48)
5'-ACATGCATTTCAATAAACCTTTTGTTTCCT-3'
```

-continued

Reverse primer:
(SEQ ID NO: 49)
5'-GGTAAATTGGCAAAAAGTGGTGGT-3'

Probe 1 (VIC-labeled):
(SEQ ID NO: 50)
5'-TTTTAATGGTCAATAAAGGTACCA-3'

Probe 2 (FAM-labeled):
(SEQ ID NO: 51)
5'-ATGGTCAATAAAGATACCA-3'

VIC and FAM were the fluoresecent groups, attached at the 3' end of the probe; TAMRA was used as a quencher connected to the 5' end of the probe. Probe 2 detects the FGG-H2 haplotype by binding to the rare 10034T allele. Probe 1 detects all non haplotypes of FGG by binding to 10034C allele.

The invention claimed is:

1. A method for screening an individual for having an increased risk of venous thrombosis, comprising determining the presence in the individual's genome of a genetic marker that is indicative of an increased risk of venous thrombosis, wherein the genetic marker is at least part of haplotype 2 of the fibrinogen γ gene (FGG-H2), wherein the presence of FGG-H2 is associated with the presence of a set of one, two, three or four mutations in the nucleic acid encoding fibrinogen γ, the mutations being selected from the group consisting of 129A/T (rs2066854), 7874G/A (rs2066861), 9615C/T (rs2066864) and 10034C/T (rs2066865).

2. The method of claim 1, wherein the set of mutations is selected from the sets listed in the following table:

| Set | Mutations | | | |
|---|---|---|---|---|
| 1 | 129A/T | | | |
| 2 | 129A/T | 7874G/A | | |
| 3 | 129A/T | 7874G/A | 9615C/T | |
| 4 | 129A/T | | 9615C/T | |
| 5 | 129A/T | | 9615C/T | 10034C/T |
| 6 | 129A/T | | | 10034C/T |
| 7 | 129A/T | 7874G/A | | 10034C/T |
| 8 | 129A/T | 7874G/A | 9615C/T | 10034C/T |
| 9 | | 7874G/A | | |
| 10 | | 7874G/A | 9615C/T | |
| 11 | | 7874G/A | 9615C/T | 10034C/T |
| 12 | | 7874G/A | | 10034C/T |
| 13 | | | 9615C/T | |
| 14 | | | 9615C/T | 10034C/T |
| 15 | | | | 10034C/T. |

3. The method of claim 2, wherein the set of mutations is selected from the sets listed in the following table:

| Set | Mutations | | | |
|---|---|---|---|---|
| 5 | 129A/T | | 9615C/T | 10034C/T |
| 6 | 129A/T | | | 10034C/T |
| 7 | 129A/T | 7874G/A | | 10034C/T |
| 8 | 129A/T | 7874G/A | 9615C/T | 10034C/T |
| 11 | | 7874G/A | 9615C/T | 10034C/T |
| 12 | | 7874G/A | | 10034C/T |
| 14 | | | 9615C/T | 10034C/T |
| 15 | | | | 10034C/T. |

4. The method of claim 1, wherein the presence of FGG-H2 is associated with the presence of mutation 10034C/T (rs2066865) in the nucleic acid encoding fibrinogen γ.

5. The method of claim 1, wherein said marker is detected by carrying out a target nucleic acid amplification reaction of a stretch of nucleic acid comprising said set of mutations and analyzing the amplified target nucleic acid for the presence of the set of mutations.

6. The method of claim 5, wherein the amplification reaction is selected from the group consisting of NASBA, PCR, LCR, RCR, 3SR and TMA.

7. The method of claim 5, wherein each amplified nucleic acid forms a detectable complex with a complementary oligonucleotide.

8. The method of claim 7, wherein the complementary oligonucleotide is immobilized on a solid phase and each of the detectable complexes reacts with a labeled reactant.

9. The method of claim 7, wherein the complementary oligonucleotide is immobilized on a solid phase and each of the detectable complexes will react differently with labeled reactants.

10. The method of claim 9, wherein the different amplified nucleic acids form a detectable complex with a different complementary oligonucleotide and/or said different complementary oligonucleotides are each immobilized at a different spot on a solid phase.

11. A kit comprising one pair of amplification primers recognizing and hybridizing to stretches of nucleic acid surrounding one stretch of a target nucleic acid to be amplified, which target nucleic acid corresponds to at least part of the fibrinogen γ gene that comprises at least one mutation selected from the group consisting of 129A/T, 7874G/A, 9615C/T and 10034C/T, and at least one probe for detecting each mutation of interest in the amplified target nucleic acid and means for detecting the amplified target nucleic acid for the presence of said mutation(s).

12. The kit of claim 11, comprising:
(a) a first oligonucleotide being 10-50 nucleotides in length and comprising one of the following nucleotide sequences or at least a fragment of 10 nucleotides thereof:

```
SEQ ID NO: 1:   CTTCACAGAGGCAACTGATTC,

SEQ ID NO: 2:   CCTTCAGACAAAGGGAAGATTG,

SEQ ID NO: 3:   AGCTCCAGCCATTTGCAG,

SEQ ID NO: 4:   TCAGGTCCACATTGTATTCC,

SEQ ID NO: 5:   GGGAGTTGATAGAACCAGTGC,

SEQ ID NO: 6:   TTCCAAGGAAGCATCCTACG,

SEQ ID NO: 7:   GTAACTGGCAATGCACTTCG,

SEQ ID NO: 8:   GAGAACATTTTAGAGTTTCAAATTC,
or

SEQ ID NO: 9:   ACATGCATTTCAATAAACCTTTTGTTTCCT,
``` or the complementary sequence thereof, and
(b) a second oligonucleotide being 10-50 nucleotides in length and comprising one of the following nucleotide sequences or at least a fragment of 10 nucleotides thereof:

```
SEQ ID NO: 10:  GTGTCAACCATGTTCATAGGC,

SEQ ID NO: 11:  CCTTTTATGTAAGCTCCTGGG,

SEQ ID NO: 12:  CATAATCAGGCATAATGTCACTG,

SEQ ID NO: 13:  TGAGCTACGGTTCACAAGG,

SEQ ID NO: 14:  GACTCCTGGAGAAAATGGTG,
```

```
SEQ ID NO: 15:    GGTGGATTTCTTTAGAAGGGC,

SEQ ID NO: 16:    GCTTTGCAAGTCCATTGTCC,

SEQ ID NO: 17:    GCTATTTCCTTTGTAACTCCC,
or

SEQ ID NO: 18:    GGTAAATTGGCAAAAAGTGGTGGT,
``` or the complementary sequence thereof.

13. The kit of claim 11, for detecting mutation 129A/T comprising:
(a) a first oligonucleotide being 10-50 nucleotides in length and comprising one of the following nucleotide sequences or at least a fragment of 10 nucleotides thereof:

```
SEQ ID NO: 1:     CTTCACAGAGGCAACTGATTC,
``` or the complementary sequence thereof, and
(b) a second oligonucleotide being 10-50 nucleotides in length and comprising the following nucleotide sequences or at least a fragment of 10 nucleotides thereof:

```
SEQ ID NO: 2:     CCTTCAGACAAAGGGAAGATTG,

SEQ ID NO: 3:     AGCTCCAGCCATTTGCAG,

SEQ ID NO: 4:     TCAGGTCCACATTGTATTCC,

SEQ ID NO: 5:     GGGAGTTGATAGAACCAGTGC,

SEQ ID NO: 6:     TTCCAAGGAAGCATCCTACG,

SEQ ID NO: 7:     GTAACTGGCAATGCACTTCG,

SEQ ID NO: 8:     GAGAACATTTTAGAGTTTCAAATTC,

SEQ ID NO: 9:     ACATGCATTTCAATAAACCTTTTGTTTCCT,

SEQ ID NO: 10:    GTGTCAACCATGTTCATAGGC,

SEQ ID NO: 11:    CCTTTTATGTAAGCTCCTGGG,

SEQ ID NO: 12:    CATAATCAGGCATAATGTCACTG,

SEQ ID NO: 13:    TGAGCTACGGTTCACAAGG,

SEQ ID NO: 14:    GACTCCTGGAGAAAATGGTG,

SEQ ID NO: 15:    GGTGGATTTCTTTAGAAGGGC,

SEQ ID NO: 16:    GCTTTGCAAGTCCATTGTCC,

SEQ ID NO: 17:    GCTATTTCCTTTGTAACTCCC,
or

SEQ ID NO: 18:    GGTAAATTGGCAAAAAGTGGTGGT,
``` or the complementary sequence thereof.

14. The kit of claim 13, wherein the first oligonucleotide is 10-26 nucleotides in length, and the second oligonucleotide is 10-26 nucleotides in length and comprises SEQ ID NO:10 or at least a fragment of 10 nucleotides thereof.

15. The kit of claim 11, for detecting mutation 7874G/A comprising:
(a) a first oligonucleotide being 10-50 nucleotides in length and comprising one of the following nucleotide sequences or at least a fragment of 10 nucleotides thereof:

```
SEQ ID NO: 1:     CTTCACAGAGGCAACTGATTC,

SEQ ID NO: 2:     CCTTCAGACAAAGGGAAGATTG,

SEQ ID NO: 3:     AGCTCCAGCCATTTGCAG,

SEQ ID NO: 4:     TCAGGTCCACATTGTATTCC,

SEQ ID NO: 5:     GGGAGTTGATAGAACCAGTGC,

SEQ ID NO: 6:     TTCCAAGGAAGCATCCTACG,

SEQ ID NO: 10:    GTGTCAACCATGTTCATAGGC,

SEQ ID NO: 11:    CCTTTTATGTAAGCTCCTGGG,

SEQ ID NO: 12:    CATAATCAGGCATAATGTCACTG,

SEQ ID NO: 13:    TGAGCTACGGTTCACAAGG,

SEQ ID NO: 14:    GACTCCTGGAGAAAATGGTG,
or

SEQ ID NO: 15:    GGTGGATTTCTTTAGAAGGGC,
``` or the complementary sequence thereof, and
(b) a second oligonucleotide being 10-50 nucleotides in length and comprising one of the following nucleotide sequences or at least a fragment of 10 nucleotides thereof:

```
SEQ ID NO: 7:     GTAACTGGCAATGCACTTCG,

SEQ ID NO: 8:     GAGAACATTTTAGAGTTTCAAATTC,

SEQ ID NO: 9:     ACATGCATTTCAATAAACCTTTTGTTTCCT,

SEQ ID NO: 16:    GCTTTGCAAGTCCATTGTCC,

SEQ ID NO: 17:    GCTATTTCCTTTGTAACTCCC,
or

SEQ ID NO: 18:    GGTAAATTGGCAAAAAGTGGTGGT,
``` or the complementary sequence thereof.

16. The kit of claim 15, wherein the first oligonucleotide is 10-26 nucleotides in length and comprises: SEQ ID NO:6 or at least a fragment of 10 nucleotides thereof, and the second oligonucleotide is 10-26 nucleotides in length and comprises SEQ ID NO:16 or at least a fragment of 10 nucleotides thereof.

17. The kit of claim 11, for detecting mutation 9615C/T comprising:
(a) a first oligonucleotide being 10-50 nucleotides in length and comprising one of the following nucleotide sequences or at least a fragment of 10 nucleotides thereof:

```
SEQ ID NO: 1:     CTTCACAGAGGCAACTGATTC,

SEQ ID NO: 2:     CCTTCAGACAAAGGGAAGATTG,

SEQ ID NO: 3:     AGCTCCAGCCATTTGCAG,

SEQ ID NO: 4:     TCAGGTCCACATTGTATTCC,

SEQ ID NO: 5:     GGGAGTTGATAGAACCAGTGC,

SEQ ID NO: 6:     TTCCAAGGAAGCATCCTACG,

SEQ ID NO: 7:     GTAACTGGCAATGCACTTCG,

SEQ ID NO: 10:    GTGTCAACCATGTTCATAGGC,
```

```
SEQ ID NO: 11:     CCTTTTATGTAAGCTCCTGGG,
SEQ ID NO: 12:     CATAATCAGGCATAATGTCACTG,
SEQ ID NO: 13:     TGAGCTACGGTTCACAAGG,
SEQ ID NO: 14:     GACTCCTGGAGAAAATGGTG,
or
SEQ ID NO: 15:     GGTGGATTTCTTTAGAAGGGC,
``` or the complementary sequence thereof, and
(b) a second oligonucleotide being 10-50 nucleotides in length and comprising one of the following nucleotide sequences or at least a fragment of 10 nucleotides thereof:

```
SEQ ID NO: 8:      GAGAACATTTTAGAGTTTCAAATTC,
SEQ ID NO: 9:      ACATGCATTTCAATAAACCTTTTGTTTCCT,
SEQ ID NO: 16:     GCTTTGCAAGTCCATTGTCC,
SEQ ID NO: 17:     GCTATTTCCTTTGTAACTCCC,
or
SEQ ID NO: 18:     GGTAAATTGGCAAAAAGTGGTGGT,
``` or the complementary sequence thereof.

18. The kit of claim 17, wherein the first oligonucleotide is 10-26 nucleotides in length and comprises SEQ ID NO:7 or at least a fragment of 10 nucleotides thereof, and the second oligonucleotide is 10-26 nucleotides in length and comprises SEQ ID NO:16 or at least a fragment of 10 nucleotides thereof.

19. The kit of claim 11, for detecting mutation 10034C/T comprising:
(a) a first oligonucleotide being 10-50 nucleotides in length and comprising one of the following nucleotide sequences or at least a fragment of 10 nucleotides thereof:

```
SEQ ID NO: 1:      CTTCACAGAGGCAACTGATTC,
SEQ ID NO: 2:      CCTTCAGACAAAGGGAAGATTG,
SEQ ID NO: 3:      AGCTCCAGCCATTTGCAG,
SEQ ID NO: 4:      TCAGGTCCACATTGTATTCC,
SEQ ID NO: 5:      GGGAGTTGATAGAACCAGTGC,
SEQ ID NO: 6:      TTCCAAGGAAGCATCCTACG,
SEQ ID NO: 7:      GTAACTGGCAATGCACTTCG,
SEQ ID NO: 8:      GAGAACATTTTAGAGTTTCAAATTC,
SEQ ID NO: 9:      ACATGCATTTCAATAAACCTTTTGTTTCCT,
SEQ ID NO: 10:     GTGTCAACCATGTTCATAGGC,
SEQ ID NO: 11:     CCTTTTATGTAAGCTCCTGGG,
SEQ ID NO: 12:     CATAATCAGGCATAATGTCACTG,
SEQ ID NO: 13:     TGAGCTACGGTTCACAAGG,
SEQ ID NO: 14:     GACTCCTGGAGAAAATGGTG,
SEQ ID NO: 15:     GGTGGATTTCTTTAGAAGGGC,
or
SEQ ID NO: 16:     GCTTTGCAAGTCCATTGTCC,
``` or the complementary sequence thereof, and
(b) a second oligonucleotide being 10-50 nucleotides in length and comprising one of the following nucleotide sequences or at least a fragment of 10 nucleotides thereof:

```
SEQ ID NO: 17:     GCTATTTCCTTTGTAACTCCC,
or
SEQ ID NO: 18:     GGTAAATTGGCAAAAAGTGGTGGT,
``` or the complementary sequence thereof.

20. The kit of claim 19, wherein the first oligonucleotide is 10-26 nucleotides in length and comprises SEQ ID NO:8 or SEQ ID NO:9 or at least a fragment of 10 nucleotides thereof, and the second oligonucleotide is 10-26 nucleotides in length.

21. The kit of claim 11, wherein there is one probe for detecting each mutation of interest comprising 129A/T, 7874G/A, 9615C/T or 10034C/T in the amplified target nucleic acid, said probe comprising a nucleic acid sequence corresponding to an analyte nucleic acid that has been mutated to discriminate said analyte nucleic acid from a non-mutated analyte nucleic acid.

22. The kit of claim 21, wherein the probe is a molecular beacon.

23. The kit of claim 21, comprising a probe for detecting FGG-H2 haplotype by binding to the 10034T allele, comprising an oligonucleotide of 10-50 nucleotides in length, and comprising SEQ ID NO:19 or at least a fragment of 10 nucleotides thereof.

24. The kit of claim 21, comprising a probe for detecting FGG-H2 haplotype by binding to the 10034C allele, comprising an oligonucleotide of 10-50 nucleotides in length, and comprising SEQ ID NO:20 or at least a fragment of 10 nucleotides thereof.

25. The kit of claim 11, wherein the kit further contains suitable amplification reagents.

26. A method for screening an individual for an increased risk of venous thrombosis by determining the presence in his/her genome of a genetic marker that is indicative of the increased risk, wherein the method combines a method of claim 1, with determination of the fibrinogen γ'/total fibrinogen ratio (γ'/γ ratio).

27. The method of claim 26, wherein an increased risk of deep venous thrombosis corresponds to a γ'/γ ratio below 0.69.

* * * * *

UNITED STATES PATENT AND TRADEMARK OFFICE
CERTIFICATE OF CORRECTION

PATENT NO.        : 8,067,209 B2
APPLICATION NO.   : 11/887495
DATED             : November 29, 2011
INVENTOR(S)       : Bertina et al.

It is certified that error appears in the above-identified patent and that said Letters Patent is hereby corrected as shown below:

On the Title Page:
Item (56) References Cited, Other Publications, right column:
  De Willige et al., Line 18:
    correct "fibrinogen $\gamma^1$ levels"
    to read -- fibrinogen γ' levels --
  Drouet et al., Line 19:
    correct "Plasma $\gamma^1 / \gamma^1$ fibrogen"
    to read -- Plasma γ' / γ' fibrogen --
  Fellowes et al., Line 24:
    correct "Sciences 936: 636-541"
    to read -- Sciences 936: 536-541 --

Title page, Item (57) Abstract, Line 9: correct "7874G/A (rs20668β1)"
    to read: 7874G/A (rs2066861) --

Column 13, Line 6: correct "C at the end" to read -- $\underline{C^{}}$ at the end --

Column 17, Line 13: correct "x1=categories" to read -- $X_1$=categories --

Column 26, Line 50: correct "TCTAGA CCA CCA TGG"
    to read -- TCT AGA CCA CCA TGG --

Signed and Sealed this
Thirteenth Day of March, 2012

David J. Kappos
*Director of the United States Patent and Trademark Office*